(12) United States Patent
Haseltine et al.

(10) Patent No.: US 6,416,984 B1
(45) Date of Patent: Jul. 9, 2002

(54) HUMAN DNA MISMATCH REPAIR PROTEINS

(75) Inventors: William A. Haseltine, Washington, DC (US); Steven M. Ruben, Olney, MD (US); Ying-Fei Wei, Darnestown, MD (US); Mark D. Adams, North Potomac, MD (US); Robert D. Fleischmann, Gaithersburg, MD (US); Claire M. Fraser, Potomac, MD (US); Rebecca A. Fuldner, Barnesville, MD (US); Ewen F. Kirkness, Olney, MD (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 08/468,024

(22) Filed: Jun. 6, 1995

Related U.S. Application Data

(63) Continuation-in-part of application No. PCT/US95/01035, filed on Jan. 25, 1995, and a continuation-in-part of application No. 08/294,312, filed on Aug. 23, 1994, which is a continuation-in-part of application No. 08/210,143, filed on Mar. 16, 1994, which is a continuation-in-part of application No. 08/187,757, filed on Jan. 27, 1994.

(51) Int. Cl.[7] .............................................. C12N 9/00

(52) U.S. Cl. ...................................... 435/183; 435/195

(58) Field of Search ............................... 435/183, 199; 536/23.2, 23.5

(56) References Cited

U.S. PATENT DOCUMENTS

| | | | |
|---|---|---|---|
| 4,737,454 A | 4/1988 | Dattagupta et al. | ............ 435/6 |
| 5,124,443 A | 6/1992 | Colella et al. | ............. 536/27 |
| 5,922,855 A * | 7/1999 | Liskay et al. | ............ 536/23.5 |
| 6,165,713 A | 12/2000 | Liskay et al. | ............... 435/6 |
| 6,191,268 B1 | 2/2001 | Liskay et al. | ............ 436/23.5 |

FOREIGN PATENT DOCUMENTS

| | | |
|---|---|---|
| WO | WO 95/14772 | 11/1993 |
| WO | WO 95/14085 | 11/1994 |
| WO | WO 95/16793 | 12/1994 |
| WO | WO 95/14085 * | 5/1995 |
| WO | WO 95/15381 A2 | 6/1995 |

OTHER PUBLICATIONS

Ford et al. "Fusion tails for the recovery and purification of recombinant proteins" Prot. Exp. Purif. (1991) 2, 95–107.*
Papadopoulos et al. "Mutation of a mutL homolog in hereditary colon cancer" Science 263, 1625–1629, Mar. 18, 1994.*
Bronner et al. "Mutation in the DNA mismatch repair gene homologue hMLH1 is associated with hereitary non-polypsis colon cancer" Nature 368, 258–261, Mar. 17, 1994.*
Nicolaides et al. "Mutations of two PMS homologues in hereditary nonpolyposis colon cancer" Nature 371, 75–80, Sep. 1, 1994.*
Green et al. "Systematic generation of a sequence–tagged sites for physical mapping of human. . . " Genomics 11, 548–564, 1991.*
U.S. application No. 08/154,792, Kolodner et al., filed Nov. 17, 1993.
U.S. application No. 08/163,449, Kolodner et al., filed Dec. 7, 1993.
U.S. application No. 08/259,370, Kolodner et al., filed Feb. 22, 1995.
GenBank Accession No. D12046, (Dec. 2, 1992).
GenBank Accession No. Z24775, (Aug. 2, 1993).
GenBank Accession No. Z36291, (Aug. 15, 1994).
Geneseq Accession No. AAT29623, (Apr. 30, 1996).
Geneseq Accession No. AAT29624, (Apr. 30, 1996).
Geneseq Accession No. AAT26925. (Apr. 30, 1996).
Geneseq Accession No. AAT26926. (Apr. 30, 1996).
Geneseq Accession No. AAT26927. (Apr. 30, 1996).
Geneseq Accession No. AAT26928. (Apr. 30, 1996).
Baker et al., Male Mice Defective in the DNA Mismatch Repair Gen PMS2 Exhibit Abnormal Chromosome Synapsis in Meiosis, *Cell*, 82:309–319 (1995).
Fishel et al., The Human Mutator Gene Homologue MSH2 and Its Association With Hereditary Nonpolyposis Colon Cancer, *Cell*, 75: 1027–1038 (1993).
HJ Han, Genomic structure of human mismatch repair gene, hMLH1, and its mutation analysis in patients with hereditary non–polyposis colorectal cancer (HNPCC), *Hum. Mol. Genet.*, 4:237–242 (1995).
Horii et al., Cloning, Characterization and Chromosomal Assignment of the Human Genes Homologous to Yeast *PMS1*, A Member of Mismatch Repair Genes, *Biochemical and Biophysical Research Communications*, 204; 1257–1264 (1994).
Jacoby et al, Genetic instability associated with adenoma to carcinoma progression in hereditary nonpolyposis colon cancer, *Gastroenterology*, 109(1) 73–82 (1995).
Kolodner et al., Structure of the human *MLH1* locus and analysis of a large hereditary nonpolyposis colorectal carcinoma kindred for *mlh1* mutations, *Cancer Research*, 55:242–248, (1995).

(List continued on next page.)

Primary Examiner—Nashaat T. Nashed
(74) Attorney, Agent, or Firm—Human Genome Sciences, Inc.

(57) ABSTRACT

The invention discloses three human DNA repair proteins and DNA (RNA) encoding such proteins and a procedure for producing such proteins by recombinant techniques. One of the human DNA repair proteins, hMLH1, has been mapped to chromosome 3 while hMLH2 has been mapped to chromosome 2 and hMLH3 has been mapped to chromosome 7. The polynucleotide sequences of the DNA repair proteins may be used for therapeutic and diagnostic treatments of a hereditary susceptibility to cancer.

48 Claims, 26 Drawing Sheets

OTHER PUBLICATIONS

Kramer et al., Cloning and Nucleotide Sequence of DNA Mismatch Repair Gene *PMS1* from *Saccharomyces cerevisiae*: Homology of PMSI to Procaryotic MutL and HexB, *J. of Bacteriology*, 171:5339–5356, (1989).

Leach F. S. et al., Mutations of a *mutS* Homolog in Hereditary Nonpolyposis Colorectal Cancer, *Cell*, 75:1215–1225 (1993).

Lindblom et al., Genetic mapping of a second locus predisposing to hereditary non–polyposis colon cancer, *Nature Genetics*, 5:279–282 (1993).

New et al., The yeast gene *MSH3* defines a new class of eukaryotic MutS homologues, *Mol. Gen. Gent.* 239:97–108 (1993).

Nyström–Lahti, Mismatch Repair Genes on Chromosomes 2p and 3p Account for a Major Share of Hereditary Nonpolyposis Colorectal Cancer Families Evaluable by Linkage, *American Journal of Human Genes*, 55:659–665 (1994).

Okubo et al., Large Scale cDNA sequencing for analysis of quantitative and qualitative aspects of gene expression, *Nature Genetics*, 2:173–179 (1992).

Prolla et al., Dual Requirement in Yeast DNA Mismatch Repair for *MLH1* and *PMS1* , Two Homologs of the Bacterial *mutL* Gene, *Molecular and Cellular Biology*, 14:407–415 (1994).

Prolla et al., MLH1, PMS1, and MSH2 Interactions During the Initiation of DNA Mismatch in Repair Yeast, *Science*, 265: 1091–1093 (1994).

Radman et al., DNA Mismatch Repair Systems: Mechanisms and Applications in Biotechnology, *Biotechnology and Genetic Engineering Reviews*, 11:357–366 (1993).

\* cited by examiner

Polynucleotide and deduced amino acid sequence of hMLH1

```
-40                 -20                  1
.                    .                   .
GTTGAACATCTAGACGTTTCCTTGGCTCTTCTGGCGCCAAAATGTCGTTCGTGGCAGGGG
+---------+---------+---------+---------+---------+---------
CAACTTGTAGATCTGCAAAGGAACCGAGAAGACCGCGGTTTTACAGCAAGCACCGTCCCC
                                         M  S  F  V  A  G  V
20                  40                  60
.                   .                   .
TTATTCGGCGGCTGGACGAGACAGTGGTGAACCGCATCGCGGCGGGGGAAGTTATCCAGC
+---------+---------+---------+---------+---------+---------
AATAAGCCGCCGACCTGCTCTGTCACCACTTGGCGTAGCGCCGCCCCCTTCAATAGGTCG
   I  R  R  L  D  E  T  V  V  N  R  I  A  A  G  E  V  I  Q  R
80                 100                 120
.                   .                   .
GGCCAGCTAATGCTATCAAAGAGATGATTGAGAACTGTTTAGATGCAAAATCCACAAGTA
+---------+---------+---------+---------+---------+---------
CCGGTCGATTACGATAGTTTCTCTACTAACTCTTGACAAATCTACGTTTTAGGTGTTCAT
   P  A  N  A  I  K  E  M  I  E  N  C  L  D  A  K  S  T  S  I
140                 160                 180
.                   .                   .
TTCAAGTGATTGTTAAAGAGGGAGGCCTGAAGTTGATTCAGATCCAAGACAATGGCACCG
+---------+---------+---------+---------+---------+---------
AAGTTCACTAACAATTTCTCCCTCCGGACTTCAACTAAGTCTAGGTTCTGTTACCGTGGC
   Q  V  I  V  K  E  G  G  L  K  L  I  Q  I  Q  D  N  G  T  G
200                 220                 240
.                   .                   .
GGATCAGGAAAGAAGATCTGGATATTGTATGTGAAAGGTTCACTACTAGTAAACTGCAGT
+---------+---------+---------+---------+---------+---------
CCTAGTCCTTTCTTCTAGACCTATAACATACACTTTCCAAGTGATGATCATTTGACGTCA
   I  R  K  E  D  L  D  I  V  C  E  R  F  T  T  S  K  L  Q  S
260                 280                 300
.                   .                   .
CCTTTGAGGATTTAGCCAGTATTTCTACCTATGGCTTTCGAGGTGAGGCTTTGGCCAGCA
+---------+---------+---------+---------+---------+---------
GGAAACTCCTAAATCGGTCATAAAGATGGATACCGAAAGCTCCACTCCGAAACCGGTCGT
   F  E  D  L  A  S  I  S  T  Y  G  F  R  G  E  A  L  A  S  I
320                 340                 360
.                   .                   .
TAAGCCATGTGGCTCATGTTACTATTACAACGAAAACAGCTGATGGAAAGTGTGCATACA
+---------+---------+---------+---------+---------+---------
ATTCGGTACACCGAGTACAATGATAATGTTGCTTTTGTCGACTACCTTTCACACGTATGT
   S  H  V  A  H  V  T  I  T  T  K  T  A  D  G  K  C  A  Y  R
```

FIG. 1A

```
380                     400                     420
 .         .         .         .         .         .
GAGCAAGTTACTCAGATGGAAAACTGAAAGCCCCTCCTAAACCATGTGCTGGCAATCAAG
+---------+---------+---------+---------+---------+---------
CTCGTTCAATGAGTCTACCTTTTGACTTTCGGGGAGGATTTGGTACACGACCGTTAGTTC
   A  S  Y  S  D  G  K  L  K  A  P  P  K  P  C  A  G  N  Q  G
440                     460                     480
 .         .         .         .         .         .
GGACCCAGATCACGGTGGAGGACCTTTTTTACAACATAGCCACGAGGAGAAAAGCTTTAA
+---------+---------+---------+---------+---------+---------
CCTGGGTCTAGTGCCACCTCCTGGAAAAAATGTTGTATCGGTGCTCCTCTTTTCGAAATT
   T  Q  I  T  V  E  D  L  F  Y  N  I  A  T  R  R  K  A  L  K
500                     520                     540
 .         .         .         .         .         .
AAAATCCAAGTGAAGAATATGGGAAAATTTTGGAAGTTGTTGGCAGGTATTCAGTACACA
+---------+---------+---------+---------+---------+---------
TTTTAGGTTCACTTCTTATACCCTTTTAAAACCTTCAACAACCGTCCATAAGTCATGTGT
   N  P  S  E  E  Y  G  K  I  L  E  V  V  G  R  Y  S  V  H  N
560                     580                     600
 .         .         .         .         .         .
ATGCAGGCATTAGTTTCTCAGTTAAAAAACAAGGAGAGACAGTAGCTGATGTTAGGACAC
+---------+---------+---------+---------+---------+---------
TACGTCCGTAATCAAAGAGTCAATTTTTTGTTCCTCTCTGTCATCGACTACAATCCTGTG
   A  G  I  S  F  S  V  K  K  Q  G  E  T  V  A  D  V  R  T  L
620                     640                     660
 .         .         .         .         .         .
TACCCAATGCCTCAACCGTGGACAATATTCGCTCCGTCTTTGGAAATGCTGTTAGTCGAG
+---------+---------+---------+---------+---------+---------
ATGGGTTACGGAGTTGGCACCTGTTATAAGCGAGGCAGAAACCTTTACGACAATCAGCTC
   P  N  A  S  T  V  D  N  I  R  S  V  F  G  N  A  V  S  R  E
680                     700                     720
 .         .         .         .         .         .
AACTGATAGAAATTGGATGTGAGGATAAAACCCTAGCCTTCAAAATGAATGGTTACATAT
+---------+---------+---------+---------+---------+---------
TTGACTATCTTTAACCTACACTCCTATTTTGGGATCGGAAGTTTTACTTACCAATGTATA
   L  I  E  I  G  C  E  D  K  T  L  A  F  K  M  N  G  Y  I  S
740                     760                     780
 .         .         .         .         .         .
CCAATGCAAACTACTCAGTGAAGAAGTGCATCTTCTTACTCTTCATCAACCATCGTCTGG
+---------+---------+---------+---------+---------+---------
GGTTACGTTTGATGAGTCACTTCTTCACGTAGAAGAATGAGAAGTAGTTGGTAGCAGACC
   N  A  N  Y  S  V  K  K  C  I  F  L  L  F  I  N  H  R  L  V
```

FIG. 1B

```
             800                 820                  840
              .                   .                    .
              .                   .                    .
TAGAATCAACTTCCTTGAGAAAAGCCATAGAAACAGTGTATGCAGCCTATTTGCCCAAAA
+---------+---------+---------+---------+---------+---------
ATCTTAGTTGAAGGAACTCTTTTCGGTATCTTTGTCACATACGTCGGATAAACGGGTTTT
   E  S  T  S  L  R  K  A  I  E  T  V  Y  A  A  Y  L  P  K  N
             860                 880                  900
              .                   .                    .
              .                   .                    .
ACACACACCCATTCCTGTACCTCAGTTTAGAAATCAGTCCCCAGAATGTGGATGTTAATG
+---------+---------+---------+---------+---------+---------
TGTGTGTGGGTAAGGACATGGAGTCAAATCTTTAGTCAGGGGTCTTACACCTACAATTAC
   T  H  P  F  L  Y  L  S  L  E  I  S  P  Q  N  V  D  V  N  V
             920                 940                  960
              .                   .                    .
              .                   .                    .
TGCACCCCACAAAGCATGAAGTTCACTTCCTGCACGAGGAGAGCATCCTGGAGCGGGTGC
+---------+---------+---------+---------+---------+---------
ACGTGGGGTGTTTCGTACTTCAAGTGAAGGACGTGCTCCTCTCGTAGGACCTCGCCCACG
   H  P  T  K  H  E  V  H  F  L  H  E  E  S  I  L  E  R  V  Q
             980                 1000                 1020
              .                   .                    .
              .                   .                    .
AGCAGCACATCGAGAGCAAGCTCCTGGGCTCCAATTCCTCCAGGATGTACTTCACCCAGA
+---------+---------+---------+---------+---------+---------
TCGTCGTGTAGCTCTCGTTCGAGGACCCGAGGTTAAGGAGGTCCTACATGAAGTGGGTCT
   Q  H  I  E  S  K  L  L  G  S  N  S  S  R  M  Y  F  T  Q  T
             1040                1060                 1080
              .                   .                    .
              .                   .                    .
CTTTGCTACCAGGACTTGCTGGCCCCTCTGGGGAGATGGTTAAATCCACAACAAGTCTGA
+---------+---------+---------+---------+---------+---------
GAAACGATGGTCCTGAACGACCGGGGAGACCCCTCTACCAATTTAGGTGTTGTTCAGACT
   L  L  P  G  L  A  G  P  S  G  E  M  V  K  S  T  T  S  L  T
             1100                1120                 1140
              .                   .                    .
              .                   .                    .
CCTCGTCTTCTACTTCTGGAAGTAGTGATAAGGTCTATGCCCACCAGATGGTTCGTACAG
+---------+---------+---------+---------+---------+---------
GGAGCAGAAGATGAAGACCTTCATCACTATTCCAGATACGGGTGGTCTACCAAGCATGTC
   S  S  S  T  S  G  S  S  D  K  V  Y  A  H  Q  M  V  R  T  D
             1160                1180                 1200
              .                   .                    .
              .                   .                    .
ATTCCCGGGAACAGAAGCTTGATGCATTTCTGCAGCCTCTGAGCAAACCCCTGTCCAGTC
+---------+---------+---------+---------+---------+---------
TAAGGGCCCTTGTCTTCGAACTACGTAAAGACGTCGGAGACTCGTTTGGGGACAGGTCAG
   S  R  E  Q  K  L  D  A  F  L  Q  P  L  S  K  P  L  S  S  Q
```

FIG. 1C

```
                1220                  1240                    1260
                  .                     .                       .
          AGCCCCAGGCCATTGTCACAGAGGATAAGACAGATATTTCTAGTGGCAGGGCTAGGCAGC
          +---------+---------+---------+---------+---------+---------
          TCGGGGTCCGGTAACAGTGTCTCCTATTCTGTCTATAAAGATCACCGTCCCGATCCGTCG
              P  Q  A  I  V  T  E  D  K  T  D  I  S  S  G  R  A  R  Q  Q
           1280                  1300                    1320
                  .                     .                       .
          AAGATGAGGAGATGCTTGAACTCCCAGCCCCTGCTGAAGTGGCTGCCAAAAATCAGAGCT
          +---------+---------+---------+---------+---------+---------
          TTCTACTCCTCTACGAACTTGAGGGTCGGGGACGACTTCACCGACGGTTTTTAGTCTCGA
              D  E  E  M  L  E  L  P  A  P  A  E  V  A  A  K  N  Q  S  L
           1340                  1360                    1380
                  .                     .                       .
          TGGAGGGGGATACAACAAAGGGGACTTCAGAAATGTCAGAGAAGAGAGGACCTACTTCCA
          +---------+---------+---------+---------+---------+---------
          ACCTCCCCCTATGTTGTTTCCCCTGAAGTCTTTACAGTCTCTTCTCTCCTGGATGAAGGT
              E  G  D  T  T  K  G  T  S  E  M  S  E  K  R  G  P  T  S  S
           1400                  1420                    1440
                  .                     .                       .
          GCAACCCCAGAAAGAGACATCGGGAAGATTCTGATGTGGAAATGGTGGAAGATGATTCCC
          +---------+---------+---------+---------+---------+---------
          CGTTGGGGTCTTTCTCTGTAGCCCTTCTAAGACTACACCTTTACCACCTTCTACTAAGGG
              N  P  R  K  R  H  R  E  D  S  D  V  E  M  V  E  D  D  S  R
           1460                  1480                    1500
                  .                     .                       .
          GAAAGGAAATGACTGCAGCTTGTACCCCCCGGAGAAGGATCATTAACCTCACTAGTGTTT
          +---------+---------+---------+---------+---------+---------
          CTTTCCTTTACTGACGTCGAACATGGGGGGCCTCTTCCTAGTAATTGGAGTGATCACAAA
              K  E  M  T  A  A  C  T  P  R  R  R  I  I  N  L  T  S  V  L
           1520                  1540                    1560
                  .                     .                       .
          TGAGTCTCCAGGAAGAAATTAATGAGCAGGGACATGAGGTTCTCCGGGAGATGTTGCATA
          +---------+---------+---------+---------+---------+---------
          ACTCAGAGGTCCTTCTTTAATTACTCGTCCCTGTACTCCAAGAGGCCCTCTACAACGTAT
              S  L  Q  E  E  I  N  E  Q  G  H  E  V  L  R  E  M  L  H  N
           1580                  1600                    1620
                  .                     .                       .
          ACCACTCCTTCGTGGGCTGTGTGAATCCTCAGTGGGCCTTGGCACAGCATCAAACCAAGT
          +---------+---------+---------+---------+---------+---------
          TGGTGAGGAAGCACCCGACACACTTAGGAGTCACCCGGAACCGTGTCGTAGTTTGGTTCA
              H  S  F  V  G  C  V  N  P  Q  W  A  L  A  Q  H  Q  T  K  L
```

FIG. 1D

```
1640                1660                1680
  .         .         .         .         .         .
TATACCTTCTCAACACCACCAAGCTTAGTGAAGAACTGTTCTACCAGATACTCATTTATG
+---------+---------+---------+---------+---------+---------+
ATATGGAAGAGTTGTGGTGGTTCGAATCACTTCTTGACAAGATGGTCTATGAGTAAATAC
   Y  L  L  N  T  T  K  L  S  E  E  L  F  Y  Q  I  L  I  Y  D
1700                1720                1740
  .         .         .         .         .         .
ATTTTGCCAATTTTGGTGTTCTCAGGTTATCGGAGCCAGCACCGCTCTTTGACCTTGCCA
+---------+---------+---------+---------+---------+---------+
TAAAACGGTTAAAACCACAAGAGTCCAATAGCCTCGGTCGTGGCGAGAAACTGGAACGGT
   F  A  N  F  G  V  L  R  L  S  E  P  A  P  L  F  D  L  A  M
1760                1780                1800
  .         .         .         .         .         .
TGCTTGCCTTAGATAGTCCAGAGAGTGGCTGGACAGAGGAAGATGGTCCCAAAGAAGGAC
+---------+---------+---------+---------+---------+---------+
ACGAACGGAATCTATCAGGTCTCTCACCGACCTGTCTCCTTCTACCAGGGTTTCTTCCTG
   L  A  L  D  S  P  E  S  G  W  T  E  E  D  G  P  K  E  G  L
1820                1840                1860
  .         .         .         .         .         .
TTGCTGAATACATTGTTGAGTTTCTGAAGAAGAAGGCTGAGATGCTTGCAGACTATTTCT
+---------+---------+---------+---------+---------+---------+
AACGACTTATGTAACAACTCAAAGACTTCTTCTTCCGACTCTACGAACGTCTGATAAAGA
   A  E  Y  I  V  E  F  L  K  K  K  A  E  M  L  A  D  Y  F  S
1880                1900                1920
  .         .         .         .         .         .
CTTTGGAAATTGATGAGGAAGGGAACCTGATTGGATTACCCCTTCTGATTGACAACTATG
+---------+---------+---------+---------+---------+---------+
GAAACCTTTAACTACTCCTTCCCTTGGACTAACCTAATGGGGAAGACTAACTGTTGATAC
   L  E  I  D  E  E  G  N  L  I  G  L  P  L  L  I  D  N  Y  V
1940                1960                1980
  .         .         .         .         .         .
TGCCCCCTTTGGAGGGACTGCCTATCTTCATTCTTCGACTAGCCACTGAGGTGAATTGGG
----------+---------+---------+---------+---------+---------+
ACGGGGGAAACCTCCCTGACGGATAGAAGTAAGAAGCTGATCGGTGACTCCACTTAACCC
   P  P  L  E  G  L  P  I  F  I  L  R  L  A  T  E  V  N  W  D
2000                2020                2040
  .         .         .         .         .         .
ACGAAGAAAAGGAATGTTTTGAAAGCCTCAGTAAAGAATGCGCTATGTTCTATTCCATCC
+---------+---------+---------+---------+---------+---------+
TGCTTCTTTTCCTTACAAAACTTTCGGAGTCATTTCTTACGCGATACAAGATAAGGTAGG
   E  E  K  E  C  F  E  S  L  S  K  E  C  A  M  F  Y  S  I  R
```

FIG. 1E

```
         2060                2080                2100
            .                   .                   .
            .                   .                   .
GGAAGCAGTACATATCTGAGGAGTCGACCCTCTCAGGCCAGCAGAGTGAAGTGCCTGGCT
+---------+---------+---------+---------+---------+---------
CCTTCGTCATGTATAGACTCCTCAGCTGGGAGAGTCCGGTCGTCTCACTTCACGGACCGA
   K  Q  Y  I  S  E  E  S  T  L  S  G  Q  Q  S  E  V  P  G  S
         2120                2140                2160
            .                   .                   .
            .                   .                   .
CCATTCCAAACTCCTGGAAGTGGACTGTGGAACACATTGTCTATAAAGCCTTGCGCTCAC
+---------+---------+---------+---------+---------+---------
GGTAAGGTTTGAGGACCTTCACCTGACACCTTGTGTAACAGATATTTCGGAACGCGAGTG
    I  P  N  S  W  K  W  T  V  E  H  I  V  Y  K  A  L  R  S  H
         2180                2200                2220
            .                   .                   .
            .                   .                   .
ACATTCTGCCTCCTAAACATTTCACAGAAGATGGAAATATCCTGCAGCTTGCTAACCTGC
+---------+---------+---------+---------+---------+---------
TGTAAGACGGAGGATTTGTAAAGTGTCTTCTACCTTTATAGGACGTCGAACGATTGGACG
    I  L  P  P  K  H  F  T  E  D  G  N  I  L  Q  L  A  N  L  P
         2240                2260                2280
            .                   .                   .
            .                   .                   .
CTGATCTATACAAAGTCTTTGAGAGGTGTTAAATATGGTTATTTATGCACTGTGGGATGT
+---------+---------+---------+---------+---------+---------
GACTAGATATGTTTCAGAAACTCTCCACAATTTATACCAATAAATACGTGACACCCTACA
    D  L  Y  K  V  F  E  R  C  *
         2300                2320                2340
            .                   .                   .
            .                   .                   .
GTTCTTCTTTCTCTGTATTCCGATACAAAGTGTTGTATCAAAGTGTGATATACAAAGTGT
+---------+---------+---------+---------+---------+---------
CAAGAAGAAAGAGACATAAGGCTATGTTTCACAACATAGTTTCACACTATATGTTTCACA
         2360                2380                2400
            .                   .                   .
            .                   .                   .
ACCAACATAAGTGTTGGTAGCACTTAAGACTTATACTTGCCTTCTGATAGTATTCCTTTA
+---------+---------+---------+---------+---------+---------
TGGTTGTATTCACAACCATCGTGAATTCTGAATATGAACGGAAGACTATCATAAGGAAAT
         2420                2440                2460
            .                   .                   .
            .                   .                   .
TACACAGTGGATTGATTATAAATAAATAGATGTGTCTTAACATAAAAAAAAAAAAAAAAA
+---------+---------+---------+---------+---------+---------
ATGTGTCACCTAACTAATATTTATTTATCTACACAGAATTGTATTTTTTTTTTTTTTTTT

2480
   .
   .
AAAAA
+----
TTTTT
```

FIG. 1F

Polynucleotide and deduced amino acid sequence of hMLH2

```
         -70                    -50                   -30
          .                      .                     .
GGCACGAGTGGCTGCTTGCGGCTAGTGGATGGTAATTGCCTGCCTCGCGCTAGCAGCAAG
---------+---------+---------+---------+---------+---------+
CCGTGCTCACCGACGAACGCCGATCACCTACCATTAACGGACGGAGCGCGATCGTCGTTC
         -10                    10                    30
          .                      .                     .
CTGCTCTGTTAAAAGCGAAAATGAAACAATTGCCTGCGGCAACAGTTCGACTCCTTTCAA
---------+---------+---------+---------+---------+---------+
GACGAGACAATTTTCGCTTTTACTTTGTTAACGGACGCCGTTGTCAAGCTGAGGAAAGTT
                       M  K  Q  L  P  A  A  T  V  R  L  L  S  S
          50                    70                    90
          .                      .                     .
GTTCTCAGATCATCACTTCGGTGGTCAGTGTTGTAAAAGAGCTTATTGAAAACTCCTTGG
---------+---------+---------+---------+---------+---------+
CAAGAGTCTAGTAGTGAAGCCACCAGTCACAACATTTTCTCGAATAACTTTTGAGGAACC
  S  Q  I  I  T  S  V  V  S  V  V  K  E  L  I  E  N  S  L  D
         110                   130                   150
          .                      .                     .
ATGCTGGTGCCACAAGCGTAGATGTTAAACTGGAGAACTATGGATTTGATAAAATTGAGG
---------+---------+---------+---------+---------+---------+
TACGACCACGGTGTTCGCATCTACAATTTGACCTCTTGATACCTAAACTATTTTAACTCC
  A  G  A  T  S  V  D  V  K  L  E  N  Y  G  F  D  K  I  E  V
         170                   190                   210
          .                      .                     .
TGCGAGATAACGGGGAGGGTATCAAGGCTGTTGATGCACCTGTAATGGCAATGAAGTACT
---------+---------+---------+---------+---------+---------+
ACGCTCTATTGCCCCTCCCATAGTTCCGACAACTACGTGGACATTACCGTTACTTCATGA
  R  D  N  G  E  G  I  K  A  V  D  A  P  V  M  A  M  K  Y  Y
         230                   250                   270
          .                      .                     .
ACACCTCAAAAATAAATAGTCATGAAGATCTTGAAAATTTGACAACTTACGGTTTTCGTG
---------+---------+---------+---------+---------+---------+
TGTGGAGTTTTTATTTATCAGTACTTCTAGAACTTTTAAACTGTTGAATGCCAAAAGCAC
  T  S  K  I  N  S  H  E  D  L  E  N  L  T  T  Y  G  F  R  G
         290                   310                   330
          .                      .                     .
GAGAAGCCTTGGGGTCAATTTGTTGTATAGCTGAGGTTTTAATTACAACAAGAACGGCTG
---------+---------+---------+---------+---------+---------+
CTCTTCGGAACCCCAGTTAAACAACATATCGACTCCAAAATTAATGTTGTTCTTGCCGAC
  E  A  L  G  S  I  C  C  I  A  E  V  L  I  T  T  R  T  A  A
```

FIG. 2A

```
              350                 370                  390
               .                   .                    .
    CTGATAATTTTAGCACCCAGTATGTTTTAGATGGCAGTGGCCACATACTTTCTCAGAAAC
    ---------+---------+---------+---------+---------+---------+
    GACTATTAAAATCGTGGGTCATACAAAATCTACCGTCACCGGTGTATGAAAGAGTCTTTG
      D  N  F  S  T  Q  Y  V  L  D  G  S  G  H  I  L  S  Q  K  P
               410                 430                  450
                .                   .                    .
    CTTCACATCTTGGTCAAGGTACAACTGTAACTGCTTTAAGATTATTTAAGAATCTACCTG
    ---------+---------+---------+---------+---------+---------+
    GAAGTGTAGAACCAGTTCCATGTTGACATTGACGAAATTCTAATAAATTCTTAGATGGAC
      S  H  L  G  Q  G  T  T  V  T  A  L  R  L  F  K  N  L  P  V
               470                 490                  510
                .                   .                    .
    TAAGAAAGCAGTTTTACTCAACTGCAAAAAAATGTAAAGATGAAATAAAAAAGATCCAAG
    ---------+---------+---------+---------+---------+---------+
    ATTCTTTCGTCAAAATGAGTTGACGTTTTTTTACATTTCTACTTTATTTTTTCTAGGTTC
      R  K  Q  F  Y  S  T  A  K  K  C  K  D  E  I  K  K  I  Q  D
               530                 550                  570
                .                   .                    .
    ATCTCCTCATGAGCTTTGGTATCCTTAAACCTGACTTAAGGATTGTCTTTGTACATAACA
    ---------+---------+---------+---------+---------+---------+
    TAGAGGAGTACTCGAAACCATAGGAATTTGGACTGAATTCCTAACAGAAACATGTATTGT
      L  L  M  S  F  G  I  L  K  P  D  L  R  I  V  F  V  H  N  K
               590                 610                  630
                .                   .                    .
    AGGCAGTTATTTGGCAGAAAAGCAGAGTATCAGATCACAAGATGGCTCTCATGTCAGTTC
    ---------+---------+---------+---------+---------+---------+
    TCCGTCAATAAACCGTCTTTTCGTCTCATAGTCTAGTGTTCTACCGAGAGTACAGTCAAG
      A  V  I  W  Q  K  S  R  V  S  D  H  K  M  A  L  M  S  V  L
               650                 670                  690
                .                   .                    .
    TGGGGACTGCTGTTATGAACAATATGGAATCCTTTCAGTACCACTCTGAAGAATCTCAGA
    ---------+---------+---------+---------+---------+---------+
    ACCCCTGACGACAATACTTGTTATACCTTAGGAAAGTCATGGTGAGACTTCTTAGAGTCT
      G  T  A  V  M  N  N  M  E  S  F  Q  Y  H  S  E  E  S  Q  I
               710                 730                  750
                .                   .                    .
    TTTATCTCAGTGGATTTCTTCCAAAGTGTGATGCAGACCACTCTTTCACTAGTCTTTCAA
    ---------+---------+---------+---------+---------+---------+
    AAATAGAGTCACCTAAAGAAGGTTTCACACTACGTCTGGTGAGAAAGTGATCAGAAAGTT
      Y  L  S  G  F  L  P  K  C  D  A  D  H  S  F  T  S  L  S  T
```

FIG. 2B

```
                770                 790                 810
                 .                   .                   .
CACCAGAAAGAAGTTTCATCTTCATAAACAGTCGACCAGTACATCAAAAAGATATCTTAA
---------+---------+---------+---------+---------+---------+
GTGGTCTTTCTTCAAAGTAGAAGTATTTGTCAGCTGGTCATGTAGTTTTTCTATAGAATT
   P  E  R  S  F  I  F  I  N  S  R  P  V  H  Q  K  D  I  L  K
             830                 850                 870

AGTTAATCCGACATCATTACAATCTGAAATGCCTAAAGGAATCTACTCGTTTGTATCCTG
---------+---------+---------+---------+---------+---------+
TCAATTAGGCTGTAGTAATGTTAGACTTTACGGATTTCCTTAGATGAGCAAACATAGGAC
   L  I  R  H  H  Y  N  L  K  C  L  K  E  S  T  R  L  Y  P  V
             890                 910                 930

TTTTCTTTCTGAAAATCGATGTTCCTACAGCTGATGTTGATGTAAATTTAACACCAGATA
---------+---------+---------+---------+---------+---------+
AAAAGAAAGACTTTTAGCTACAAGGATGTCGACTACAACTACATTTAAATTGTGGTCTAT
   F  F  L  K  I  D  V  P  T  A  D  V  D  V  N  L  T  P  D  K
             950                 970                 990

AAAGCCAAGTATTATTACAAAATAAGGAATCTGTTTTAATTGCTCTTGAAAATCTGATGA
---------+---------+---------+---------+---------+---------+
TTTCGGTTCATAATAATGTTTTATTCCTTAGACAAAATTAACGAGAACTTTTAGACTACT
   S  Q  V  L  L  Q  N  K  E  S  V  L  I  A  L  E  N  L  M  T
            1010                1030                1050

CGACTTGTTATGGACCATTACCTAGTACAAATTCTTATGAAAATAATAAAACAGATGTTT
---------+---------+---------+---------+---------+---------+
GCTGAACAATACCTGGTAATGGATCATGTTTAAGAATACTTTTATTATTTTGTCTACAAA
   T  C  Y  G  P  L  P  S  T  N  S  Y  E  N  N  K  T  D  V  S
            1070                1090                1110

CCGCAGCTGACATCGTTCTTAGTAAAACAGCAGAAACAGATGTGCTTTTTAATAAAGTGG
---------+---------+---------+---------+---------+---------+
GGCGTCGACTGTAGCAAGAATCATTTTGTCGTCTTTGTCTACACGAAAAATTATTTCACC
   A  A  D  I  V  L  S  K  T  A  E  T  D  V  L  F  N  K  V  E
            1130                1150                1170

AATCATCTGGAAAGAATTATTCAAATGTTGATACTTCAGTCATTCCATTCCAAAATGATA
---------+---------+---------+---------+---------+---------+
TTAGTAGACCTTTCTTAATAAGTTTACAACTATGAAGTCAGTAAGGTAAGGTTTTACTAT
   S  S  G  K  N  Y  S  N  V  D  T  S  V  I  P  F  Q  N  D  M
```

FIG. 2C

```
                  1190                1210                1230
                    .                  .                   .
          TGCATAATGATGAATCTGGAAAAAACACTGATGATTGTTTAAATCACCAGATAAGTATTG
          ---------+---------+---------+---------+---------+---------+
          ACGTATTACTACTTAGACCTTTTTTGTGACTACTAACAAATTTAGTGGTCTATTCATAAC
           H  N  D  E  S  G  K  N  T  D  D  C  L  N  H  Q  I  S  I  G
                  1250                1270                1290
                    .                  .                   .
          GTGACTTTGGTTATGGTCATTGTAGTAGTGAAATTTCTAACATTGATAAAAACACTAAGA
          ---------+---------+---------+---------+---------+---------+
          CACTGAAACCAATACCAGTAACATCATCACTTTAAAGATTGTAACTATTTTTGTGATTCT
           D  F  G  Y  G  H  C  S  S  E  I  S  N  I  D  K  N  T  K  N
                  1310                1330                1350
                    .                  .                   .
          ATGCATTTCAGGACATTTCAATGAGTAATGTATCATGGGAGAACTCTCAGACGGAATATA
          ---------+---------+---------+---------+---------+---------+
          TACGTAAAGTCCTGTAAAGTTACTCATTACATAGTACCCTCTTGAGAGTCTGCCTTATAT
           A  F  Q  D  I  S  M  S  N  V  S  W  E  N  S  Q  T  E  Y  S
                  1370                1390                1410
                    .                  .                   .
          GTAAAACTTGTTTTATAAGTTCCGTTAAGCACACCCAGTCAGAAAATGGCAATAAAGACC
          ---------+---------+---------+---------+---------+---------+
          CATTTTGAACAAAATATTCAAGGCAATTCGTGTGGGTCAGTCTTTTACCGTTATTTCTGG
           K  T  C  F  I  S  S  V  K  H  T  Q  S  E  N  G  N  K  D  H
                  1430                1450                1470
                    .                  .                   .
          ATATAGATGAGAGTGGGGAAAATGAGGAAGAAGCAGGTCTTGAAAACTCTTCGGAAATTT
          ---------+---------+---------+---------+---------+---------+
          TATATCTACTCTCACCCCTTTTACTCCTTCTTCGTCCAGAACTTTTGAGAAGCCTTTAAA
           I  D  E  S  G  E  N  E  E  E  A  G  L  E  N  S  S  E  I  S
                  1490                1510                1530
                    .                  .                   .
          CTGCAGATGAGTGGAGCAGGGGAAATATACTTAAAAATTCAGTGGGAGAGAATATTGAAC
          ---------+---------+---------+---------+---------+---------+
          GACGTCTACTCACCTCGTCCCCTTTATATGAATTTTTAAGTCACCCTCTCTTATAACTTG
           A  D  E  W  S  R  G  N  I  L  K  N  S  V  G  E  N  I  E  P
                  1550                1570                1590
                    .                  .                   .
          CTGTGAAAATTTTAGTGCCTGAAAAAGTTTACCATGTAAAGTAAGTAATAATAATTATC
          ---------+---------+---------+---------+---------+---------+
          GACACTTTTAAAATCACGGACTTTTTTCAAATGGTACATTTCATTCATTATTATTAATAG
           V  K  I  L  V  P  E  K  S  L  P  C  K  V  S  N  N  N  Y  P
```

FIG. 2D

```
                1610                  1630                 1650
                  .                    .                    .
      CAATCCCTGAACAAATGAATCTTAATGAAGATTCATGTAACAAAAAATCAAATGTAATAG
      ---------+---------+---------+---------+---------+---------+
      GTTAGGGACTTGTTTACTTAGAATTACTTCTAAGTACATTGTTTTTAGTTTACATTATC
         I  P  E  Q  M  N  L  N  E  D  S  C  N  K  K  S  N  V  I  D
                1670                  1690                 1710
                  .                    .                    .
      ATAATAAATCTGGAAAAGTTACAGCTTATGATTTACTTAGCAATCGAGTAATCAAGAAAC
      ---------+---------+---------+---------+---------+---------+
      TATTATTTAGACCTTTTCAATGTCGAATACTAAATGAATCGTTAGCTCATTAGTTCTTTG
         N  K  S  G  K  V  T  A  Y  D  L  L  S  N  R  V  I  K  K  P
                1730                  1750                 1770
                  .                    .                    .
      CCATGTCAGCAAGTGCTCTTTTTGTTCAAGATCATCGTCCTCAGTTTCTCATAGAAAATC
      ---------+---------+---------+---------+---------+---------+
      GGTACAGTCGTTCACGAGAAAAACAAGTTCTAGTAGCAGGAGTCAAAGAGTATCTTTTAG
         M  S  A  S  A  L  F  V  Q  D  H  R  P  Q  F  L  I  E  N  P
                1790                  1810                 1830
                  .                    .                    .
      CTAAGACTAGTTTAGAGGATGCAACACTACAAATTGAAGAACTGTGGAAGACATTGAGTG
      ---------+---------+---------+---------+---------+---------+
      GATTCTGATCAAATCTCCTACGTTGTGATGTTTAACTTCTTGACACCTTCTGTAACTCAC
         K  T  S  L  E  D  A  T  L  Q  I  E  E  L  W  K  T  L  S  E
                1850                  1870                 1890
                  .                    .                    .
      AAGAGGAAAAACTGAAATATGAAGAGAAGGCTACTAAAGACTTGGAACGATACAATAGTC
      ---------+---------+---------+---------+---------+---------+
      TTCTCCTTTTTGACTTTATACTTCTCTTCCGATGATTTCTGAACCTTGCTATGTTATCAG
         E  E  K  L  K  Y  E  E  K  A  T  K  D  L  E  R  Y  N  S  Q
                1910                  1930                 1950
                  .                    .                    .
      AAATGAAGAGAGCCATTGAACAGGAGTCACAAATGTCACTAAAAGATGGCAGAAAAAAGA
      ---------+---------+---------+---------+---------+---------+
      TTTACTTCTCTCGGTAACTTGTCCTCAGTGTTTACAGTGATTTTCTACCGTCTTTTTTCT
         M  K  R  A  I  E  Q  E  S  Q  M  S  L  K  D  G  R  K  K  I
                1970                  1990                 2010
                  .                    .                    .
      TAAAACCCACCAGCGCATGGAATTTGGCCCAGAAGCACAAGTTAAAAACCTCATTATCTA
      ---------+---------+---------+---------+---------+---------+
      ATTTTGGGTGGTCGCGTACCTTAAACCGGGTCTTCGTGTTCAATTTTTGGAGTAATAGAT
         K  P  T  S  A  W  N  L  A  Q  K  H  K  L  K  T  S  L  S  N
```

FIG. 2E

```
                  2030                      2050                      2070
ATCAACCAAAACTTGATGAACTCCTTCAGTCCCAAATTGAAAAAGAAGGAGTCAAAATA
---------+---------+---------+---------+---------+---------+
TAGTTGGTTTTGAACTACTTGAGGAAGTCAGGGTTTAACTTTTTCTTCCTCAGTTTTAT
    Q  P  K  L  D  E  L  L  Q  S  Q  I  E  K  R  R  S  Q  N  I
                  2090                      2110                      2130
                   .                         .                         .
TTAAAATGGTACAGATCCCCTTTTCTATGAAAAACTTAAAAATAAATTTTAAGAAACAAA
---------+---------+---------+---------+---------+---------+
AATTTTACCATGTCTAGGGGAAAAGATACTTTTTGAATTTTTATTTAAAATTCTTTGTTT
    K  M  V  Q  I  P  F  S  M  K  N  L  K  I  N  F  K  K  Q  N
                  2150                      2170                      2190
                   .                         .                         .
ACAAAGTTGACTTAGAAGAGAAGGATGAACCTTGCTTGATCCACAATCTCAGGTTTCCTG
---------+---------+---------+---------+---------+---------+
TGTTTCAACTGAATCTTCTCTTCCTACTTGGAACGAACTAGGTGTTAGAGTCCAAAGGAC
   K  V  D  L  E  E  K  D  E  P  C  L  I  H  N  L  R  F  P  D
             2210                      2230                      2250
                   .                         .                         .
ATGCATGGCTAATGACATCCAAAACAGAGGTAATGTTATTAAATCCATATAGAGTAGAAG
---------+---------+---------+---------+---------+---------+
TACGTACCGATTACTGTAGGTTTTGTCTCCATTACAATAATTTAGGTATATCTCATCTTC
   A  W  L  M  T  S  K  T  E  V  M  L  L  N  P  Y  R  V  E  E
             2270                      2290                      2310
                   .                         .                         .
AAGCCCTGCTATTTAAAAGACTTCTTGAGAATCATAAACTTCCTGCAGAGCCACTGGAAA
---------+---------+---------+---------+---------+---------+
TTCGGGACGATAAATTTTCTGAAGAACTCTTAGTATTTGAAGGACGTCTCGGTGACCTTT
    A  L  L  F  K  R  L  L  E  N  H  K  L  P  A  E  P  L  E  K
             2330                      2350                      2370
                   .                         .                         .
AGCCAATTATGTTAACAGAGAGTCTTTTTAATGGATCTCATTATTTAGACGTTTTATATA
---------+---------+---------+---------+---------+---------+
TCGGTTAATACAATTGTCTCTCAGAAAAATTACCTAGAGTAATAAATCTGCAAAATATAT
     P  I  M  L  T  E  S  L  F  N  G  S  H  Y  L  D  V  L  Y  K
             2390                      2410                      2430
                   .                         .                         .
AAATGACAGCAGATGACCAAAGATACAGTGGATCAACTTACCTGTCTGATCCTCGTCTTA
---------+---------+---------+---------+---------+---------+
TTTACTGTCGTCTACTGGTTTCTATGTCACCTAGTTGAATGGACAGACTAGGAGCAGAAT
       M  T  A  D  D  Q  R  Y  S  G  S  T  Y  L  S  D  P  R  L  T
```

FIG. 2F

```
                2450                    2470                   2490
                 .                       .                      .
     CAGCGAATGGTTTCAAGATAAAATTGATACCAGGAGTTTCAATTACTGAAAATTACTTGG
     ---------+---------+---------+---------+---------+---------+
     GTCGCTTACCAAAGTTCTATTTTAACTATGGTCCTCAAAGTTAATGACTTTTAATGAACC
       A  N  G  F  K  I  K  L  I  P  G  V  S  I  T  E  N  Y  L  E
                2510                    2530                   2550
                 .                       .                      .
     AAATAGAAGGAATGGCTAATTGTCTCCCATTCTATGGAGTAGCAGATTTAAAAGAAATTC
     ---------+---------+---------+---------+---------+---------+
     TTTATCTTCCTTACCGATTAACAGAGGGTAAGATACCTCATCGTCTAAATTTTCTTTAAG
       I  E  G  M  A  N  C  L  P  F  Y  G  V  A  D  L  K  E  I  L
                2570                    2590                   2610
                 .                       .                      .
     TTAATGCTATATTAAACAGAAATGCAAAGGAAGTTTATGAATGTAGACCTCGCAAAGTGA
     ---------+---------+---------+---------+---------+---------+
     AATTACGATATAATTTGTCTTTACGTTTCCTTCAAATACTTACATCTGGAGCGTTTCACT
       N  A  I  L  N  R  N  A  K  E  V  Y  E  C  R  P  R  K  V  I
                2630                    2650                   2670
                 .                       .                      .
     TAAGTTATTTAGAGGGAGAAGCAGTGCGTCTATCCAGACAATTACCCATGTACTTATCAA
     ---------+---------+---------+---------+---------+---------+
     ATTCAATAAATCTCCCTCTTCGTCACGCAGATAGGTCTGTTAATGGGTACATGAATAGTT
       S  Y  L  E  G  E  A  V  R  L  S  R  Q  L  P  M  Y  L  S  K
                2690                    2710                   2730
                 .                       .                      .
     AAGAGGACATCCAAGACATTATCTACAGAATGAAGCACCAGTTTGGAAATGAAATTAAAG
     ---------+---------+---------+---------+---------+---------+
     TTCTCCTGTAGGTTCTGTAATAGATGTCTTACTTCGTGGTCAAACCTTTACTTTAATTTC
       E  D  I  Q  D  I  I  Y  R  M  K  H  Q  F  G  N  E  I  K  E
                2750                    2770                   2790
                 .                       .                      .
     AGTGTGTTCATGGTCGCCCATTTTTTCATCATTTAACCTATCTTCCAGAAACTACATGAT
     ---------+---------+---------+---------+---------+---------+
     TCACACAAGTACCAGCGGGTAAAAAAGTAGTAAATTGGATAGAAGGTCTTTGATGTACTA
       C  V  H  G  R  P  F  F  H  H  L  T  Y  L  P  E  T  T  *
                2810                    2830                   2850
                 .                       .                      .
     TAAATATGTTTAAGAAGATTAGTTACCATTGAAATTGGTTCTGTCATAAAACAGCATGAG
     ---------+---------+---------+---------+---------+---------+
     ATTTATACAAATTCTTCTAATCAATGGTAACTTTAACCAAGACAGTATTTTGTCGTACTC
```

FIG. 2G

```
                    2870                2890                2910
                      .                   .                   .
                 .          .         .           .        .           .
          TCTGGTTTTAAATTATCTTTGTATTATGTGTCACATGGTTATTTTTTAAATGAGGATTCA
          ---------+---------+---------+---------+---------+---------+
          AGACCAAAATTTAATAGAAACATAATACACAGTGTACCAATAAAAAATTTACTCCTAAGT
                    2930                2950                2970
                      .                   .                   .
                 .          .         .           .        .           .
          CTGACTTGTTTTTATATTGAAAAAGTTCCACGTATTGTAGAAAACGTAAATAAACTAAT
          ---------+---------+---------+---------+---------+---------+
          GACTGAACAAAAATATAACTTTTTTCAAGGTGCATAACATCTTTTGCATTTATTTGATTA

AAC
          ---
          TTG
```

FIG. 2H

Polynucleotide and deduced amino acid sequence of hMLH3

```
     -20                 0                   20
       .                 .                   .
CGAGGCGGATCGGGTGTTGCATCCATGGAGCGAGCTGAGAGCTCGAGTACAGAACCTGCT
---+---------+---------+---------+---------+---------+------
GCTCCGCCTAGCCCACAACGTAGGTACCTCGCTCGACTCTCGAGCTCATGTCTTGGACGA
                         M  E  R  A  E  S  S  S  T  E  P  A
      40                60                  80
       .                 .                   .
AAGGCCATCAAACCTATTGATCGGAAGTCAGTCCATCAGATTTGCTCTGGGCAGGTGGTA
---+---------+---------+---------+---------+---------+------
TTCCGGTAGTTTGGATAACTAGCCTTCAGTCAGGTAGTCTAAACGAGACCCGTCCACCAT
 K  A  I  K  P  I  D  R  K  S  V  H  Q  I  C  S  G  Q  V  V
     100               120                 140
       .                 .                   .
CTGAGTCTAAGCACTGCGGTAAAGGAGTTAGTAGAAAACAGTCTGGATGCTGGTGCCACT
---+---------+---------+---------+---------+---------+------
GACTCAGATTCGTGACGCCATTTCCTCAATCATCTTTTGTCAGACCTACGACCACGGTGA
 L  S  L  S  T  A  V  K  E  L  V  E  N  S  L  D  A  G  A  T
     160               180                 200
       .                 .                   .
AATATTGATCTAAAGCTTAAGGACTATGGAGTGGATCTTATTGAAGTTTCAGACAATGGA
---+---------+---------+---------+---------+---------+------
TTATAACTAGATTTCGAATTCCTGATACCTCACCTAGAATAACTTCAAAGTCTGTTACCT
 N  I  D  L  K  L  K  D  Y  G  V  D  L  I  E  V  S  D  N  G
     220               240                 260
       .                 .                   .
TGTGGGGTAGAAGAAGAAAACTTCGAAGGCTTAACTCTGAAACATCACACATCTAAGATT
---+---------+---------+---------+---------+---------+------
ACACCCCATCTTCTTCTTTTGAAGCTTCCGAATTGAGACTTTGTAGTGTGTAGATTCTAA
 C  G  V  E  E  E  N  F  E  G  L  T  L  K  H  H  T  S  K  I
     280               300                 320
       .                 .                   .
CAAGAGTTTGCCGACCTAACTCAGGTTGAAACTTTTGGCTTTCGGGGGGAAGCTCTGAGC
---+---------+---------+---------+---------+---------+------
GTTCTCAAACGGCTGGATTGAGTCCAACTTTGAAAACCGAAAGCCCCCCTTCGAGACTCG
 Q  E  F  A  D  L  T  Q  V  E  T  F  G  F  R  G  E  A  L  S
     340               360                 380
       .                 .                   .
TCACTTTGTGCACTGAGCGATGTCACCATTTCTACCTGCCACGCATCGGCGAAGGTTGGA
---+---------+---------+---------+---------+---------+------
AGTGAAACACGTGACTCGCTACAGTGGTAAAGATGGACGGTGCGTAGCCGCTTCCAACCT
 S  L  C  A  L  S  D  V  T  I  S  T  C  H  A  S  A  K  V  G
```

FIG. 3A

```
                400                   420                    440
                 .                     .                      .
         ACTCGACTGATGTTTGATCACAATGGGAAAATTATCCAGAAAACCCCCTACCCCCGCCCC
         ---+----------+----------+----------+----------+----------+------
         TGAGCTGACTACAAACTAGTGTTACCCTTTTAATAGGTCTTTTGGGGGATGGGGGCGGGG
          T  R  L  M  F  D  H  N  G  K  I  I  Q  K  T  P  Y  P  R  P
                460                   480                    500
                 .                     .                      .
         AGAGGGACCACAGTCAGCGTGCAGCAGTTATTTTCCACACTACCTGTGCGCCATAAGGAA
         ---+----------+----------+----------+----------+----------+------
         TCTCCCTGGTGTCAGTCGCACGTCGTCAATAAAAGGTGTGATGGACACGCGGTATTCCTT
          R  G  T  T  V  S  V  Q  Q  L  F  S  T  L  P  V  R  H  K  E
                ·520                  540                    560
                 .                     .                      .
         TTTCAAAGGAATATTAAGAAGGAGTATGCCAAAATGGTCCAGGTCTTACATGCATACTGT
         ---+----------+----------+----------+----------+----------+------
         AAAGTTTCCTTATAATTCTTCCTCATACGGTTTTACCAGGTCCAGAATGTACGTATGACA
          F  Q  R  N  I  K  K  E  Y  A  K  M  V  Q  V  L  H  A  Y  C
                580                   600                    620
                 .                     .                      .
         ATCATTTCAGCAGGCATCCGTGTAAGTTGCACCAATCAGCTTGGACAAGGAAAACGACAG
         ---+----------+----------+----------+----------+----------+------
         TAGTAAAGTCGTCCGTAGGCACATTCAACGTGGTTAGTCGAACCTGTTCCTTTTGCTGTC
          I  I  S  A  G  I  R  V  S  C  T  N  Q  L  G  Q  G  K  R  Q
                640                   660                    680
                 .                     .                      .
         CCTGTGGTATGCACAGGTGGAAGCCCCAGCATAAAGGAAAATATCGGCTCTGTGTTTGGG
         ---+----------+----------+----------+----------+----------+------
         GGACACCATACGTGTCCACCTTCGGGGTCGTATTTCCTTTTATAGCCGAGACACAAACCC
          P  V  V  C  T  G  G  S  P  S  I  K  E  N  I  G  S  V  F  G
                700                   720                    740
                 .                     .                      .
         CAGAAGCAGTTGCAAAGCCTCATTCCTTTTGTTCAGCTGCCCCCTAGTGACTCCGTGTGT
         ---+----------+----------+----------+----------+----------+------
         GTCTTCGTCAACGTTTCGGAGTAAGGAAAACAAGTCGACGGGGGATCACTGAGGCACACA
          Q  K  Q  L  Q  S  L  I  P  F  V  Q  L  P  P  S  D  S  V  C
                760                   780                    800
                 .                     .                      .
         GAAGAGTACGGTTTGAGCTGTTCGGATGCTCTGCATAATCTTTTTTACATCTCAGGTTTC
         ---+----------+----------+----------+----------+----------+------
         CTTCTCATGCCAAACTCGACAAGCCTACGAGACGTATTAGAAAAAATGTAGAGTCCAAAG
          E  E  Y  G  L  S  C  S  D  A  L  H  N  L  F  Y  I  S  G  F
```

FIG. 3B

```
            820                 840                    860
              .                   .                      .
              .                   .                      .
ATTTCACAATGCACGCATGGAGTTGGAAGGAGTTCAACAGACAGACAGTTTTTCTTTATC
---+----------+----------+----------+----------+----------+------
TAAAGTGTTACGTGCGTACCTCAACCTTCCTCAAGTTGTCTGTCTGTCAAAAGAAATAG
 I  S  Q  C  T  H  G  V  G  R  S  S  T  D  R  Q  F  F  F  I
           880                 900                    920
```

```
              .                   .                      .
              .                   .                      .
AACCGGCGGCCTTGTGACCCAGCAAAGGTCTGCAGACTCGTGAATGAGGTCTACCACATG
---+----------+----------+----------+----------+----------+------
TTGGCCGCCGGAACACTGGGTCGTTTCCAGACGTCTGAGCACTTACTCCAGATGGTGTAC
 N  R  R  P  C  D  P  A  K  V  C  R  L  V  N  E  V  Y  H  M
           940                 960                    980
```

```
              .                   .                      .
              .                   .                      .
TATAATCGACACCAGTATCCATTTGTTGTTCTTAACATTTCTGTTGATTCAGAATGCGTT
---+----------+----------+----------+----------+----------+------
ATATTAGCTGTGGTCATAGGTAAACAACAAGAATTGTAAAGACAACTAAGTCTTACGCAA
 Y  N  R  H  Q  Y  P  F  V  V  L  N  I  S  V  D  S  E  C  V
          1000                1020                   1040
```

```
              .                   .                      .
              .                   .                      .
GATATCAATGTTACTCCAGATAAAAGGCAAATTTTGCTACAAGAGGAAAAGCTTTTGTTG
---+----------+----------+----------+----------+----------+------
CTATAGTTACAATGAGGTCTATTTTCCGTTTAAAACGATGTTCTCCTTTTCGAAAACAAC
 D  I  N  V  T  P  D  K  R  Q  I  L  L  Q  E  E  K  L  L  L
          1060                1080                   1100
```

```
              .                   .                      .
              .                   .                      .
GCAGTTTTAAAGACCTCTTTGATAGGAATGTTTGATAGTGATGTCAACAAGCTAAATGTC
---+----------+----------+----------+----------+----------+------
CGTCAAAATTTCTGGAGAAACTATCCTTACAAACTATCACTACAGTTGTTCGATTTACAG
 A  V  L  K  T  S  L  I  G  M  F  D  S  D  V  N  K  L  N  V
          1120                1140                   1160
```

```
              .                   .                      .
              .                   .                      .
AGTCAGCAGCCACTGCTGGATGTTGAAGGTAACTTAATAAAAATGCATGCAGCGGATTTG
---+----------+----------+----------+----------+----------+------
TCAGTCGTCGGTGACGACCTACAACTTCCATTGAATTATTTTTACGTACGTCGCCTAAAC
 S  Q  Q  P  L  L  D  V  E  G  N  L  I  K  M  H  A  A  D  L
          1180                1200                   1220
```

```
              .                   .                      .
              .                   .                      .
GAAAAGCCCATGGTAGAAAAGCAGGATCAATCCCCTTCATTAAGGACTGGAGAAGAAAAA
---+----------+----------+----------+----------+----------+------
CTTTTCGGGTACCATCTTTTCGTCCTAGTTAGGGGAAGTAATTCCTGACCTCTTCTTTTT
 E  K  P  M  V  E  K  Q  D  Q  S  P  S  L  R  T  G  E  E  K
```

FIG. 3C

```
                1240                1260                1280
                  .                   .                   .
        AAAGACGTGTCCATTTCCAGACTGCGAGAGGCCTTTTCTCTTCGTCACACAACAGAGAAC
        ---+---------+---------+---------+---------+---------+------
        TTTCTGCACAGGTAAAGGTCTGACGCTCTCCGGAAAAGAGAAGCAGTGTGTTGTCTCTTG
         K  D  V  S  I  S  R  L  R  E  A  F  S  L  R  H  T  T  E  N
              1300                1320                1340
                  .                   .                   .
        AAGCCTCACAGCCCAAAGACTCCAGAACCAAGAAGGAGCCCTCTAGGACAGAAAAGGGGT
        ---+---------+---------+---------+---------+---------+------
        TTCGGAGTGTCGGGTTTCTGAGGTCTTGGTTCTTCCTCGGGAGATCCTGTCTTTTCCCCA
         K  P  H  S  P  K  T  P  E  P  R  R  S  P  L  G  Q  K  R  G
              1360                1380                1400
                  .                   .                   .
        ATGCTGTCTTCTAGCACTTCAGGTGCCATCTCTGACAAAGGCGTCCTGAGACCTCAGAAA
        ---+---------+---------+---------+---------+---------+------
        TACGACAGAAGATCGTGAAGTCCACGGTAGAGACTGTTTCCGCAGGACTCTGGAGTCTTT
         M  L  S  S  S  T  S  G  A  I  S  D  K  G  V  L  R  P  Q  K
              1420                1440                1460
                  .                   .                   .
        GAGGCAGTGAGTTCCAGTCACGGACCCAGTGACCCTACGGACAGAGCGGAGGTGGAGAAG
        ---+---------+---------+---------+---------+---------+------
        CTCCGTCACTCAAGGTCAGTGCCTGGGTCACTGGGATGCCTGTCTCGCCTCCACCTCTTC
         E  A  V  S  S  S  H  G  P  S  D  P  T  D  R  A  E  V  E  K
              1480                1500                1520
                  .                   .                   .
        GACTCGGGGCACGGCAGCACTTCCGTGGATTCTGAGGGGTTCAGCATCCCAGACACGGGC
        ---+---------+---------+---------+---------+---------+------
        CTGAGCCCCGTGCCGTCGTGAAGGCACCTAAGACTCCCCAAGTCGTAGGGTCTGTGCCCG
         D  S  G  H  G  S  T  S  V  D  S  E  G  F  S  I  P  D  T  G
              1540                1560                1580
                  .                   .                   .
        AGTCACTGCAGCAGCGAGTATGCGGCCAGCTCCCCAGGGGACAGGGGCTCGCAGGAACAT
        ---+---------+---------+---------+---------+---------+------
        TCAGTGACGTCGTCGCTCATACGCCGGTCGAGGGGTCCCCTGTCCCCGAGCGTCCTTGTA
         S  H  C  S  S  E  Y  A  A  S  S  P  G  D  R  G  S  Q  E  H
              1600                1620                1640
                  .                   .                   .
        GTGGACTCTCAGGAGAAAGCGCCTGAAACTGACGACTCTTTTTCAGATGTGGACTGCCAT
        ---+---------+---------+---------+---------+---------+------
        CACCTGAGAGTCCTCTTTCGCGGACTTTGACTGCTGAGAAAAAGTCTACACCTGACGGTA
         V  D  S  Q  E  K  A  P  E  T  D  D  S  F  S  D  V  D  C  H
```

FIG. 3D

```
            1660               1680              1700
              .                  .                 .
     TCAAACCAGGAAGATACCGGATGTAAATTTCGAGTTTTGCCTCAGCCAACTAATCTCGCA
     ---+---------+---------+---------+---------+---------+------
     AGTTTGGTCCTTCTATGGCCTACATTTAAAGCTCAAAACGGAGTCGGTTGATTAGAGCGT
      S  N  Q  E  D  T  G  C  K  F  R  V  L  P  Q  P  T  N  L  A
            1720               1740              1760
              .                  .                 .
     ACCCCAAACACAAAGCGTTTTAAAAAAGAAGAAATTCTTTCCAGTTCTGACATTTGTCAA
     ---+---------+---------+---------+---------+---------+------
     TGGGGTTTGTGTTTCGCAAAATTTTTTCTTCTTTAAGAAAGGTCAAGACTGTAAACAGTT
      T  P  N  T  K  R  F  K  K  E  E  I  L  S  S  D  I  C  Q
            1780               1800              1820
              .                  .                 .
     AAGTTAGTAAATACTCAGGACATGTCAGCCTCTCAGGTTGATGTAGCTGTGAAAATTAAT
     ---+---------+---------+---------+---------+---------+------
     TTCAATCATTTATGAGTCCTGTACAGTCGGAGAGTCCAACTACATCGACACTTTTAATTA
      K  L  V  N  T  Q  D  M  S  A  S  Q  V  D  V  A  V  K  I  N
            1840               1860              1880
              .                  .                 .
     AAGAAAGTTGTGCCCCTGGACTTTTCTATGAGTTCTTTAGCTAAACGAATAAAGCAGTTA
     ---+---------+---------+---------+---------+---------+------
     TTCTTTCAACACGGGGACCTGAAAAGATACTCAAGAAATCGATTTGCTTATTTCGTCAAT
      K  K  V  V  P  L  D  F  S  M  S  S  L  A  K  R  I  K  Q  L
            1900               1920              1940
              .                  .                 .
     CATCATGAAGCACAGCAAAGTGAAGGGGAACAGAATTACAGGAAGTTTAGGGCAAAGATT
     ---+---------+---------+---------+---------+---------+------
     GTAGTACTTCGTGTCGTTTCACTTCCCCTTGTCTTAATGTCCTTCAAATCCCGTTTCTAA
      H  H  E  A  Q  Q  S  E  G  E  Q  N  Y  R  K  F  R  A  K  I
            1960               1980              2000
              .                  .                 .
     TGTCCTGGAGAAAATCAAGCAGCCGAAGATGAACTAAGAAAAGAGATAAGTAAAACGATG
     ---+---------+---------+---------+---------+---------+------
     ACAGGACCTCTTTTAGTTCGTCGGCTTCTACTTGATTCTTTTCTCTATTCATTTGCTAC
      C  P  G  E  N  Q  A  A  E  D  E  L  R  K  E  I  S  K  T  M
            2020               2040              2060
              .                  .                 .
     TTTGCAGAAATGGAAATCATTGGTCAGTTTAACCTGGGATTTATAATAACCAAACTGAAT
     ---+---------+---------+---------+---------+---------+------
     AAACGTCTTTACCTTTAGTAACCAGTCAAATTGGACCCTAAATATTATTGGTTTGACTTA
      F  A  E  M  E  I  I  G  Q  F  N  L  G  F  I  I  T  K  L  N
```

FIG. 3E

```
            2080                    2100                    2120
             .                       .                       .
             .                       .                       .
GAGGATATCTTCATAGTGGACCAGCATGCCACGGACGAGAAGTATAACTTCGAGATGCTG
---+---------+---------+---------+---------+---------+------
CTCCTATAGAAGTATCACCTGGTCGTACGGTGCCTGCTCTTCATATTGAAGCTCTACGAC
 E   D   I   F   I   V   D   Q   H   A   T   D   E   K   Y   N   F   E   M   L
      2140                    2160                    2180

CAGCAGCACACCGTGCTCCAGGGGCAGAGGCTCATAGCACCTCAGACTCTCAACTTAACT
---+---------+---------+---------+---------+---------+------
GTCGTCGTGTGGCACGAGGTCCCCGTCTCCGAGTATCGTGGAGTCTGAGAGTTGAATTGA
 Q   Q   H   T   V   L   Q   G   Q   R   L   I   A   P   Q   T   L   N   L   T
      2200                    2220                    2240

GCTGTTAATGAAGCTGTTCTGATAGAAAATCTGGAAATATTTAGAAAGAATGGCTTTGAT
---+---------+---------+---------+---------+---------+------
CGACAATTACTTCGACAAGACTATCTTTTAGACCTTTATAAATCTTTCTTACCGAAACTA
 A   V   N   E   A   V   L   I   E   N   L   E   I   F   R   K   N   G   F   D
      2260                    2280                    2300

TTTGTTATCGATGAAAATGCTCCAGTCACTGAAAGGGCTAAACTGATTTCCTTGCCAACT
---+---------+---------+---------+---------+---------+------
AAACAATAGCTACTTTTACGAGGTCAGTGACTTTCCCGATTTGACTAAAGGAACGGTTGA
 F   V   I   D   E   N   A   P   V   T   E   R   A   K   L   I   S   L   P   T
      2320                    2340                    2360

AGTAAAAACTGGACCTTCGGACCCCAGGACGTCGATGAACTGATCTTCATGCTGAGCGAC
---+---------+---------+---------+---------+---------+------
TCATTTTTGACCTGGAAGCCTGGGGTCCTGCAGCTACTTGACTAGAAGTACGACTCGCTG
 S   K   N   W   T   F   G   P   Q   D   V   D   E   L   I   F   M   L   S   D
      2380                    2400                    2420

AGCCCTGGGGTCATGTGCCGGCCTTCCCGAGTCAAGCAGATGTTTGCCTCCAGAGCCTGC
---+---------+---------+---------+---------+---------+------
TCGGGACCCCAGTACACGGCCGGAAGGGCTCAGTTCGTCTACAAACGGAGGTCTCGGACG
 S   P   G   V   M   C   R   P   S   R   V   K   Q   M   F   A   S   R   A   C
      2440                    2460                    2480

CGGAAGTCGGTGATGATTGGGACTGCTCTTAACACAAGCGAGATGAAGAAACTGATCACC
---+---------+---------+---------+---------+---------+------
GCCTTCAGCCACTACTAACCCTGACGAGAATTGTGTTCGCTCTACTTCTTTGACTAGTGG
 R   K   S   V   M   I   G   T   A   L   N   T   S   E   M   K   K   L   I   T
```

FIG. 3F

```
              2500                    2520                     2540
               .                       .                        .
           .       .        .       .         .       .         .
    CACATGGGGGAGATGGACCACCCCTGGAACTGTCCCCATGGAAGGCCAACCATGAGACAC
    ---+---------+---------+---------+---------+---------+------
    GTGTACCCCCTCTACCTGGTGGGGACCTTGACAGGGGTACCTTCCGGTTGGTACTCTGTG
     H   M   G   E   M   D   H   P   W   N   C   P   H   G   R   P   T   M   R   H
              2560                   2580                    2600
               .                       .                        .
           .       .        .       .         .       .         .
    ATCGCCAACCTGGGTGTCATTTCTCAGAACTGACCGTAGTCACTGTATGGAATAATTGGT
    ---+---------+---------+---------+---------+---------+------
    TAGCGGTTGGACCCACAGTAAAGAGTCTTGACTGGCATCAGTGACATACCTTATTAACCA
     I   A   N   L   G   V   I   S   Q   N   *
              2620                   2640                    2660
               .                       .                        .
           .       .        .       .         .       .         .
    TTTATCGCAGATTTTTATGTTTTGAAAGACAGAGTCTTCACTAACCTTTTTTGTTTTAAA
    ---+---------+---------+---------+---------+---------+------
    AAATAGCGTCTAAAAATACAAAACTTTCTGTCTCAGAAGTGATTGGAAAAAACAAAATTT
              2680                   2700                    2720
               .                       .                        .
           .       .        .       .         .       .         .
    ATGAAACCTGCTACTTAAAAAAAATACACATCACACCCATTTAAAAGTGATCTTGAGAAC
    ---+---------+---------+---------+---------+---------+------
    TACTTTGGACGATGAATTTTTTTATGTGTAGTGTGGGTAAATTTTCACTAGAACTCTTG
       2740
        .
        .
    CTTTTCAAACC
    ---+-------
    GAAAAGTTTGG
```

FIG. 3G

```
YPMS1  mfhhienllietekrckqkeqryipvkylfsmtqIHQINDIDVHRITSGQVITDLTTAVKELVDNSIDANANQIEIFKD
HMLH2  -------------------------------MKQLPAATVRLLSSSQIITSVVSVVKELIENSLDAGATSVDVKLEN
HMLH3  meraessstepaka-----------------IKPIDRKSVHQICSGQVVLSLSTAVKELVENSLDAGATNIDLKLKD YPMS1  YGLESIECSDNGDGIDPSNYEFLALKHYTSKIAKFQDVAKVQTLGFRGEALSSLCGIAKLSVITTTSPPK-ADKLEYDMV
HMLH2  YGFDKIEVRDNGEGIKAVDAPVMAMKYYTSKINSHEDLENLTTYGFRGEALGSICCIAEYLITTRTAADNFSTQYVLDGS
HMLH3  YGVDLIEVSDNGCGVEEENFEGLTLKHHTSKIQEFADLTQVETFGFRGEALSSLCALSDVTISTCHASAKVGTRLMFDHN YPMS1  GHITSKTTTSRNKGTTYLVSQLFHNLPVRQKEFSKTfkrgftkcltviqgyainaaikfswnitpkgkknlilstmrn
HMLH2  GHILSQKPSHLGQGTTVTALRLFKNLPVRKQFYSTAkkckdeikkigdllmsfgilkpdlrivfvhnkaviwqksrvsdh
HMLH3  GKIIQKTPYPRPRGTTVSVQQLFSTLPVRHKEFQRNikkeyakmvqvlhayclisagirvsctnqlgqgkrqpvvctggs YPMS1  ssmrknissvfgaggmrgleevdlvldlnpfknrmlgkytddpdfldldykirvkgyisqnsfgcgrNSKDRQFIYVNKR
HMLH2  kmalmsvlgtavmnnmesfqyhseesqiylsgflpkcdadhsftsl--------------------STPERSFIFINSR
HMLH3  psikenigsvfgqkqlgslipfvqlppsdsvceeyglscsdalhnlfyisgfisqcthgvgr-----SSTDRQFFFINRR
```

FIG. 4A

```
YPMS1   PVEYSTLLKCCNEVYKTFNNVQ---FPAVFLNIELPMSLIDVNVTPDKRVILLHNERAVIDIFKTTLSDYYNrqelalp
HMLH2   PVHQKDILKLIRHHYNLKCLKESTRLYPVFFLKIDVPTADVDVNLTPDKSQVLIQNKESVLIALENLMTTCYGplpstns
HMLH3   PCDPAKVCRLVNEVYHMYNRHQ---YPFVVLNISVDSECVDINVTPDKRQILLQEEKLLLAVLKTSLIGMFDsdvnkln YPMS1   krmcsqseqqaqkrlktevfddrsttthesdnenyhtarsesngsnhahfnsttgvidksngteltsvmdgnytnvtdvig
HMLH2   yennktdvsaadivlsktaetdvlfnkvessgknysnvdtsvipfqndmhndesgkntddclnhqisigdfgyghcssei
HMLH3   vsqqplldvegnlikmhaadlekpmvekqdqspslrtgeekkdvsisrlreafslrhttenkphspktpeprrsplgkkr YPMS1   secevsvsdssvvldegnsstptkklpsiktdsqnlsdlnlnnfsnpefqnitspdkarslekvveepvyfdidgekfqek
HMLH2   snidkntknafgdismsnvswensgteysktcfissvkhtgsengnkdhidesgeneeaglensseisadewsrgnilk
HMLH3   gmlsststsgaisdkgvlrpqkeavssshgpsdptdraevekdsghgstsvdsegfsipdtgshcsseyaasspgdrgsqe YPMS1   avlsqadglvfvdnechehtndcchgerrgstdteqddeadsiyaeiepveinvrtplknsrksiskdnyrslsdglthr
HMLH2   nsvgeniepvkilvpekslpckvsnnnypipeqmnlnedscnkksnvidnksgkvtaydllsnrvikkpmsasalfvqdh
HMLH3   hvdsqekapetddsfsdvdchsnqedtgckfrvlpqptnlatpntkrfkkeeilsssdicqklvntqdmsasqvdvavki
```

FIG. 4B

```
YPMS1  kfedeileynlstknfkeiskngkqmssiiskrkseageniiknkdeledfeggekyltltvskndfkkmevvgqfnlgf
HMLH2  rpqflienpktsledatlqieelwktlseeeklkyeekatkdlerynsqmkraiegesqmslkdgrkkikptsawnlaqk
HMLH3  nkkvvpldfsmsslakrikqlhheaqqsegeqnyrkfrakicpgengaaedelrkeisktmfaemeiigqfnlgfiitkl YPMS1  iivtrkvdnksdlfivdghasdekynfetlqavtvfksqkliipqpvelsvidelvvldnlpvfekngfklkideeefg
HMLH2  hklktslsnqpkldellqsqiekrrsqnikmvqipfsmknlkinfkkqnkvdleekdepclihnlrfpdawlmtsktevm
HMLH3  nedifivdqhatdekynfemlqqhtvlqgqrliapqtlnltavnleavlienleifrkngfdfvidenapvteraklislp YPMS1  srvkllslptskqtlfdlgdfnelihlikedgglrrdni----------------------------------------
HMLH2  llnpyrveeallfkrilenhklpaeplekpimiteslfngshyldvlykmtaddqrysgstylsdprltangfkikllpg
HMLH3  tsknwtfgpqdvdelifmlsdspgvmc----------------------------------------------------

YPMS1  ------------------------------------RCSKIRSMFAMRACRSSIMIGKPLNKKTMTRVVHNLs
HMLH2  vsitenyleiegmanclpfygvadlkeilnailnrnakevyecRPRKVISYLEGEAVRLSRQLPMYLSKEDIIYRMk
HMLH3  ------------------------------------RPSRVKQMFASRACRKSVMIGTALNTSEMKKLITHMg YPMS1  eldkpw--NCPHGRPTMRHLMEIrdwssfskdyei
HMLH2  hqfgneikECVHGRPFFHHLTYLpett-------
HMLH3  emdhpw--NCPHGRPTMRHIANLgvisqn------
```

FIG. 4C

HUMAN DNA MISMATCH REPAIR PROTEINS

This application is a continuation-in-part of application Ser. No. 08/294,312 filed Aug. 23, 1994, which is a continuation-in-part of application Ser. No. 08/210,143 filed Mar. 16, 1994, which is a continuation-in-part of application Ser. No. 08/187,757 filed Jan. 27, 1994; and this application is also a continuation-in-part of PCT/US95/01035, filed Jan. 25, 1995. This application claims benefit of priority under 35 U.S.C. §120 of the four aforementioned applications.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human homologs of the prokaryotic mutL4 gene and are hereinafter referred to as hMLH1, hMLH2 and hMLH3.

In both prokaryotes and eukaryotes, the DNA mismatch repair gene plays a prominent role in the correction of errors made during DNA replication and genetic recombination. The E. coli methyl-directed DNA mismatch repair system is the best understood DNA mismatch repair system to date. In E. coli, this repair pathway involves the products of the mutator genes mutS, mutL, mutH, and uvrD. Mutants of any one of these genes will reveal a mutator phenotype. MutS is a DNA mismatch-binding protein which initiates this repair process, uvrD is a DNA helicase and MutH is a latent endonuclease that incises at the unmethylated strands of a hemi-methylated GATC sequence. MutL protein is believed to recognize and bind to the mismatch-DNA-MutS-MutH complex to enhance the endonuclease activity of MutH protein. After the unmethylated DNA strand is cut by the MutH, single-stranded DNA-binding protein, DNA polymerase III, exonuclease I and DNA ligase are required to complete this repair process (Modrich P., Annu. Rev. Genetics, 25:229–53 (1991)).

Elements of the E. coli MutLHS system appears to be conserved during evolution in prokaryotes and eukaryotes. Genetic study analysis suggests that *Saccharomyces cerevisiae* has a mismatch repair system similar to the bacterial MutLHS system. In S. cerevisiae, at least two MutL homologs, PMS1 and MLH1, have been reported. Mutation of either one of them leads to a mitotic mutator phenotype (Prolla et al, Mol. Cell. Biol. 14:407–415 (1994)). At least three MutS homologs have been found in S. cerevisiae, namely MSH1, MSH2, and MSH3. Disruption of the MSH2 gene affects nuclear mutation rates. Mutants in S. cerevisae, MSH2, PMS1, and MLH1 have been found to exhibit increased rates of expansion and contraction of dinucleotide repeat sequences (Strand et al., Nature, 365:274–276 (1993)).

It has been reported that a number of human tumors such as lung cancer, prostate cancer, ovarian cancer, breast cancer, colon cancer and stomach cancer show instability of repeated DNA sequences (Han et al., Cancer, 53:5087–5089 (1993); Thibodeau et al., Science 260:816–819 (1993); Risinger et al., Cancer 53:5100–5103 (1993)). This phenomenon suggests that lack of the DNA mismatch repair is probably the cause of these tumors.

Little was known about the DNA mismatch repair system in humans until recently, the human homolog of the MutS gene was cloned and found to be responsible for hereditary nonpolyposis colon cancer (HNPCC), (Fishel et al., Cell, 75:1027–1038 (1993) and Leach et al., Cell, 75:1215–1225 (1993)). HNPCC was first linked to a locus at chromosome 2p16 which causes dinucleotide instability. It was then demonstrated that a DNA mismatch repair protein (MutS) homolog was located at this locus, and that C→T transitional mutations at several conserved regions were specifically observed in HNPCC patients. Hereditary nonpolyposis colorectal cancer is one of the most common hereditable diseases of man, affecting as many as one in two hundred individuals in the western world.

It has been demonstrated that hereditary colon cancer can result from mutations in several loci. Familial adenomatosis polyposis coli (APC), linked to a gene on chromosome 5, is responsible for a small minority of hereditary colon cancer. Hereditary colon cancer is also associated with Gardner's syndrome, Turcot's syndrome, Peutz-Jaeghers syndrome and juvenile polyposis coli. In addition, hereditary nonpolyposis colon cancer may be involved in 5% of all human colon cancer. All of the different types of familial colon cancer have been shown to be transmitted by a dominant autosomal mode of inheritance.

In addition to localization of HNPCC, to the short arm of chromosome 2, a second locus has been linked to a predisposition to HNPCC (Lindholm, et al., Nature Genetics, 5:279–282 (1993)). A strong linkage was demonstrated between a polymorphic marker on the short arm of chromosome 3 and the disease locus.

This finding suggests that mutations on various DNA mismatch repair proteins probably play crucial roles in the development of human hereditary diseases and cancers.

HNPCC is characterized clinically by an apparent autosomal dominantly inherited predisposition to cancer of the colon, endometrium and other organs. (Lynch, H. T. et al., Gastroenterology, 104:1535–1549 (1993)). The identification of markers at 2p16 and 3p21–22 which were linked to disease in selected HNPCC kindred unequivocally established its mendelian nature (Peltomaki, P. et al., Science, 260:810–812 (1993)). Tumors from HNPCC patients are characterized by widespread alterations of simple repeated sequences (microsatellites) (Aaltonen, L. A., et al., Science, 260:812–816 (1993)). This type of genetic instability was originally observed in a subset (12 to 18% of sporadic colorectal cancers (Id.). Studies in bacteria and yeast indicated that a defect in DNA mismatch repair genes can result in a similar instability of microsatellites (Levinson, G. and Gutman, G. A., Nuc. Acids Res., 15:5325–5338 (1987)), and it was hypothesized that deficiency in mismatched repair was responsible for HNPCC (Strand, M. et al., Nature, 365:274–276 (1993)). Analysis of extracts from HNPCC tumor cell lines showed mismatch repair was indeed deficient, adding definitive support to this conjecture (Parsons, R. P., et al., Cell, 75:1227–1236 (1993)). As not all HNPCC kindred can be linked to the same loci, and as at least three genes can produce a similar phenotype in yeast, it seems likely that other mismatch repair genes could play a role in some cases of HNPCC.

hMLH1 is most homologous to the yeast mutL-homolog yMLH1 while hMLH2 and hMLH3 have greater homology to the yeast mutL-homolog yPMS1 (hMLH2 and hMLH3 due to their homology to yeast PMS1 gene are sometimes referred to in the literature as hPMS1 and hPMS2). In addition to hMLH1, both the hMLH2 gene on chromosome 2q32 and the hMLH3 gene, on chromosome 7p22, were found to be mutated in the germ line of HNPCC patients. This doubles the number of genes implicated in HNPCC and may help explain the relatively high incidence of this disease.

In accordance with one aspect of the present invention, there are provided novel putative mature polypeptides which are hMLH1, hMLH2 and hMLH3, as well as biologically active and diagnostically or therapeutically useful fragments, analogs and derivatives thereof. The polypeptides of the present invention are of human origin.

In accordance with another aspect of the present invention, there are provided isolated nucleic acid molecules encoding such polypeptides, including mRNAs, DNAs, cDNAs, genomic DNA as well as biologically active and diagnostically or therapeutically useful fragments, analogs and derivatives thereof.

In accordance with still another aspect of the present invention there are provided nucleic acid probes comprising nucleic acid molecules of sufficient length to specifically hybridize to hMLH1, hMLH2 and hMLH3 sequences.

In accordance with yet a further aspect of the present invention, there is provided a process for producing such polypeptides by recombinant techniques which comprises culturing recombinant prokaryotic and/or eukaryotic host cells, containing an hMLH1, hMLH2 or hMLH3 nucleic acid sequence, under conditions promoting expression of said protein and subsequent recovery of said proteins.

In accordance with yet a further aspect of the present invention, there is provided a process for utilizing such polypeptide, or polynucleotide encoding such polypeptide, for therapeutic purposes, for example, for the treatment of cancers.

In accordance with another aspect of the present invention there is provided a method of diagnosing a disease or a susceptibility to a disease related to a mutation in the hMLH1, hMLH2 or hMLH3 nucleic acid sequences and the proteins encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF DRAWINGS

The following drawings are illustrative of embodiments of the invention and are not meant to limit the scope of the invention as encompassed by the claims.

FIGS. 1A–1F illustrates the cDNA sequence of SEQ ID NO:1 and corresponding deduced amino acid sequence of SEQ ID NO:2 for the human DNA repair protein hMLH1. The amino acids are represented by their standard one-letter abbreviations. Sequencing was performed using a 373 Automated DNA sequencer (Applied Biosystems, Inc.). Sequencing accuracy is predicted to be greater than 97% accurate.

FIGS. 2A–2H illustrates the cDNA sequence of SEQ ID NO:3 and corresponding deduced amino acid sequence of SEQ ID NO:4 (hMLH2). The amino acids are represented by their standard one-letter abbreviations.

FIGS. 3A–3G illustrates the cDNA sequence of SEQ ID NO:5 and corresponding deduced amino acid sequence of SEQ ID NO:6 (hMLH3). The amino acids are represented by their standard one-letter abbreviations.

FIGS. 4A–4C. Alignment of the predicted amino acid sequences of S. cerevisiae PMS1 (yPMS1), with the hMLH2 (SEQ ID NO:4) and hMLH3 (SEQ ID NO:6) amino acid sequences using MACAW (version 1.0) program. Amino acid in conserved blocks are capitalized and shaded on the mean of their pair-wise scores.

DESCRIPTION OF THE INVENTION

Figure 5A:
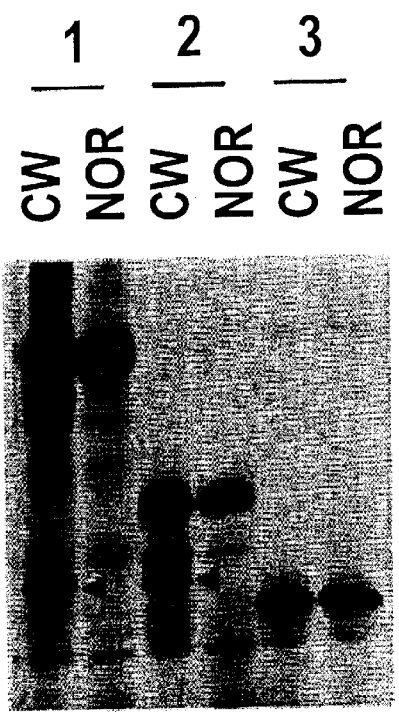
FIG. 5. Mutational analysis of hMLH2. (A) IVSP analysis and mapping of the transcriptional stop mutation in HNPCC patient CW. Translation of codons 1 to 369 (lane 1), codons 1 to 290 (lane 2), and codons 1 to 214 (lane 3). CW is translated from the cDNA of patient CW, while NOR was translated from the cDNA of a normal individual. The arrowheads indicate the truncated polypeptide due to the potential stop mutation. The arrows indicate molecular weight markers in kilodaltons. (B) Sequence analysis of CW indicates a C to T transition at codon 233 (indicated by the arrow). Lanes 1 and 3 are sequence derived from control patients; lane 2 is sequence derived from genomic DNA of CW. The ddA mixes from each sequencing mix were loaded in adjacent lanes to facilitate comparison as were those for ddC, ddD, and ddT mixes.

In accordance with an aspect of the present invention, there are provided isolated nucleic acids (polynucleotides) which encode for the mature polypeptides having the deduced amino acid sequence of FIGS. 1, 2 and 3 (SEQ ID No. 2, 4 and 6) or for the mature polypeptides encoded by the cDNA of the clone deposited as ATCC Deposit No. 75649, 75651, 75650, deposited on Jan. 25, 1994. The address of the American Type Culture Collection (ATCC) Depository referred to herein is: American Type Culture Collection, 10801 University Boulevard, Manassas, Va. 20110-2209.

ATCC Deposit No. 75649 is a cDNA clone which contains the full length sequence encoding the human DNA repair protein referred to herein as hMLH1; ATCC Deposit No. 75651 is a cDNA clone containing the full length cDNA sequence encoding the human DNA repair protein referred to herein as hMLH2; ATCC Deposit No. 75650 is a cDNA clone containing the full length DNA sequence referred to herein as hMLH3.

Polynucleotides encoding the polypeptides of the present invention may be obtained from one or more libraries prepared from heart, lung, prostate, spleen, liver, gallbladder, fetal brain and testes tissues. The polynucleotides of hMLH1 were discovered from a human gallbladder cDNA library. In addition, six cDNA clones which are identical to the hMLH1 at the N-terminal ends were obtained from human cerebellum, eight-week embryo, fetal heart, HSC172 cells and Jurket cell cDNA libraries. The hMLH1 gene contains an open reading frame of 756 amino acids encoding for an 85 kD protein which exhibits homology to the bacterial and yeast mutL proteins. However, the 5' non-translated region was obtained from the cDNA clone obtained from the fetal heart for the purpose of extending the non-translated region to design the oligonucleotides.

The hMLH2 gene was derived from a human T-cell lymphoma cDNA library. The hMLH2 cDNA clone identified an open reading frame of 2,796 base pairs flanked on both sides by in-frame termination codons. It is structurally related to the yeast PMS1 family. It contains an open reading frame encoding a protein of 932 amino acid residues. The protein exhibits the highest degree of homology to yeast PMS1 with 27% identity and 82% similarity over the entire protein.

A second region of significant homology among the three PMS related proteins is in the carboxyl terminus, between codons 800 to 900. This region shares a 22% and 47% homology between yeast PMS1 protein and hMLH2 and hMLH3 proteins, respectively, while very little homology of this region was observed between these proteins, and the other yeast mutL homolog, yMLH1.

The hMLH3 gene was derived from a human endometrial tumor cDNA library. The hMLH3 clone identified a 2,586 base pair open reading frame. It is structurally related to the yPMS2 protein family. It contains an open reading frame encoding a protein of 862 amino acid residues. The protein exhibits the highest degree of homology to yPMS2 with 32% identity and 66% similarity over the entire amino acid sequence.

It is significant with respect to a putative identification of hMLH1, hMLH2 and hMLH3 that the GFRGEAL domain which is conserved in mutL homologs derived from *E. coli* is conserved in the amino acid sequences of, hMLH1, hMLH2 and hMLH3.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1, 2 and 3 (SEQ ID No. 1) or that of the deposited clone or may be a different coding sequence which coding sequence, as a result of the redundancy or degeneracy of the genetic code, encodes the same mature polypeptides as the DNA of FIGS. 1, 2 and 3 (SEQ ID No. 2, 4 and 6) or the deposited cDNA(s).

The polynucleotides which encode for the mature polypeptides of FIGS. 1, 2 and 3 (SEQ ID No. 2, 4 and 6) or for the mature polypeptides encoded by the deposited cDNAs may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptides having the deduced amino acid sequences of FIGS. 1, 2 and 3 (SEQ ID No. 2, 4 and 6) or the polypeptides encoded by the cDNA of the deposited clones. The variants of the polynucleotides may be a naturally occurring allelic variant of the polynucleotides or a non-naturally occurring variant of the polynucleotides.

Thus, the present invention includes polynucleotides encoding the same mature polypeptides as shown in FIGS. 1, 2 and 3 (SEQ ID No. 2, 4 and 6) or the same mature polypeptides encoded by the cDNA of the deposited clones as well as variants of such polynucleotides which variants encode for a fragment, derivative or analog of the polypeptides of FIGS. 1, 2 and 3 (SEQ ID No. 2, 4 and 6) or the polypeptides encoded by the cDNA of the deposited clones. Such nucleotide variants include deletion variants, substitution variants and addition or insertion variants.

As hereinabove indicated, the polynucleotides may have a coding sequence which is a naturally occurring allelic variant of the coding sequence shown in FIGS. 1, 2 and 3 (SEQ ID No. 1, 3 and 5) or of the coding sequence of the deposited clones. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptides of the present invention. The marker sequence may be, for example, a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1, 2 and 3 (SEQ ID NO:1, 3 and 5) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, 3 and 5 for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2, 4 and 6 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112.

The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to polypeptides which have the deduced amino acid sequence of FIGS. 1, 2 and 3 (SEQ ID No. 2, 4 and 6) or which have the amino acid sequence encoded by the deposited cDNA(s), as well as fragments, analogs and derivatives of such polypeptides.

The terms "fragment," "derivative" and "analog" when-referring to the polypeptides of FIGS. 1, 2 and 3 (SEQ ID No. 2, 4 and 6) or that encoded by the deposited cDNA(s), means polypeptides which retain essentially the same biological function or activity as such polypeptides. Thus, an analog includes a proprotein which can be activated by cleavage of the proprotein portion to produce an active mature polypeptide.

The polypeptides of the present invention may be a recombinant polypeptide, a natural polypeptide or a synthetic polypeptide, preferably a recombinant polypeptide.

The fragment, derivative or analog of the polypeptides of FIGS. 1, 2 and 3 (SEQ ID No. 2, 4 and 6) or that encoded by the deposited cDNAs may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol). Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2, 4 and 6 (in particular the mature polypeptide) as well as polypeptides which have at least 70% similarity (preferably at least 70% identity) to the polypeptide of SEQ ID NO:2, 4 and 6 and more preferably at least 90% similarity (more preferably at least 90% identity) to the polypeptide of SEQ ID NO:2, 4 and 6 and still more preferably at least 95% similarity (still more preferably at least 95% identity) to the polypeptide of SEQ ID NO:2, 4 and 6 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the hMLH1, hMLH2 and hMLH3 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the proteins.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9;

animal cells such as CHO, COS or Bowes melanoma;

adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen, Inc.), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation Systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

In accordance with a further aspect of the invention, there is provided a process for determining susceptibility to cancer, in particular, a hereditary cancer. Thus, a mutation in a human repair protein, which is a human homolog of mutL, and in particular those described herein, indicates a susceptibility to cancer, and the nucleic acid sequences encoding such human homologs may be employed in an assay for ascertaining such susceptibility. Thus, for example, the assay may be employed to determine a mutation in a human DNA repair protein as herein described, such as a deletion, truncation, insertion, frame shift, etc., with such mutation being indicative of a susceptibility to cancer.

A mutation may be ascertained for example, by a DNA sequencing assay. Tissue samples, including but not limited to blood samples are obtained from a human patient. The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the DNA repair protein of the invention. The primer sequence is generally comprised of 15 to 30 and preferably from 18 to 25 consecutive bases of the human DNA repair gene. Table 1 sets forth an illustrative example of oligonucleotide primer sequences based on hMLH1. The primers are used in pairs (one "sense" strand and one "anti-sense") to amplify the cDNA from the patients by the PCR method (Saiki et al., Nature, 324:163–166 (1986)) such that three overlapping fragments of the patient's cDNA's for such protein are generated. Table 1 also shows a list of preferred primer sequence pairs. The overlapping fragments are then subjected to dideoxynucleotide sequencing using a set of primer sequences synthesized to correspond to the base pairs of the cDNA's at a point approximately every 200 base pairs throughout the gene.

TABLE 1

Primer Sequences used to amplify gene region using PCR

| Name | SEQ ID NO: | Start Site and Arrangement | Sequence |
|---|---|---|---|
| 758 | 7 | sense-(-41)* | GTTGAACATCTAGACGTCTC |
| 1319 | 8 | sense-8 | TCGTGGCAGGGGTTATTCG |
| 1321 | 9 | sense-619 | CTACCCAATGCCTCAACCG |
| 1322 | 10 | sense-677 | GAGAACTGATAGAAATTGGATG |
| 1314 | 11 | sense-1548 | GGGACATGAGGTTCTCCG |
| 1323 | 12 | sense-1593 | GGGCTGTGTGAATCCTCAG |
| 773 | 13 | anti-53 | CGGTTCACCACTGTCTCGTC |
| 1313 | 14 | anti-971 | TCCAGGATGCTCTCCTCG |
| 1320 | 15 | anti-1057 | CAAGTCCTGGTAGCAAAGTC |
| 1315 | 16 | anti-1760 | ATGGCAAGGTCAAAGAGCG |
| 1316 | 17 | anti-1837 | CAACAATGTATTCAGXAAGTCC |
| 1317 | 18 | anti-2340 | TTGATACAACACTTTGTATCG |
| 1318 | 19 | anti-2415 | GGAATACTATCAGAAGGCAAG |

*Numbers corresponding to location along nucleotide sequence of FIG. 1 where ATG is number 1.

Preferred primer sequences pairs:

758, 1313

1319, 1320

660, 1909

725, 1995

1680, 2536

1727, 2610

The nucleotide sequences shown in Table 1 represent SEQ ID No. 7 through 19, respectively.

Table 2 lists representative examples of oligonucleotide primer sequences (sense and anti-sense) which may be used, and preferably the entire set of primer sequences are used for sequencing to determine where a mutation in the patient DNA repair protein may be. The primer sequences may be from 15 to 30 bases in length and are preferably between 18 and 25 bases in length. The sequence information determined from the patient is then compared to non-mutated sequences to determine if any mutations are present.

TABLE 2

Primer Sequences Used to Sequence the Amplified Fragments

| Name | SEQ ID NO: | Start Site and Arrangement | Sequence |
|---|---|---|---|
| 5282 | 20 | sense-377* | ACAGAGCAAGTTACTCAGATG |
| 5283 | 21 | sense-552 | GTACACAATGCAGGCATTAG |
| 5284 | 22 | sense-904 | AATGTGGATGTTAATGTGCAC |
| 5285 | 23 | sense-1096 | CTGACCTCGTCTTCCTAC |
| 5286 | 24 | sense-1276 | CAGCAAGATGAGGAGATGC |
| 5287 | 25 | sense-1437 | GGAAATGGTGGAAGATGATTC |
| 5288 | 26 | sense-1645 | CTTCTCAACACCAAGC |
| 5289 | 27 | sense-1895 | GAAATTGATGAGGAAGGGAAC |
| 5295 | 28 | sense-1921 | CTTCTGATTGACAACTATGTGC |
| 5294 | 29 | sense-2202 | CACAGAAGATGGAAATATCCTG |
| 5293 | 30 | sense-2370 | GTGTTGGTAGCACTTAAGAC |
| 5291 | 31 | anti-525 | TTTCCCATATTCTTCACTTG |
| 5290 | 32 | anti-341 | GTAACATGAGCCACATGGC |
| 5292 | 33 | anti-46 | CCACTGTCTCGTCCAGCCG |

*Numbers corresponding to location along nucleotide sequence of FIG. 1 where ATG is number 1.

The nucleotide sequences shown in Table 2 represent SEQ ID No. 20 through 33, respectively.

In another embodiment, the primer sequences from Table 2 could be used in the PCR method to amplify a mutated region. The region could be sequenced and used as a diagnostic to predict a predisposition to such mutated genes.

Alternatively, the assay to detect mutations in the genes of the present invention may be performed by genetic testing based on DNA sequence differences achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and SI protection or the chemical cleavage method (e.g., Cotton et al., PNAS, USA, 85:4397–4401 (1985)). Perfectly matched sequences can be distinguished from mismatched duplexes by RNase A digestion or by differences in melting temperatures.

Thus, the detection of a specific DNA sequence may be achieved by methods such as hybridization, RNase protection, chemical cleavage, Western Blot analysis, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The polypeptides may also be employed to treat cancers or to prevent cancers, by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Each of the cDNA sequences identified herein or a portion thereof can be used in numerous ways as polynucleotide reagents. The sequences can be used as diagnostic probes for the presence of a specific mRNA in a particular cell type. In addition, these sequences can be used as diagnostic probes suitable for use in genetic linkage analysis (polymorphisms).

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome-specific cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

hMLH2 has been localized using a genomic P1 clone (1670) which contained the 5' region of the hMLH2 gene. Detailed analysis of human metaphase chromosome spreads, counterstained to reveal banding, indicated that the hMLH2 gene was located within bands 2q32. Likewise, hMLH3 was localized using a genomic P1 clone (2053) which contained the 3' region of the hMLH3 gene. Detailed analysis of human metaphase chromosome spreads, counterstained to reveal banding, indicated that the hMLH3 gene was located within band 7p22, the most distal band on chromosome 7. Analysis with a variety of genomic clones showed that hMLH3 was a member of a subfamily of related genes, all on chromosome 7.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression of hMLH1

The full length DNA sequence encoding human DNA mismatch repair protein hMLH1, ATCC #75649, is initially amplified using PCR oligonucleotide primers corresponding to the 5' and 3' ends of the DNA sequence to synthesize insertion fragments. The 5' oligonucleotide primer has the sequence 5' CGGGATCCATGTCGTTCGTGGCAGGG 3' (SEQ ID No. 34), contains a BamHI restriction enzyme site followed by 18 nucleotides of hMLH1 coding sequence following the initiation codon; the 3' sequence 5' GCTCTAGATTAACACCTCT CAAAGAC 3' (SEQ ID No. 35) contains complementary sequences to an XbaI site and is at the end of the gene. The restriction enzyme sites correspond to the restriction enzyme sites on the bacterial expression vector pQE-9. (Qiagen, Inc., Chatsworth, Calif.). The plasmid vector encodes antibiotic resistance (Amp$^r$), a bacterial origin of replication (ori), an IPTG-regulatable promoter/operator (P/o), a ribosome binding site (RBS), a 6-histidine tag (6-His) and restriction enzyme cloning sites. The pQE-9 vector is digested with BamHI and XbaI and the insertion fragments are then ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). Tho O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression. Cells are grown an extra 3 to 4 hours. Cells are then harvested by centrifugation (20 mins at 6000×g). The cell pellet is solubilized in the chaotropic agent 6 Molar Guanidine HCl. After clarification, solubilized hMLH1 is purified from this solution by chromatography on a Nickel-Chelate column under conditions that allow for tight binding by proteins containing the 6-His tag (Hochuli, E. et al., Genetic Engineering, Principles & Methods, 12:87–98 (1990). Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate. The purified protein was analyzed by SDS-PAGE.

EXAMPLE 2

Spontaneous Mutation Assay for Detection of the Expression of hMLH1, hMLH2 and hMLH3 and Complementation to the E. coli mutl The pQE9hMLH1, pQE9hMLH2 or pQE9hMLH3/GW3733, transformants were subjected to the spontaneous mutation assay. The plasmid vector pQE9 was also transformed to AB1157 (k-12, argE3 hisG4, LeuB6 proA2 thr-1 ara-1 rpsL31 supE44 tsx-33) and GW3733 to use as the positive and negative control respectively.

Fifteen 2 ml cultures, inoculated with approximately 100 to 1000 E. coli, were grown 2×10$^8$ cells per ml in LB ampicillin medium at 37° C. Ten microliters of each culture were diluted and plated on the LB ampicillin plates to measure the number of viable cells. The rest of the cells from each culture were then concentrated in saline and plated on minimal plates lacking of arginine to measure reversion of Arg$^+$. In Table 3, the mean number of mutations per culture (m) was calculated from the median number (r) of mutants per distribution, according to the equation (r/m)−ln(m)=1.24 (Lea et al., J. Genetics 49:264–285 (1949)). Mutation rates per generation were recorded as m/N, with N representing the average number of cells per culture.

TABLE 3

| Spontaneous Mutation Rates | |
|---|---|
| Strain | Mutation/generation |
| AB1157 + vector | (5.6 ± 0.1) × 10-9a |
| GW3733 + vector | (1.1 ± 0.2) × 10-6a |
| GW3733 + phMLH1 | (3.7 ± 1.3) × 10-7a |
| GW3733 + PhMLH2 | (3.1 ± 0.6) × 10-7b |
| GW3733 + phMLH3 | (2.1 ± 0.8) × 10-7b | a: Average of three experiments.
b: Average of four experiments.

The functional complementation result showed that the human mutL can partially rescue the E. coli mutL mutator phenotype, suggesting that the human mutL is not only successfully expressed in a bacterial expression system, but also functions in bacteria.

EXAMPLE 3

Chromosomal Mapping of the hMLH1

An oligonucleotide primer set was designed according to the sequence at the 5' end of the cDNA for hMLH1. This primer set would span a 94 bp segment. This primer set was used in a polymerase chain reaction under the following set of conditions:

30 seconds, 95 degrees C.

1 minute, 56 degrees C.

1 minute, 70 degrees C.

This cycle was repeated 32 times followed by one 5 minute cycle at 70 degrees C. Human, mouse, and hamster DNA were used as template in addition to a somatic cell hybrid panel (Bios, Inc). The reactions were analyzed on either 8% polyacrylamide gels or 3.5% agarose gels. A 94 base pair band was observed in the human genomic DNA sample and in the somatic cell hybrid sample corresponding to chromosome 3. In addition, using various other somatic cell hybrid genomic DNA, the hMLH1 gene was localized to chromosome 3p.

EXAMPLE 4

Method for Determination of Mutation of hMLH1 Gene in HNPCC Kindred cDNA was produced from RNA obtained from tissue samples from persons who are HNPCC kindred and the cDNA was used as a template for PCR, employing the primers 5' GCATC TAGACGTTTCCTTGGC 3' (SEQ ID No. 36) and 5' CATCCALAGCTTCTGT TCCCG 3' (SEQ ID No. 37), allowing amplification of codons 1 to 394 of FIG. 1; 5' GGGGTGCAGCAGCACATCG 3' (SEQ ID No. 38) and 5' GGAGGCAGAATGTGTGAGCG 3' (SEQ ID No. 39), allowing amplification of codons 326 to 729 of FIG. 1 (SEQ ID No. 2); and 5' TCCCAAAGAAGGACTTGCT 3' (SEQ ID No. 40) and 5' AGTATAAGTCTTAAGTGCTACC 3' (SEQ ID No. 41), allowing amplification of codons 602 to 756 plus 128 nt of 3—untranslated sequences of FIG. 1 (SEQ ID No. 2). The PCR conditions for all analyses used consisted of 35 cycles at 95° C. for 30 seconds, 52–58° C. for 60 to 120 seconds, and 70° C. for 60 to 120 seconds, in the buffer solution described in San Sidransky, D. et al., Science, 252:706 (1991). PCR products were sequenced using primers labeled at their 5' end with T4 polynucleotide kinase, employing SequiTherm Polymerase (Epicentre Technologies). The intron-exon borders of selected exons were also determined and genomic PCR products analyzed to confirm the results. PCR products harboring suspected mutations were then cloned and sequenced to validate the results of the direct sequencing. PCR products were cloned into T-tailed vectors as described in Holton, T. A. and Graham, M. W., Nucleic Acids Research, 19:1156 (1991) and sequenced with T7 polymerase (United States Biochemical). Affected individuals from seven kindreds all exhibited a heterozygous deletion of codons 578 to 632 of the hMLH1 gene. The derivation of five of these seven kindreds could be traced to a common ancestor. The genomic sequences surrounding codons 578–632 were determined by cycle-sequencing of the P1 clones (a human genomic P1 library which contains the entire hMLH1 gene (Genome Systems)) using SequiTherm Polymerase, as described by the manufacturer, with the primers were labeled with T4 polynucleotide kinase, and by sequencing PCR products of genomic DNA. The primers used to amplify the exon containing codons 578–632 were 5' TTTATGGTTTCTCACCTGCC 3' (SEQ ID No. 42) and 5' GTTATCTGCCCACCTCAGC 3' (SEQ ID No. 43). The PCR product included 105 bp of intron C sequence upstream of the exon and 117 bp downstream. No mutations in the PCR product were observed in the kindreds, so the deletion in the RNA was not due to a simple splice site mutation. Codons 578 to 632 were found to constitute a single exon which was deleted from the gene product in the kindreds described above. This exon contains several highly conserved amino acids.

In a second family (L7), PCR was performed using the above primers and a 4 bp deletion was observed beginning at the first nucleotide (nt) of codon 727. This produced a frame shift with a new stop codon 166 nt downstream, resulting in a substitution of the carboxy-terminal 29 amino acids of hMLH1 with 53 different amino acids, some encoded by nt normally in the 3' untranslated region.

A different mutation was found in a different kindred (L2516) after PCR using the above primers, the mutation consisting of a 4 bp insert between codons 755 and 756. This insertion resulted in a frame shift and extension of the ORF to include 102 nucleotides (34 amino acids) downstream of the normal termination codon. The mutations in both kindreds L7 and L2516 were therefore predicted to alter the C-terminus of hMLH1.

Figure 5B:
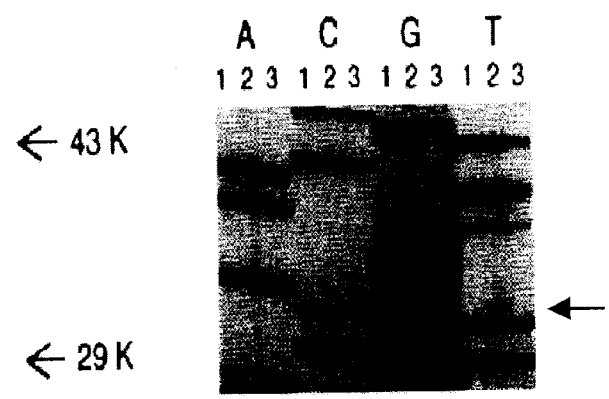
Figure 6A:
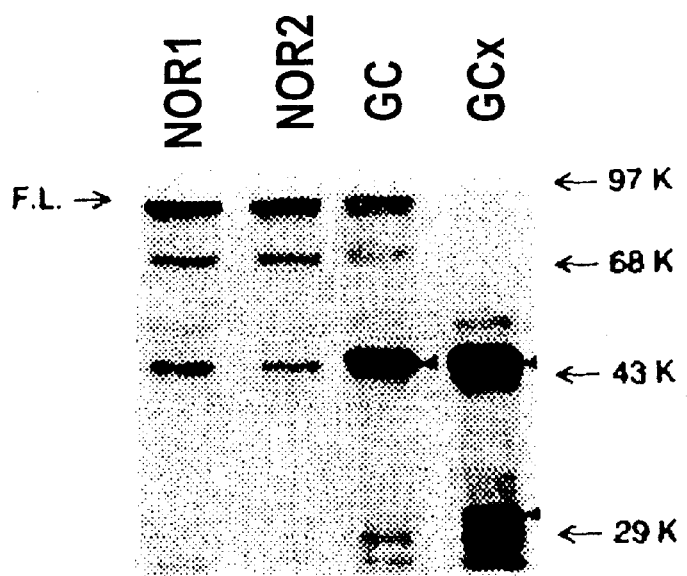
FIG. 6. Mutational analysis of hMLH3. (A) IVSP analysis of hMLH3 from patient GC. Lane GC is from fibroblasts of individual GC; lane GCx is from the tumor of patient GC; lanes NOR1 and 2 are from normal control individuals. FL indicates full-length protein, and the arrowheads indicate the germ line truncated polypeptide. The arrows indicate molecular weight markers in kilodaltons (B) PCR analysis of DNA from a patient GC shows that the lesion in present in both hMLH3 alleles in tumor cells. Amplification was done using primers that amplify 5', 3', or within (MID) the region deleted in the cDNA. Lane 1, DNA derived from fibroblasts of patient GC; lane 2, DNA derived from tumor of patient GC; lane 3, DNA derived from a normal control patient; lane 4, reactions without DNA template. Arrows indicate molecular weight in base pairs.
Figure 6B:
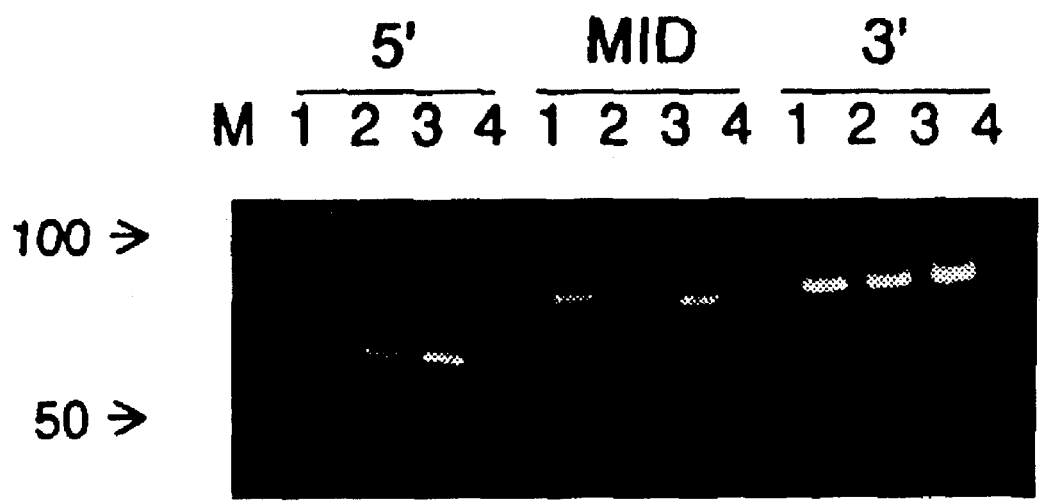

A possible mutation in the hMLH1 gene was determined from alterations in size of the encoded protein, where kindreds were too few for linkage studies. The primers used for coupled transcription-translation of hMLH1 were 5' GGATCCTAATACGACTCACTATAGG-GAGACCACCATGGCATCT AGACGTTTCCCTTGGC 3' (SEQ ID No. 44) and 5' CATCCAAGCTTCTGTTCCCG 3' (SEQ ID No. 45) for codons 1 to 394 of FIG. 1 and 5' GGATCCTAATACGACTCACTATAGG-GAGACCACCATGGG GGTGCAGCAGCACATCG 3' (SEQ ID No. 46) and 5' GGAGGCAGAATGTG TGAGCG 3' (SEQ ID No. 47) for codons 326 to 729 of FIG. 1 (SEQ ID No. 2). The resultant PCR products had signals for transcription by T7 RNA polymerase and for the initiation of translation at their 5' ends. RNA from lymphoblastoid cells of patients from 18 kindreds was used to amplify two products, extending from codon 1 to codon 394 or from codon 326 to codon 729, respectively. The PCR products were then transcribed and translated in vitro, making use of transcription-translation signals incorporated into the PCR primers. PCR products were used as templates in coupled transcription-translation reactions performed as described by Powell, S. M. et al., New England Journal of Medicine, 329:1982, (1993), using 40 micro CI of $^{35}$S labeled methionine. Samples were diluted in sample buffer, boiled for five minutes and analyzed by electrophoresis on sodium dodecyl sulfate-polyacrylamide gels containing a gradient of 10% to 20% acrylamide. The gels were dried and subjected to radiography. All samples exhibited a polypeptide of the expected size, but an abnormally migrating polypeptide was additionally found in one case. The sequence of the relevant PCR product was determined and found to include a 371 bp deletion beginning at the first nucleotide (nt) of codon 347. This alteration was present in heterozygous form, and resulted in a frame shift in a new stop codon 30 nt downstream of codon 346, thus explaining the truncated polypeptide observed.

Four colorectal tumor cell lines manifesting microsatellite instability were examined. One of the four (cell line H6)

showed no normal peptide in this assay and produced only a short product migrating at 27 kd. The sequence of the corresponding cDNA was determined and found to harbor a C to A transversion at codon 252, resulting in the substitution of a termination codon for serine. In accord with the translational analyses, no band at the normal C position was identified in the cDNA or genomic DNA from this tumor, indicating that it was devoid of a functional hMLH1 gene.

Table 4 sets forth the results of these sequencing assays. Deletions were found in those people who were known to have a family history of the colorectal cancer. More particularly, 9 of 10 families showed an hMLH1 mutation.

TABLE 4

Summary of Mutations in hMLH1

| Sample | Codon | cDNA Nucleotide Change | Predicted Coding Change |
| --- | --- | --- | --- |
| Kindreds F2, F3, F6, F8, F10, F11, F52 | 578–632 | 165 bp deletion | In-frame deletion |
| Kindred L7 | 727/728 | 4 bp deletion (TCACACATTC to TCATTCT) | Frameshift and substitution of new amino acids |
| Kindred L2516 | 755/756 | 4 bp insertion (GTGTTAA to GTGTTTGTTAA) | Extension of C-terminus |
| Kindred RA | 347 | 371 bp deletion | Frameshift/Truncation |
| H6 Colorectal Tumor | 252 | Transversion (TCA to TAA) | Serine to Stop |

EXAMPLE 5

Bacterial Expression and Purification of hMLH2

The DNA sequence encoding hMLH2, ATCC #75651, is initially amplified using PCR oligonucleotide primers corresponding to the 5' and 3' ends of the DNA sequence to synthesize insertion fragments. The 5' oligonucleotide primer has the sequence 5' CGGGATCCATGAAACAAT-TGCCTGCGGC 3' (SEQ ID No. 48) contains a BamHI restriction enzyme site followed by 17 nucleotides of hMLH2 following the initiation codon. The 3' sequence 5' GCTCTAGACCAGACTCAT by 17 nucleotides of hMLH2 following the initiation codon. The 3' sequence 5' GCTCTA-GACCAGACTCAT GCTGTTTT 3' (SEQ ID No. 49) contains complementary sequences to an XbaI site and is followed by 18 nucleotides of hMLH2. The restriction enzyme sites correspond to the restriction enzyme sites on the bacterial expression vector pQE-9 (Qiagen, Inc. Chatsworth, Calif.). pQE-9 encodes antibiotic resistance (Ampr), a bacterial origin of replication (ori), an IPTG-regulatable promoter operator (P/O), a ribosome binding site (RBS), a 6-His tag and restriction enzyme sites. The amplified sequences and pQE-9 are then digested with BamHI and XbaI. The amplified sequences are ligated into pQE-9 and are inserted in frame with the sequence encoding for the histidine tag and the RBS. The ligation mixture is then used to transform E. coli strain M15/rep4 (Qiagen, Inc.) which contains multiple copies of the plasmid pREP4, which expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). Tho O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the laci repressor, clearing the P/O leading to increased gene expression. Cells are grown an extra 3 to 4 hours. Cells are then harvested by centrifugation (20 mins at 6000×g). The cell pellet is solubilized in the chaotropic agent 6 Molar Guanidine HCl. After clarification, solubilized hMLH2 is purified from this solution by chromatography on a Nickel-Chelate column under conditions that allow for tight binding by proteins containing the 6-His tag (Hochuli, E. et al., Genetic Engineering, Principles & Methods, 12:87–98 (1990). Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate. The purified protein was analyzed by SDS-PAGE.

EXAMPLE 6

Bacterial Expression and Purification of hMLH3

The DNA sequence encoding hMLH3, ATCC #75650, is initially amplified using PCR oligonucleotide primers corresponding to the 5' and 3' ends of the DNA sequence to synthesize insertion fragments. The 5' oligonucleotide primer has the sequence 5' CGGGATCCATGGAGC-GAGCTGAGAGC 3' (SEQ ID No. 50) contains a BamHI restriction enzyme site followed by 18 nucleotides of hMLH3 coding sequence starting from the presumed terminal amino acid of the processed protein. The 3' sequence 5' GCTCTAGAGTGAAG ACTCTGTCT 3' (SEQ ID No. 51) contains complementary sequences to an XbaI site and is followed by 18 nucleotides of hMLH3. The restriction enzyme sites correspond to the restriction enzyme sites on the bacterial expression vector pQE-9 (Qiagen, Inc. Chatsworth, Calif.). pQE-9 encodes antibiotic resistance (Ampr), a bacterial origin of replication (ori), an IPTG-regulatable promoter operator (P/O), a ribosome binding site (RBS), a 6-His tag and restriction enzyme sites. The amplified sequences and pQE-9 are then digested with BamHI and XbaI. The amplified sequences are ligated into pQE-9 and are inserted in frame with the sequence encoding for the histidine tag and the RBS. The ligation mixture was then used to transform E. coli strain M15/rep4 (Qiagen, Inc.) which contains multiple copies of the plasmid pREP4, which expresses the laci repressor and also confers kanamycin resistance (Kanr). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). Tho O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the laci repressor, clearing the P/O leading to increased gene expression. Cells are grown an extra 3 to 4 hours. Cells are then harvested by centrifugation (20 mins at 6000×g). The cell pellet is solubilized in the chaotropic agent 6 Molar Guanidine HCl. After clarification, solubilized stanniocalcin is purified from this solution by chromatography on a Nickel-Chelate column under conditions that allow for tight binding by proteins containing the 6-His tag (Hochuli, E. et al., Genetic Engineering, Principles & Methods, 12:87–98 (1990). Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate. The purified protein was analyzed by SDS-PAGE.

EXAMPLE 7

Method for Determination of Mutation of hMLH2 and hMLH3 in Hereditary Cancer

Isolation of Genomic Clones

A human genomic P1 library (Genomic Systems, Inc.) was screened by PCR using primers selected for the cDNA sequence of hMLH2 and hMLH3. Two clones were isolated for hMLH2 using primers 5' AAGCTGCTCTGT-TAAAAGCG 3' (SEQ ID No. 52) and 5' GCACCAGCATC-CAAGGAG 3' (SEQ ID No. 53) and resulting in a 133 bp product. Three clones were isolated for hMLH3, using primers 5' CAACCATGAGACACATCGC 3' (SEQ ID No. 54) and 5' AGGTTAGTGAAGACTCTGTC 3' (SEQ ID No. 55) resulting in a 121 bp product. Genomic clones were nick-translated with digoxigenindeoxy-uridine 5'-triphosphate (Boehringer Manheim), and FISH was performed as described (Johnson, Cg. et al., Methods Cell Biol., 35:73–99 (1991)). Hybridization with the hMLH3 probe were carried out using a vast excess of human cot-1 DNA for specific hybridization to the expressed hMLH3 locus. Chromosomes were counterstained with 4,6-diamino-2-phenylidole and propidium iodide, producing a combination of C- and R-bands. Aligned images for precise mapping were obtained using a tripleband filter set (Chroma Technology, Brattleboro, Vt.) in combination with a cooled charge-coupled device camera (Photometrics, Tucson, Ariz.) and variable excitation wavelength filters (Johnson, Cv. et al., Genet. Anal. Tech. Appl., 8:75 (1991)). Image collection, analysis and chromosomal fractional length measurements were done suing the ISee Graphical Program System (Inovision Corporation, Durham, N.C.).

Transcription Coupled Translation Mutation Analysis

For purposes of IVSP analysis the hMLH2 gene was divided into three overlapping segments. The first segment included codons 1 to 500, while the middle segment included codons 270 to 755, and the last segment included codons 485 to the translational termination site at codon 933. The primers for the first segment were 5' GGATC-CTAATACGACTCACT ATAGGGAGACCACCATGGAA-CAATTGCCTGCGG 3' (SEQ ID No. 56) and 5' CCT-GCTCCACTCATCTGC 3' (SEQ ID No. 57), for the middle segment were 5' GGATCCTAATACGACTCACTATAGG-GAGACCACCATGGAAGA TATCTTAAAGTTAATCCG 3' (SEQ ID No. 58) and 5' GGCTTCTTCTACTC TATATGG 3' (SEQ ID No. 59), and for the final segment were 5' G G AT C C TA ATA C G A C T C A C TATA G G - GAGACCACCATGGCAGGTCTTGAAAACTC TTCG 3' (SEQ ID No. 60) and 5' AAAACAAGTCAGTGAATCCTC 3' (SEQ ID No. 61). The primers used for mapping the stop mutation in patient CW all used the same 5' primer as the first segment. The 3' nested primers were: 5' AAGCA-CATCTGTTTCTGCTG 3' (SEQ ID No. 62) codons 1 to 369; 5' ACGAGTAGATTCCTTTAGGC 3' (SEQ ID No. 63) codons 1 to 290; and 5' CAGAACTGACATGAGAGCC 3' (SEQ ID No. 64) codons 1 to 214.

For analysis of hMLH3, the hMLH3 cDNA was amplified as a full-length product or as two overlapping segments. The primers for full-length hMLH3 were 5' GGATCCTAATAC-GACTCACTATAGGGAGACCACCATG-GAGCGAGCTGAGAGC 3' (SEQ ID No. 65) and 5' AGGT-TAGTGAAGACTCTGTC 3' (SEQ ID No. 66) (codons 1 to 863). For segment 1, the sense primer was the same as above and the antisense primer was 5' CTGAGGTCT CAG-CAGGC 3' (SEQ ID No. 67) (codons 1 to 472). Segment 2 primers were 5' GGATCCTAATACGACTCACTATAGG-GAGACCACCATGGTGTC CATTTCCAGACTGCG 3' (SEQ ID No. 68) and 5' AGGTTAGTGAAGACTCT GTC 3' (SEQ ID No. 69) (codons 415 to 863). Amplifications were done as described below.

The PCR products contained recognition signals for transcription by T7 RNA polymerase and for the initiation of translation at thei 5' ends. PCR products were used as templates in coupled transcription-translation reactions containing 40 uCi of $^{36}$S-methionine (NEN, Dupont). Samples were diluted in SDS sample buffer, and analyzed by electrophoresis on SDS-polyacrylamide gels containing a gradient of 10 to 20% acrylamide. The gels were fixed, treated with EnHance (Dupont), dried and subjected to autoradiography.

RT-PCR and Direct Sequencing of PCR Products cDNAs were generated from RNA of lymphoblastoid or tumor cells with Superscript II (Life Technologies). The cDNAs were then used as templates for PCR. The conditions for all amplifications were 35 cycles at 95° C. for 30s, 52° C. to 62° C. for 60 to 120s, and 70° C. for 60 to 120s, in buffer. The PCR products were directly sequenced and cloned into the T-tailed cloning vector PCR2000 (Invitrogen) and sequenced with T7 polymerase (United States Biochemical). For the direct sequencing of PCR products, PCR reactions were first phenolchloroform extracted and ethanol precipitated. Templates were directly sequenced using Sequitherm polymerase (Epicentre Technologies) and gamma-$^{32}$P labelled primers as described by the manufacturer.

Intron/Exon Boundaries and Genomic Analysis of Mutations

Intron/exon borders were determined by cycle-sequencing P1 clones using gamma-$^{32}$P end labelled primers and SequiTherm polymerase as described by the manufacturer. The primers used to amplify the hMLH2 exon containing codons 195 to 233 were 5' TTATTTGGCA-GAAAAGCAGAG (SEQ ID No. 70) 3' and 5' TTAAAAGACTAACCTCTTGCC 3' (SEQ ID No. 71), which produced a 215 bp product. The product was cycle sequenced using the primer 5' CTGCTGTTATGAA-CAATATGG 3' (SEQ ID No. 72). The primers used to analyze the genomic deletion of hMLH3 in patient GC were: for the 5' region amplification 5' CAGAAGCAGTTG-CAAAGCC 3' (SEQ ID No. 73) and 5' AAACCGTACTCT-TCACACAC 3' (SEQ ID No. 74) which produces a 74 bp product containing codons 233 to 257, primers 5' GAG-GAAAAGCTTTTGTTGGC 3' (SEQ ID No. 75) and 5' CAGTGGCTGCTGACTGAC 3' (SEQ ID No. 76) which produce a 93 bp product containing the codons 347 to 377, and primers 5' TCCAGAACCAAGAAGGAGC 3' (SEQ ID No. 77) and 5' TGAGGTCTCAGCAGGC 3' (SEQ ID No. 78) which produce a 99 bp product containing the codons 439 to 472 of hMLH3.

TABLE 5

Summary of Mutations in HMLH2 and HMLH3 from patients affected with HNPCC

| Sample | Codon | Nucleotides | cDNA Change | Genomic Change | Predicted Coding Change |
|---|---|---|---|---|---|
| HMLH2 | | | | | |
| CW | 233 | | Skipped Exon | CAG to TAG | GLN to Stop Codon |
| HMLH3 | | | | | |
| MM, NS, TF | 20 | | CGG to CAG | CGG to CAG | ARG to GLN |
| GC | | 268 to 669 | 1,203 bp Deletion | Deletion | In-frame deletion |
| GCx | | 268 to 669 | 1,203 bp Deletion | Deletion | Frameshift, trucation |

EXAMPLE 8

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein prooduct.

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence of amino acid residues 1 to 756 of SEQ ID NO:2.

2. The isolated polypeptide of claim 1 wherein said amino acid sequence comprises a heterologous polypeptide.

3. The isolated polypeptide of claim 1 which is glycosylated.

4. A composition comprising the isolated polypeptide of claim 1 and a carrier.

5. A polypeptide produced by a method comprising:
   (a) culturing a host cell under conditions suitable to produce the isolated polypeptide of claim 1, wherein said host cell comprises a polynucleotide which encodes said polypeptide; and
   (b) recovering the polypeptide.

6. An isolated polypeptide comprising the amino acid sequence of the full-length polypeptide encoded by the cDNA clone contained in ATCC Deposit No. 75649.

7. The isolated polypeptide of claim 6 wherein said amino acid sequence comprises a heterologous polypeptide.

8. The isolated polypeptide of claim 6 which is glycosylated.

9. A composition comprising the isolated polypeptide of claim 6.

10. A polypeptide produced by a method comprising:
    (a) culturing a host cell under conditions suitable to produce the isolated polypeptide of claim 6, wherein said host cell comprises a polynucleotide which encodes said polypeptide; and
    (b) recovering the polypeptide.

11. An isolated polypeptide comprising a first amino acid sequence 95% or more identical to a second amino acid sequence of amino acid residues 1 to 756 of SEQ ID NO:2 wherein said polypeptide has DNA mismatch repair activity.

12. The isolated polypeptide of claim 11 wherein said first amino acid sequence comprises a heterologous polypeptide.

13. The isolated polypeptide of claim 11 which is glycosylated.

14. A composition comprising the isolated polypeptide of claim 11 and a carrier.

15. A polypeptide produced by a method comprising:
(a) culturing a host cell under conditions suitable to produce the isolated polypeptide of claim 11, wherein said host cell comprises a polynucleotide which encodes said polypeptide; and
(b) recovering the polypeptide.

16. An isolated polypeptide comprising a first amino acid sequence 95% or more identical to the full-length polypeptide encoded by the cDNA clone contained in ATCC Deposit No. 75649 wherein said polypeptide has DNA mismatch repair activity.

17. The isolated polypeptide of claim 16 wherein said first amino acid sequence comprises a heterologous polypeptide.

18. The isolated polypeptide of claim 16, which is glycosylated.

19. A composition comprising the isolated polypeptide of claim 16 and a carrier.

20. A polypeptide produced by a method comprising:
(a) culturing a host cell under conditions suitable to produce the isolated polypeptide of claim 16, wherein said host cell comprises a polynucleotide which encodes said polypeptide; and
(b) recovering the polypeptide.

21. An isolated polypeptide comprising an amino acid sequence selected from the group consisting of:
(a) an amino acid sequence of amino acid residues 1 to 932 of SEQ ID NO:4; and
(b) an amino acid sequence of a fragment of SEQ ID NO:4, wherein the fragment has DNA mismatch repair activity.

22. The isolated polypeptide of claim 21 which comprises the amino acid sequence of (a).

23. The isolated polypeptide of claim 21 which comprises the amino acid sequence of (b).

24. The isolated polypeptide of claim 21 wherein said amino acid sequence comprises a heterologous polypeptide.

25. The isolated polypeptide of claim 21 which is glycosylated.

26. A composition comprising the isolated polypeptide of claim 21 and a carrier.

27. A polypeptide produced by a method comprising:
(a) culturing a host cell under conditions suitable to produce the isolated polypeptide of claim 21, wherein said host cell comprises a polynucleotide which encodes said polypeptide; and
(b) recovering the polypeptide.

28. An isolated polypeptide comprising an amino acid sequence selected from the following:
(a) an amino acid sequence of the full-length polypeptide encoded by the cDNA clone contained in ATCC Deposit No. 75651; and
(b) an amino acid sequence of a fragment of the full-length polypeptide encoded by the cDNA clone contained in ATCC Deposit No. 75651 wherein said fragment has DNA mismatch repair activity.

29. The isolated polypeptide of claim 28 which comprises the amino acid sequence of (a).

30. The isolated polypeptide of claim 28 which comprises the amino acid sequence of (b).

31. The isolated polypeptide of claim 28 wherein said amino acid sequence comprises a heterologous polypeptide.

32. The isolated polypeptide of claim 28 which is glycosylated.

33. A composition comprising the isolated polypeptide of claim 28 and a carrier.

34. A polypeptide produced by a method comprising:
(a) culturing a host cell under conditions suitable to produce the isolated polypeptide of claim 28, wherein said host cell comprises a polynucleotide which encodes said polypeptide; and
(b) recovering the polypeptide.

35. An isolated polypeptide comprising a first amino acid sequence 95% or more identical to a second amino acid sequence selected from the group consisting of:
(a) an amino acid sequence of amino acid residues 1 to 932 of SEQ ID NO:4; and
(b) an amino acid sequence of a fragment of SEQ ID NO:4, wherein the fragment has DNA mismatch repair activity;
and wherein said polypeptide has DNA mismatch repair activity.

36. The isolated polypeptide of claim 35 wherein said second amino acid sequence comprises (a).

37. The isolated polypeptide of claim 35 wherein said second amino acid sequence comprises (b).

38. The isolated polypeptide of claim 35 wherein said first amino acid sequence comprises a heterologous polypeptide.

39. The isolated polypeptide of claim 35 which is glycosylated.

40. A composition comprising the isolated polypeptide of claim 35 and a carrier.

41. A polypeptide produced by a method comprising:
(a) culturing a host cell under conditions suitable to produce the isolated polypeptide of claim 35, wherein said host cell comprises a polynucleotide which encodes said polypeptide; and
(b) recovering the polypeptide.

42. An isolated polypeptide comprising a first amino acid sequence 95% or more identical to a second amino acid sequence selected from the following:
(a) an amino acid sequence of the full-length polypeptide encoded by the cDNA clone contained in ATCC Deposit No. 75651; and
(b) an amino acid sequence of a fragment of the full-length polypeptide encoded by the cDNA clone contained in ATCC Deposit No. 75651 wherein said fragment has DNA mismatch repair activity;
and wherein said polypeptide has DNA mismatch repair activity.

43. The isolated polypeptide of claim 42 wherein said second amino acid sequence comprises (a).

44. The isolated polypeptide of claim 42 wherein said second amino acid sequence comprises (b).

45. The isolated polypeptide of claim 42 wherein said first amino acid sequence comprises a heterologous polypeptide.

46. The isolated polypeptide of claim 42, which is glycosylated.

47. A composition comprising the isolated polypeptide of claim 42 and a carrier.

48. A polypeptide produced by a method comprising:
(a) culturing a host cell under conditions suitable to produce the isolated polypeptide of claim 42, wherein said host cell comprises a polynucleotide which encodes said polypeptide; and
(b) recovering the polypeptide.

* * * * *

UNITED STATES PATENT AND TRADEMARK OFFICE
CERTIFICATE OF CORRECTION

PATENT NO. : 6,416,984 B1
DATED : July 9, 2002
INVENTOR(S) : Haseltine et al.

It is certified that error appears in the above-identified patent and that said Letters Patent is hereby corrected as shown below:

<u>Title page,</u>
Item [56], References Cited, OTHER PUBLICATIONS, please correct the following references:
8th reference, please delete "08/259,370" and replace with -- 08/259,310 --.
14th reference, please delete "AAT26925" and replace with -- AAT29625 --.
15th reference, please delete "AAT26926" and replace with -- AAT29626 --.
16th reference, please delete "AAT26927" and replace with -- AAT29627 --.
17th reference, please delete "AAT26928" and replace with -- AAT29628 --.

Signed and Sealed this

Thirty-first Day of December, 2002

JAMES E. ROGAN
*Director of the United States Patent and Trademark Office*

SEQUENCE LISTING

```
<160> NUMBER OF SEQ ID NOS: 78

<210> SEQ ID NO 1
<211> LENGTH: 2525
<212> TYPE: DNA
<213> ORGANISM: homo sapiens
<220> FEATURE:
<221> NAME/KEY: CDS
```

<222> LOCATION: (42)..(2312)

<400> SEQUENCE: 1

| | | |
|---|---|---|
| gttgaacatc tagacgtttc cttggctctt ctggcgccaa a atg tcg ttc gtg gca<br>                                                                         Met Ser Phe Val Ala<br>                                                                          1             5 | 56 |

```
ggg gtt att cgg cgg ctg gac gag aca gtg gtg aac cgc atc gcg gcg        104
Gly Val Ile Arg Arg Leu Asp Glu Thr Val Val Asn Arg Ile Ala Ala
             10                  15                  20 ggg gaa gtt atc cag cgg cca gct aat gct atc aaa gag atg att gag        152
Gly Glu Val Ile Gln Arg Pro Ala Asn Ala Ile Lys Glu Met Ile Glu
         25                  30                  35 aac tgt tta gat gca aaa tcc aca agt att caa gtg att gtt aaa gag        200
Asn Cys Leu Asp Ala Lys Ser Thr Ser Ile Gln Val Ile Val Lys Glu
     40                  45                  50 gga ggc ctg aag ttg att cag atc caa gac aat ggc acc ggg atc agg        248
Gly Gly Leu Lys Leu Ile Gln Ile Gln Asp Asn Gly Thr Gly Ile Arg
 55                  60                  65 aaa gaa gat ctg gat att gta tgt gaa agg ttc act act agt aaa ctg        296
Lys Glu Asp Leu Asp Ile Val Cys Glu Arg Phe Thr Thr Ser Lys Leu
70                  75                  80                  85 cag tcc ttt gag gat tta gcc agt att tct acc tat ggc ttt cga ggt        344
Gln Ser Phe Glu Asp Leu Ala Ser Ile Ser Thr Tyr Gly Phe Arg Gly
                 90                  95                 100 gag gct ttg gcc agc ata agc cat gtg gct cat gtt act att aca acg        392
Glu Ala Leu Ala Ser Ile Ser His Val Ala His Val Thr Ile Thr Thr
            105                 110                 115 aaa aca gct gat gga aag tgt gca tac aga gca agt tac tca gat gga        440
Lys Thr Ala Asp Gly Lys Cys Ala Tyr Arg Ala Ser Tyr Ser Asp Gly
        120                 125                 130 aaa ctg aaa gcc cct cct aaa cca tgt gct ggc aat caa ggg acc cag        488
Lys Leu Lys Ala Pro Pro Lys Pro Cys Ala Gly Asn Gln Gly Thr Gln
    135                 140                 145 atc acg gtg gag gac ctt ttt tac aac ata gcc acg agg aga aaa gct        536
Ile Thr Val Glu Asp Leu Phe Tyr Asn Ile Ala Thr Arg Arg Lys Ala
150                 155                 160                 165 tta aaa aat cca agt gaa gaa tat ggg aaa att ttg gaa gtt gtt ggc        584
Leu Lys Asn Pro Ser Glu Glu Tyr Gly Lys Ile Leu Glu Val Val Gly
                170                 175                 180 agg tat tca gta cac aat gca ggc att agt ttc tca gtt aaa aaa caa        632
Arg Tyr Ser Val His Asn Ala Gly Ile Ser Phe Ser Val Lys Lys Gln
            185                 190                 195 gga gag aca gta gct gat gtt agg aca cta ccc aat gcc tca acc gtg        680
Gly Glu Thr Val Ala Asp Val Arg Thr Leu Pro Asn Ala Ser Thr Val
        200                 205                 210 gac aat att cgc tcc gtc ttt gga aat gct gtt agt cga gaa ctg ata        728
Asp Asn Ile Arg Ser Val Phe Gly Asn Ala Val Ser Arg Glu Leu Ile
    215                 220                 225 gaa att gga tgt gag gat aaa acc cta gcc ttc aaa atg aat ggt tac        776
Glu Ile Gly Cys Glu Asp Lys Thr Leu Ala Phe Lys Met Asn Gly Tyr
230                 235                 240                 245 ata tcc aat gca aac tac tca gtg aag aag tgc atc ttc tta ctc ttc        824
Ile Ser Asn Ala Asn Tyr Ser Val Lys Lys Cys Ile Phe Leu Leu Phe
                250                 255                 260 atc aac cat cgt ctg gta gaa tca act tcc ttg aga aaa gcc ata gaa        872
Ile Asn His Arg Leu Val Glu Ser Thr Ser Leu Arg Lys Ala Ile Glu
            265                 270                 275 aca gtg tat gca gcc tat ttg ccc aaa aac aca cac cca ttc ctg tac        920
Thr Val Tyr Ala Ala Tyr Leu Pro Lys Asn Thr His Pro Phe Leu Tyr
        280                 285                 290
```

```
ctc agt tta gaa atc agt ccc cag aat gtg gat gtt aat gtg cac ccc      968
Leu Ser Leu Glu Ile Ser Pro Gln Asn Val Asp Val Asn Val His Pro
    295                 300                 305 aca aag cat gaa gtt cac ttc ctg cac gag gag agc atc ctg gag cgg     1016
Thr Lys His Glu Val His Phe Leu His Glu Glu Ser Ile Leu Glu Arg
310                 315                 320                 325 gtg cag cag cac atc gag agc aag ctc ctg ggc tcc aat tcc tcc agg     1064
Val Gln Gln His Ile Glu Ser Lys Leu Leu Gly Ser Asn Ser Ser Arg
                330                 335                 340 atg tac ttc acc cag act ttg cta cca gga ctt gct ggc ccc tct ggg     1112
Met Tyr Phe Thr Gln Thr Leu Leu Pro Gly Leu Ala Gly Pro Ser Gly
            345                 350                 355 gag atg gtt aaa tcc aca aca agt ctg acc tcg tct tct act tct gga     1160
Glu Met Val Lys Ser Thr Thr Ser Leu Thr Ser Ser Ser Thr Ser Gly
        360                 365                 370 agt agt gat aag gtc tat gcc cac cag atg gtt cgt aca gat tcc cgg     1208
Ser Ser Asp Lys Val Tyr Ala His Gln Met Val Arg Thr Asp Ser Arg
    375                 380                 385 gaa cag aag ctt gat gca ttt ctg cag cct ctg agc aaa ccc ctg tcc     1256
Glu Gln Lys Leu Asp Ala Phe Leu Gln Pro Leu Ser Lys Pro Leu Ser
390                 395                 400                 405 agt cag ccc cag gcc att gtc aca gag gat aag aca gat att tct agt     1304
Ser Gln Pro Gln Ala Ile Val Thr Glu Asp Lys Thr Asp Ile Ser Ser
                410                 415                 420 ggc agg gct agg cag caa gat gag gag atg ctt gaa ctc cca gcc cct     1352
Gly Arg Ala Arg Gln Gln Asp Glu Glu Met Leu Glu Leu Pro Ala Pro
            425                 430                 435 gct gaa gtg gct gcc aaa aat cag agc ttg gag ggg gat aca aca aag     1400
Ala Glu Val Ala Ala Lys Asn Gln Ser Leu Glu Gly Asp Thr Thr Lys
        440                 445                 450 ggg act tca gaa atg tca gag aag aga gga cct act tcc agc aac ccc     1448
Gly Thr Ser Glu Met Ser Glu Lys Arg Gly Pro Thr Ser Ser Asn Pro
    455                 460                 465 aga aag aga cat cgg gaa gat tct gat gtg gaa atg gtg gaa gat gat     1496
Arg Lys Arg His Arg Glu Asp Ser Asp Val Glu Met Val Glu Asp Asp
470                 475                 480                 485 tcc cga aag gaa atg act gca gct tgt acc ccc cgg aga agg atc att     1544
Ser Arg Lys Glu Met Thr Ala Ala Cys Thr Pro Arg Arg Arg Ile Ile
                490                 495                 500 aac ctc act agt gtt ttg agt ctc cag gaa gaa att aat gag cag gga     1592
Asn Leu Thr Ser Val Leu Ser Leu Gln Glu Glu Ile Asn Glu Gln Gly
            505                 510                 515 cat gag gtt ctc cgg gag atg ttg cat aac cac tcc ttc gtg ggc tgt     1640
His Glu Val Leu Arg Glu Met Leu His Asn His Ser Phe Val Gly Cys
        520                 525                 530 gtg aat cct cag tgg gcc ttg gca cag cat caa acc aag tta tac ctt     1688
Val Asn Pro Gln Trp Ala Leu Ala Gln His Gln Thr Lys Leu Tyr Leu
    535                 540                 545 ctc aac acc acc aag ctt agt gaa gaa ctg ttc tac cag ata ctc att     1736
Leu Asn Thr Thr Lys Leu Ser Glu Glu Leu Phe Tyr Gln Ile Leu Ile
550                 555                 560                 565 tat gat ttt gcc aat ttt ggt gtt ctc agg tta tcg gag cca gca ccg     1784
Tyr Asp Phe Ala Asn Phe Gly Val Leu Arg Leu Ser Glu Pro Ala Pro
                570                 575                 580 ctc ttt gac ctt gcc atg ctt gcc tta gat agt cca gag agt ggc tgg     1832
Leu Phe Asp Leu Ala Met Leu Ala Leu Asp Ser Pro Glu Ser Gly Trp
            585                 590                 595 aca gag gaa gat ggt ccc aaa gaa gga ctt gct gaa tac att gtt gag     1880
Thr Glu Glu Asp Gly Pro Lys Glu Gly Leu Ala Glu Tyr Ile Val Glu
```

```
                600              605              610
ttt ctg aag aag aag gct gag atg ctt gca gac tat ttc tct ttg gaa    1928
Phe Leu Lys Lys Lys Ala Glu Met Leu Ala Asp Tyr Phe Ser Leu Glu
        615              620              625 att gat gag gaa ggg aac ctg att gga tta ccc ctt ctg att gac aac    1976
Ile Asp Glu Glu Gly Asn Leu Ile Gly Leu Pro Leu Leu Ile Asp Asn
630              635              640              645 tat gtg ccc cct ttg gag gga ctg cct atc ttc att ctt cga cta gcc    2024
Tyr Val Pro Pro Leu Glu Gly Leu Pro Ile Phe Ile Leu Arg Leu Ala
                650              655              660 act gag gtg aat tgg gac gaa gaa aag gaa tgt ttt gaa agc ctc agt    2072
Thr Glu Val Asn Trp Asp Glu Glu Lys Glu Cys Phe Glu Ser Leu Ser
        665              670              675 aaa gaa tgc gct atg ttc tat tcc atc cgg aag cag tac ata tct gag    2120
Lys Glu Cys Ala Met Phe Tyr Ser Ile Arg Lys Gln Tyr Ile Ser Glu
680              685              690 gag tcg acc ctc tca ggc cag cag agt gaa gtg cct ggc tcc att cca    2168
Glu Ser Thr Leu Ser Gly Gln Gln Ser Glu Val Pro Gly Ser Ile Pro
        695              700              705 aac tcc tgg aag tgg act gtg gaa cac att gtc tat aaa gcc ttg cgc    2216
Asn Ser Trp Lys Trp Thr Val Glu His Ile Val Tyr Lys Ala Leu Arg
710              715              720              725 tca cac att ctg cct cct aaa cat ttc aca gaa gat gga aat atc ctg    2264
Ser His Ile Leu Pro Pro Lys His Phe Thr Glu Asp Gly Asn Ile Leu
                730              735              740 cag ctt gct aac ctg cct gat cta tac aaa gtc ttt gag agg tgt taa    2312
Gln Leu Ala Asn Leu Pro Asp Leu Tyr Lys Val Phe Glu Arg Cys
        745              750              755 atatggttat ttatgcactg tgggatgtgt tcttctttct ctgtattccg atacaaagtg    2372
ttgtatcaaa gtgtgatata caaagtgtac aacataagt gttggtagca cttaagactt    2432
atacttgcct tctgatagta ttcctttata cacagtggat tgattataaa taaatagatg    2492
tgtcttaaca taaaaaaaaa aaaaaaaaaa aaa                                 2525

<210> SEQ ID NO 2
<211> LENGTH: 756
<212> TYPE: PRT
<213> ORGANISM: homo sapiens

<400> SEQUENCE: 2

Met Ser Phe Val Ala Gly Val Ile Arg Arg Leu Asp Glu Thr Val Val
1               5                  10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
```

```
            130                 135                 140
Asn Gln Gly Thr Gln Ile Thr Val Glu Asp Leu Phe Tyr Asn Ile Ala
145                 150                 155                 160
Thr Arg Arg Lys Ala Leu Lys Asn Pro Ser Glu Glu Tyr Gly Lys Ile
                165                 170                 175
Leu Glu Val Val Gly Arg Tyr Ser Val His Asn Ala Gly Ile Ser Phe
            180                 185                 190
Ser Val Lys Lys Gln Gly Glu Thr Val Ala Asp Val Arg Thr Leu Pro
        195                 200                 205
Asn Ala Ser Thr Val Asp Asn Ile Arg Ser Val Phe Gly Asn Ala Val
210                 215                 220
Ser Arg Glu Leu Ile Glu Ile Gly Cys Glu Asp Lys Thr Leu Ala Phe
225                 230                 235                 240
Lys Met Asn Gly Tyr Ile Ser Asn Ala Asn Tyr Ser Val Lys Lys Cys
                245                 250                 255
Ile Phe Leu Leu Phe Ile Asn His Arg Leu Val Glu Ser Thr Ser Leu
            260                 265                 270
Arg Lys Ala Ile Glu Thr Val Tyr Ala Ala Tyr Leu Pro Lys Asn Thr
        275                 280                 285
His Pro Phe Leu Tyr Leu Ser Leu Glu Ile Ser Pro Gln Asn Val Asp
290                 295                 300
Val Asn Val His Pro Thr Lys His Glu Val His Phe Leu His Glu Glu
305                 310                 315                 320
Ser Ile Leu Glu Arg Val Gln Gln His Ile Glu Ser Lys Leu Leu Gly
                325                 330                 335
Ser Asn Ser Ser Arg Met Tyr Phe Thr Gln Thr Leu Leu Pro Gly Leu
            340                 345                 350
Ala Gly Pro Ser Gly Glu Met Val Lys Ser Thr Thr Ser Leu Thr Ser
        355                 360                 365
Ser Ser Thr Ser Gly Ser Ser Asp Lys Val Tyr Ala His Gln Met Val
370                 375                 380
Arg Thr Asp Ser Arg Glu Gln Lys Leu Asp Ala Phe Leu Gln Pro Leu
385                 390                 395                 400
Ser Lys Pro Leu Ser Ser Gln Pro Gln Ala Ile Val Thr Glu Asp Lys
                405                 410                 415
Thr Asp Ile Ser Ser Gly Arg Ala Arg Gln Gln Asp Glu Glu Met Leu
            420                 425                 430
Glu Leu Pro Ala Pro Ala Glu Val Ala Ala Lys Asn Gln Ser Leu Glu
        435                 440                 445
Gly Asp Thr Thr Lys Gly Thr Ser Glu Met Ser Glu Lys Arg Gly Pro
450                 455                 460
Thr Ser Ser Asn Pro Arg Lys Arg His Arg Glu Asp Ser Asp Val Glu
465                 470                 475                 480
Met Val Glu Asp Asp Ser Arg Lys Glu Met Thr Ala Ala Cys Thr Pro
                485                 490                 495
Arg Arg Arg Ile Ile Asn Leu Thr Ser Val Leu Ser Leu Gln Glu Glu
            500                 505                 510
Ile Asn Glu Gln Gly His Glu Val Leu Arg Glu Met Leu His Asn His
        515                 520                 525
Ser Phe Val Gly Cys Val Asn Pro Gln Trp Ala Leu Ala Gln His Gln
530                 535                 540
Thr Lys Leu Tyr Leu Leu Asn Thr Thr Lys Leu Ser Glu Glu Leu Phe
545                 550                 555                 560
```

```
Tyr Gln Ile Leu Ile Tyr Asp Phe Ala Asn Phe Gly Val Leu Arg Leu
            565                 570                 575

Ser Glu Pro Ala Pro Leu Phe Asp Leu Ala Met Leu Ala Leu Asp Ser
        580                 585                 590

Pro Glu Ser Gly Trp Thr Glu Asp Gly Pro Lys Glu Gly Leu Ala
        595                 600                 605

Glu Tyr Ile Val Glu Phe Leu Lys Lys Lys Ala Glu Met Leu Ala Asp
        610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
        690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
                740                 745                 750

Phe Glu Arg Cys
        755

<210> SEQ ID NO 3
<211> LENGTH: 3063
<212> TYPE: DNA
<213> ORGANISM: homo sapiens
<220> FEATURE:
<221> NAME/KEY: CDS
<222> LOCATION: (81)..(2879)

<400> SEQUENCE: 3
ggcacgagtg gctgcttgcg gctagtggat ggtaattgcc tgcctcgcgc tagcagcaag      60
ctgctctgtt aaaagcgaaa atg aaa caa ttg cct gcg gca aca gtt cga ctc    113
                     Met Lys Gln Leu Pro Ala Ala Thr Val Arg Leu
                       1               5                  10 ctt tca agt tct cag atc atc act tcg gtg gtc agt gtt gta aaa gag    161
Leu Ser Ser Ser Gln Ile Ile Thr Ser Val Val Ser Val Val Lys Glu
            15                  20                  25 ctt att gaa aac tcc ttg gat gct ggt gcc aca agc gta gat gtt aaa    209
Leu Ile Glu Asn Ser Leu Asp Ala Gly Ala Thr Ser Val Asp Val Lys
        30                  35                  40 ctg gag aac tat gga ttt gat aaa att gag gtg cga gat aac ggg gag    257
Leu Glu Asn Tyr Gly Phe Asp Lys Ile Glu Val Arg Asp Asn Gly Glu
    45                  50                  55 ggt atc aag gct gtt gat gca cct gta atg gca atg aag tac tac acc    305
Gly Ile Lys Ala Val Asp Ala Pro Val Met Ala Met Lys Tyr Tyr Thr
60                  65                  70                  75 tca aaa ata aat agt cat gaa gat ctt gaa aat ttg aca act tac ggt    353
Ser Lys Ile Asn Ser His Glu Asp Leu Glu Asn Leu Thr Thr Tyr Gly
                80                  85                  90 ttt cgt gga gaa gcc ttg ggg tca att tgt tgt ata gct gag gtt tta    401
Phe Arg Gly Glu Ala Leu Gly Ser Ile Cys Cys Ile Ala Glu Val Leu
```

| | | | | | | | | | | | | | | |
|---|---|---|---|---|---|---|---|---|---|---|---|---|---|---|
| | | | 95 | | | | 100 | | | | 105 | | | |
| att | aca | aca | aga | acg | gct | gct | gat | aat | ttt | agc | acc | cag | tat | gtt | tta | 449 |
| Ile | Thr | Thr | Arg | Thr | Ala | Ala | Asp | Asn | Phe | Ser | Thr | Gln | Tyr | Val | Leu | |
| | | 110 | | | | | 115 | | | | | 120 | | | |

| gat | ggc | agt | ggc | cac | ata | ctt | tct | cag | aaa | cct | tca | cat | ctt | ggt | caa | 497 |
| Asp | Gly | Ser | Gly | His | Ile | Leu | Ser | Gln | Lys | Pro | Ser | His | Leu | Gly | Gln | |
| | 125 | | | | | 130 | | | | | 135 | | | | |

| ggt | aca | act | gta | act | gct | tta | aga | tta | ttt | aag | aat | cta | cct | gta | aga | 545 |
| Gly | Thr | Thr | Val | Thr | Ala | Leu | Arg | Leu | Phe | Lys | Asn | Leu | Pro | Val | Arg | |
| 140 | | | | | 145 | | | | | 150 | | | | | 155 |

| aag | cag | ttt | tac | tca | act | gca | aaa | aaa | tgt | aaa | gat | gaa | ata | aaa | aag | 593 |
| Lys | Gln | Phe | Tyr | Ser | Thr | Ala | Lys | Lys | Cys | Lys | Asp | Glu | Ile | Lys | Lys | |
| | | | | 160 | | | | | 165 | | | | | 170 | | |

| atc | caa | gat | ctc | ctc | atg | agc | ttt | ggt | atc | ctt | aaa | cct | gac | tta | agg | 641 |
| Ile | Gln | Asp | Leu | Leu | Met | Ser | Phe | Gly | Ile | Leu | Lys | Pro | Asp | Leu | Arg | |
| | | | | 175 | | | | | 180 | | | | | 185 | | |

| att | gtc | ttt | gta | cat | aac | aag | gca | gtt | att | tgg | cag | aaa | agc | aga | gta | 689 |
| Ile | Val | Phe | Val | His | Asn | Lys | Ala | Val | Ile | Trp | Gln | Lys | Ser | Arg | Val | |
| | | | 190 | | | | | 195 | | | | | 200 | | | |

| tca | gat | cac | aag | atg | gct | ctc | atg | tca | gtt | ctg | ggg | act | gct | gtt | atg | 737 |
| Ser | Asp | His | Lys | Met | Ala | Leu | Met | Ser | Val | Leu | Gly | Thr | Ala | Val | Met | |
| | 205 | | | | | 210 | | | | | 215 | | | | |

| aac | aat | atg | gaa | tcc | ttt | cag | tac | cac | tct | gaa | gaa | tct | cag | att | tat | 785 |
| Asn | Asn | Met | Glu | Ser | Phe | Gln | Tyr | His | Ser | Glu | Glu | Ser | Gln | Ile | Tyr | |
| 220 | | | | | 225 | | | | | 230 | | | | | 235 |

| ctc | agt | gga | ttt | ctt | cca | aag | tgt | gat | gca | gac | cac | tct | ttc | act | agt | 833 |
| Leu | Ser | Gly | Phe | Leu | Pro | Lys | Cys | Asp | Ala | Asp | His | Ser | Phe | Thr | Ser | |
| | | | | 240 | | | | | 245 | | | | | 250 | | |

| ctt | tca | aca | cca | gaa | aga | agt | ttc | atc | ttc | ata | aac | agt | cga | cca | gta | 881 |
| Leu | Ser | Thr | Pro | Glu | Arg | Ser | Phe | Ile | Phe | Ile | Asn | Ser | Arg | Pro | Val | |
| | | | | 255 | | | | | 260 | | | | | 265 | | |

| cat | caa | aaa | gat | atc | tta | aag | tta | atc | cga | cat | cat | tac | aat | ctg | aaa | 929 |
| His | Gln | Lys | Asp | Ile | Leu | Lys | Leu | Ile | Arg | His | His | Tyr | Asn | Leu | Lys | |
| | | 270 | | | | | 275 | | | | | 280 | | | | |

| tgc | cta | aag | gaa | tct | act | cgt | ttg | tat | cct | gtt | ttc | ttt | ctg | aaa | atc | 977 |
| Cys | Leu | Lys | Glu | Ser | Thr | Arg | Leu | Tyr | Pro | Val | Phe | Phe | Leu | Lys | Ile | |
| | 285 | | | | | 290 | | | | | 295 | | | | |

| gat | gtt | cct | aca | gct | gat | gtt | gat | gta | aat | tta | aca | cca | gat | aaa | agc | 1025 |
| Asp | Val | Pro | Thr | Ala | Asp | Val | Asp | Val | Asn | Leu | Thr | Pro | Asp | Lys | Ser | |
| 300 | | | | | 305 | | | | | 310 | | | | | 315 |

| caa | gta | tta | tta | caa | aat | aag | gaa | tct | gtt | tta | att | gct | ctt | gaa | aat | 1073 |
| Gln | Val | Leu | Leu | Gln | Asn | Lys | Glu | Ser | Val | Leu | Ile | Ala | Leu | Glu | Asn | |
| | | | 320 | | | | | 325 | | | | | 330 | | | |

| ctg | atg | acg | act | tgt | tat | gga | cca | tta | cct | agt | aca | aat | tct | tat | gaa | 1121 |
| Leu | Met | Thr | Thr | Cys | Tyr | Gly | Pro | Leu | Pro | Ser | Thr | Asn | Ser | Tyr | Glu | |
| | | | 335 | | | | | 340 | | | | | 345 | | | |

| aat | aat | aaa | aca | gat | gtt | tcc | gca | gct | gac | atc | gtt | ctt | agt | aaa | aca | 1169 |
| Asn | Asn | Lys | Thr | Asp | Val | Ser | Ala | Ala | Asp | Ile | Val | Leu | Ser | Lys | Thr | |
| | | 350 | | | | | 355 | | | | | 360 | | | | |

| gca | gaa | aca | gat | gtg | ctt | ttt | aat | aaa | gtg | gaa | tca | tct | gga | aag | aat | 1217 |
| Ala | Glu | Thr | Asp | Val | Leu | Phe | Asn | Lys | Val | Glu | Ser | Ser | Gly | Lys | Asn | |
| | 365 | | | | | 370 | | | | | 375 | | | | |

| tat | tca | aat | gtt | gat | act | tca | gtc | att | cca | ttc | caa | aat | gat | atg | cat | 1265 |
| Tyr | Ser | Asn | Val | Asp | Thr | Ser | Val | Ile | Pro | Phe | Gln | Asn | Asp | Met | His | |
| 380 | | | | | 385 | | | | | 390 | | | | | 395 |

| aat | gat | gaa | tct | gga | aaa | aac | act | gat | gat | tgt | tta | aat | cac | cag | ata | 1313 |
| Asn | Asp | Glu | Ser | Gly | Lys | Asn | Thr | Asp | Asp | Cys | Leu | Asn | His | Gln | Ile | |
| | | | | 400 | | | | | 405 | | | | | 410 | |

| agt | att | ggt | gac | ttt | ggt | tat | ggt | cat | tgt | agt | agt | gaa | att | tct | aac | 1361 |

```
Ser Ile Gly Asp Phe Gly Tyr Gly His Cys Ser Ser Glu Ile Ser Asn
            415                 420                 425 att gat aaa aac act aag aat gca ttt cag gac att tca atg agt aat    1409
Ile Asp Lys Asn Thr Lys Asn Ala Phe Gln Asp Ile Ser Met Ser Asn
430                 435                 440 gta tca tgg gag aac tct cag acg gaa tat agt aaa act tgt ttt ata    1457
Val Ser Trp Glu Asn Ser Gln Thr Glu Tyr Ser Lys Thr Cys Phe Ile
        445                 450                 455 agt tcc gtt aag cac acc cag tca gaa aat ggc aat aaa gac cat ata    1505
Ser Ser Val Lys His Thr Gln Ser Glu Asn Gly Asn Lys Asp His Ile
460                 465                 470                 475 gat gag agt ggg gaa aat gag gaa gca ggt ctt gaa aac tct tcg        1553
Asp Glu Ser Gly Glu Asn Glu Glu Ala Gly Leu Glu Asn Ser Ser
                480                 485                 490 gaa att tct gca gat gag tgg agc agg gga aat ata ctt aaa aat tca    1601
Glu Ile Ser Ala Asp Glu Trp Ser Arg Gly Asn Ile Leu Lys Asn Ser
            495                 500                 505 gtg gga gag aat att gaa cct gtg aaa att tta gtg cct gaa aaa agt    1649
Val Gly Glu Asn Ile Glu Pro Val Lys Ile Leu Val Pro Glu Lys Ser
        510                 515                 520 tta cca tgt aaa gta agt aat aat aat tat cca atc cct gaa caa atg    1697
Leu Pro Cys Lys Val Ser Asn Asn Asn Tyr Pro Ile Pro Glu Gln Met
525                 530                 535 aat ctt aat gaa gat tca tgt aac aaa aaa tca aat gta ata gat aat    1745
Asn Leu Asn Glu Asp Ser Cys Asn Lys Lys Ser Asn Val Ile Asp Asn
540                 545                 550                 555 aaa tct gga aaa gtt aca gct tat gat tta ctt agc aat cga gta atc    1793
Lys Ser Gly Lys Val Thr Ala Tyr Asp Leu Leu Ser Asn Arg Val Ile
                560                 565                 570 aag aaa ccc atg tca gca agt gct ctt ttt gtt caa gat cat cgt cct    1841
Lys Lys Pro Met Ser Ala Ser Ala Leu Phe Val Gln Asp His Arg Pro
            575                 580                 585 cag ttt ctc ata gaa aat cct aag act agt tta gag gat gca aca cta    1889
Gln Phe Leu Ile Glu Asn Pro Lys Thr Ser Leu Glu Asp Ala Thr Leu
        590                 595                 600 caa att gaa gaa ctg tgg aag aca ttg agt gaa gag gaa aaa ctg aaa    1937
Gln Ile Glu Glu Leu Trp Lys Thr Leu Ser Glu Glu Glu Lys Leu Lys
    605                 610                 615 tat gaa gag aag gct act aaa gac ttg gaa cga tac aat agt caa atg    1985
Tyr Glu Glu Lys Ala Thr Lys Asp Leu Glu Arg Tyr Asn Ser Gln Met
620                 625                 630                 635 aag aga gcc att gaa cag gag tca caa atg tca cta aaa gat ggc aga    2033
Lys Arg Ala Ile Glu Gln Glu Ser Gln Met Ser Leu Lys Asp Gly Arg
                640                 645                 650 aaa aag ata aaa ccc acc agc gca tgg aat ttg gcc cag aag cac aag    2081
Lys Lys Ile Lys Pro Thr Ser Ala Trp Asn Leu Ala Gln Lys His Lys
            655                 660                 665 tta aaa acc tca tta tct aat caa cca aaa ctt gat gaa ctc ctt cag    2129
Leu Lys Thr Ser Leu Ser Asn Gln Pro Lys Leu Asp Glu Leu Leu Gln
        670                 675                 680 tcc caa att gaa aaa aga agg agt caa aat att aaa atg gta cag atc    2177
Ser Gln Ile Glu Lys Arg Arg Ser Gln Asn Ile Lys Met Val Gln Ile
    685                 690                 695 ccc ttt tct atg aaa aac tta aaa ata aat ttt aag aaa caa aac aaa    2225
Pro Phe Ser Met Lys Asn Leu Lys Ile Asn Phe Lys Lys Gln Asn Lys
700                 705                 710                 715 gtt gac tta gaa gag aag gat gaa cct tgc ttg atc cac aat ctc agg    2273
Val Asp Leu Glu Glu Lys Asp Glu Pro Cys Leu Ile His Asn Leu Arg
                720                 725                 730
```

-continued

```
ttt cct gat gca tgg cta atg aca tcc aaa aca gag gta atg tta tta    2321
Phe Pro Asp Ala Trp Leu Met Thr Ser Lys Thr Glu Val Met Leu Leu
            735                 740                 745 aat cca tat aga gta gaa gaa gcc ctg cta ttt aaa aga ctt ctt gag    2369
Asn Pro Tyr Arg Val Glu Glu Ala Leu Leu Phe Lys Arg Leu Leu Glu
        750                 755                 760 aat cat aaa ctt cct gca gag cca ctg gaa aag cca att atg tta aca    2417
Asn His Lys Leu Pro Ala Glu Pro Leu Glu Lys Pro Ile Met Leu Thr
    765                 770                 775 gag agt ctt ttt aat gga tct cat tat tta gac gtt tta tat aaa atg    2465
Glu Ser Leu Phe Asn Gly Ser His Tyr Leu Asp Val Leu Tyr Lys Met
780                 785                 790                 795 aca gca gat gac caa aga tac agt gga tca act tac ctg tct gat cct    2513
Thr Ala Asp Asp Gln Arg Tyr Ser Gly Ser Thr Tyr Leu Ser Asp Pro
                800                 805                 810 cgt ctt aca gcg aat ggt ttc aag ata aaa ttg ata cca gga gtt tca    2561
Arg Leu Thr Ala Asn Gly Phe Lys Ile Lys Leu Ile Pro Gly Val Ser
            815                 820                 825 att act gaa aat tac ttg gaa ata gaa gga atg gct aat tgt ctc cca    2609
Ile Thr Glu Asn Tyr Leu Glu Ile Glu Gly Met Ala Asn Cys Leu Pro
        830                 835                 840 ttc tat gga gta gca gat tta aaa gaa att ctt aat gct ata tta aac    2657
Phe Tyr Gly Val Ala Asp Leu Lys Glu Ile Leu Asn Ala Ile Leu Asn
    845                 850                 855 aga aat gca aag gaa gtt tat gaa tgt aga cct cgc aaa gtg ata agt    2705
Arg Asn Ala Lys Glu Val Tyr Glu Cys Arg Pro Arg Lys Val Ile Ser
860                 865                 870                 875 tat tta gag gga gaa gca gtg cgt cta tcc aga caa tta ccc atg tac    2753
Tyr Leu Glu Gly Glu Ala Val Arg Leu Ser Arg Gln Leu Pro Met Tyr
                880                 885                 890 tta tca aaa gag gac atc caa gac att atc tac aga atg aag cac cag    2801
Leu Ser Lys Glu Asp Ile Gln Asp Ile Ile Tyr Arg Met Lys His Gln
            895                 900                 905 ttt gga aat gaa att aaa gag tgt gtt cat ggt cgc cca ttt ttt cat    2849
Phe Gly Asn Glu Ile Lys Glu Cys Val His Gly Arg Pro Phe Phe His
        910                 915                 920 cat tta acc tat ctt cca gaa act aca tga ttaaatatgt ttaagaagat      2899
His Leu Thr Tyr Leu Pro Glu Thr Thr
    925                 930 tagttaccat tgaaattggt tctgtcataa aacagcatga gtctggtttt aaattatctt  2959
tgtattatgt gtcacatggt tatttttaa atgaggattc actgacttgt ttttatattg   3019
aaaaaagttc cacgtattgt agaaaacgta aataaactaa taac                   3063
```

<210> SEQ ID NO 4
<211> LENGTH: 932
<212> TYPE: PRT
<213> ORGANISM: homo sapiens

<400> SEQUENCE: 4

```
Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
```

```
                65                  70                  75                  80

His Glu Asp Leu Glu Asn Leu Thr Thr Tyr Gly Phe Arg Gly Glu Ala
                    85                  90                  95

Leu Gly Ser Ile Cys Cys Ile Ala Glu Val Leu Ile Thr Thr Arg Thr
                100                 105                 110

Ala Ala Asp Asn Phe Ser Thr Gln Tyr Val Leu Asp Gly Ser Gly His
                115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
                180                 185                 190

Asn Lys Ala Val Ile Trp Gln Lys Ser Arg Val Ser Asp His Lys Met
    195                 200                 205

Ala Leu Met Ser Val Leu Gly Thr Ala Val Met Asn Asn Met Glu Ser
    210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
                260                 265                 270

Leu Lys Leu Ile Arg His His Tyr Asn Leu Lys Cys Leu Lys Glu Ser
    275                 280                 285

Thr Arg Leu Tyr Pro Val Phe Phe Leu Lys Ile Asp Val Pro Thr Ala
    290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
                340                 345                 350

Val Ser Ala Ala Asp Ile Val Leu Ser Lys Thr Ala Glu Thr Asp Val
    355                 360                 365

Leu Phe Asn Lys Val Glu Ser Ser Gly Lys Asn Tyr Ser Asn Val Asp
    370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
                420                 425                 430

Lys Asn Ala Phe Gln Asp Ile Ser Met Ser Asn Val Ser Trp Glu Asn
    435                 440                 445

Ser Gln Thr Glu Tyr Ser Lys Thr Cys Phe Ile Ser Ser Val Lys His
    450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495
```

-continued

```
Glu Trp Ser Arg Gly Asn Ile Leu Lys Asn Ser Val Gly Glu Asn Ile
            500                 505                 510
Glu Pro Val Lys Ile Leu Val Pro Glu Lys Ser Leu Pro Cys Lys Val
            515                 520                 525
Ser Asn Asn Tyr Pro Ile Pro Glu Gln Met Asn Leu Asn Glu Asp
    530                 535                 540
Ser Cys Asn Lys Lys Ser Asn Val Ile Asp Asn Lys Ser Gly Lys Val
545                 550                 555                 560
Thr Ala Tyr Asp Leu Leu Ser Asn Arg Val Ile Lys Lys Pro Met Ser
                565                 570                 575
Ala Ser Ala Leu Phe Val Gln Asp His Arg Pro Gln Phe Leu Ile Glu
            580                 585                 590
Asn Pro Lys Thr Ser Leu Glu Asp Ala Thr Leu Gln Ile Glu Glu Leu
            595                 600                 605
Trp Lys Thr Leu Ser Glu Glu Lys Leu Lys Tyr Glu Glu Lys Ala
            610                 615                 620
Thr Lys Asp Leu Glu Arg Tyr Asn Ser Gln Met Lys Arg Ala Ile Glu
625                 630                 635                 640
Gln Glu Ser Gln Met Ser Leu Lys Asp Gly Arg Lys Lys Ile Lys Pro
                645                 650                 655
Thr Ser Ala Trp Asn Leu Ala Gln Lys His Lys Leu Lys Thr Ser Leu
            660                 665                 670
Ser Asn Gln Pro Lys Leu Asp Glu Leu Leu Gln Ser Gln Ile Glu Lys
            675                 680                 685
Arg Arg Ser Gln Asn Ile Lys Met Val Gln Ile Pro Phe Ser Met Lys
690                 695                 700
Asn Leu Lys Ile Asn Phe Lys Lys Gln Asn Lys Val Asp Leu Glu Glu
705                 710                 715                 720
Lys Asp Glu Pro Cys Leu Ile His Asn Leu Arg Phe Pro Asp Ala Trp
                725                 730                 735
Leu Met Thr Ser Lys Thr Glu Val Met Leu Leu Asn Pro Tyr Arg Val
            740                 745                 750
Glu Glu Ala Leu Leu Phe Lys Arg Leu Leu Glu Asn His Lys Leu Pro
            755                 760                 765
Ala Glu Pro Leu Glu Lys Pro Ile Met Leu Thr Glu Ser Leu Phe Asn
            770                 775                 780
Gly Ser His Tyr Leu Asp Val Leu Tyr Lys Met Thr Ala Asp Asp Gln
785                 790                 795                 800
Arg Tyr Ser Gly Ser Thr Tyr Leu Ser Asp Pro Arg Leu Thr Ala Asn
                805                 810                 815
Gly Phe Lys Ile Lys Leu Ile Pro Gly Val Ser Ile Thr Glu Asn Tyr
            820                 825                 830
Leu Glu Ile Glu Gly Met Ala Asn Cys Leu Pro Phe Tyr Gly Val Ala
            835                 840                 845
Asp Leu Lys Glu Ile Leu Asn Ala Ile Leu Asn Arg Asn Ala Lys Glu
            850                 855                 860
Val Tyr Glu Cys Arg Pro Arg Lys Val Ile Ser Tyr Leu Glu Gly Glu
865                 870                 875                 880
Ala Val Arg Leu Ser Arg Gln Leu Pro Met Tyr Leu Ser Lys Glu Asp
                885                 890                 895
Ile Gln Asp Ile Ile Tyr Arg Met Lys His Gln Phe Gly Asn Glu Ile
            900                 905                 910
```

```
                 Lys Glu Cys Val His Gly Arg Pro Phe Phe His His Leu Thr Tyr Leu
                     915                 920                 925

Pro Glu Thr Thr
    930

<210> SEQ ID NO 5
<211> LENGTH: 2771
<212> TYPE: DNA
<213> ORGANISM: homo sapiens
<220> FEATURE:
<221> NAME/KEY: CDS
<222> LOCATION: (25)..(2613)

<400> SEQUENCE: 5
cgaggcggat cgggtgttgc atcc atg gag cga gct gag agc tcg agt aca         51
                         Met Glu Arg Ala Glu Ser Ser Ser Thr
                           1               5 gaa cct gct aag gcc atc aaa cct att gat cgg aag tca gtc cat cag         99
Glu Pro Ala Lys Ala Ile Lys Pro Ile Asp Arg Lys Ser Val His Gln
 10                  15                  20                  25 att tgc tct ggg cag gtg gta ctg agt cta agc act gcg gta aag gag        147
Ile Cys Ser Gly Gln Val Val Leu Ser Leu Ser Thr Ala Val Lys Glu
                 30                  35                  40 tta gta gaa aac agt ctg gat gct ggt gcc act aat att gat cta aag        195
Leu Val Glu Asn Ser Leu Asp Ala Gly Ala Thr Asn Ile Asp Leu Lys
             45                  50                  55 ctt aag gac tat gga gtg gat ctt att gaa gtt tca gac aat gga tgt        243
Leu Lys Asp Tyr Gly Val Asp Leu Ile Glu Val Ser Asp Asn Gly Cys
         60                  65                  70 ggg gta gaa gaa gaa aac ttc gaa ggc tta act ctg aaa cat cac aca        291
Gly Val Glu Glu Glu Asn Phe Glu Gly Leu Thr Leu Lys His His Thr
     75                  80                  85 tct aag att caa gag ttt gcc gac cta act cag gtt gaa act ttt ggc        339
Ser Lys Ile Gln Glu Phe Ala Asp Leu Thr Gln Val Glu Thr Phe Gly
 90                  95                 100                 105 ttt cgg ggg gaa gct ctg agc tca ctt tgt gca ctg agc gat gtc acc        387
Phe Arg Gly Glu Ala Leu Ser Ser Leu Cys Ala Leu Ser Asp Val Thr
                110                 115                 120 att tct acc tgc cac gca tcg gcg aag gtt gga act cga ctg atg ttt        435
Ile Ser Thr Cys His Ala Ser Ala Lys Val Gly Thr Arg Leu Met Phe
            125                 130                 135 gat cac aat ggg aaa att atc cag aaa acc ccc tac ccc cgc ccc aga        483
Asp His Asn Gly Lys Ile Ile Gln Lys Thr Pro Tyr Pro Arg Pro Arg
        140                 145                 150 ggg acc aca gtc agc gtg cag cag tta ttt tcc aca cta cct gtg cgc        531
Gly Thr Thr Val Ser Val Gln Gln Leu Phe Ser Thr Leu Pro Val Arg
    155                 160                 165 cat aag gaa ttt caa agg aat att aag aag gag tat gcc aaa atg gtc        579
His Lys Glu Phe Gln Arg Asn Ile Lys Lys Glu Tyr Ala Lys Met Val
170                 175                 180                 185 cag gtc tta cat gca tac tgt atc att tca gca ggc atc cgt gta agt        627
Gln Val Leu His Ala Tyr Cys Ile Ile Ser Ala Gly Ile Arg Val Ser
                190                 195                 200 tgc acc aat cag ctt gga caa gga aaa cga cag cct gta gta tgc aca        675
Cys Thr Asn Gln Leu Gly Gln Gly Lys Arg Gln Pro Val Val Cys Thr
            205                 210                 215 ggt gga agc ccc agc ata aag gaa aat atc ggc tct gtg ttt ggg cag        723
Gly Gly Ser Pro Ser Ile Lys Glu Asn Ile Gly Ser Val Phe Gly Gln
        220                 225                 230 aag cag ttg caa agc ctc att cct ttt gtt cag ctg ccc cct agt gac        771
Lys Gln Leu Gln Ser Leu Ile Pro Phe Val Gln Leu Pro Pro Ser Asp
```

|                      |       |     |     |     |     |     |     |     |     |     |     |     |     |     |     |     |      |
|----------------------|-------|-----|-----|-----|-----|-----|-----|-----|-----|-----|-----|-----|-----|-----|-----|-----|------|
|                      | 235   |     |     |     | 240 |     |     |     |     | 245 |     |     |     |     |     |     |      |
| tcc | gtg | tgt | gaa | gag | tac | ggt | ttg | agc | tgt | tcg | gat | gct | ctg | cat | aat |     | 819  |
| Ser | Val | Cys | Glu | Glu | Tyr | Gly | Leu | Ser | Cys | Ser | Asp | Ala | Leu | His | Asn |     |      |
| 250 |     |     |     |     | 255 |     |     |     |     | 260 |     |     |     |     | 265 |     |      | ctt ttt tac atc tca ggt ttc att tca caa tgc acg cat gga gtt gga    867
Leu Phe Tyr Ile Ser Gly Phe Ile Ser Gln Cys Thr His Gly Val Gly
            270                 275                 280 agg agt tca aca gac aga cag ttt ttc ttt atc aac cgg cgg cct tgt    915
Arg Ser Ser Thr Asp Arg Gln Phe Phe Phe Ile Asn Arg Arg Pro Cys
                285                 290                 295 gac cca gca aag gtc tgc aga ctc gtg aat gag gtc tac cac atg tat    963
Asp Pro Ala Lys Val Cys Arg Leu Val Asn Glu Val Tyr His Met Tyr
                    300                 305                 310 aat cga cac cag tat cca ttt gtt gtt ctt aac att tct gtt gat tca    1011
Asn Arg His Gln Tyr Pro Phe Val Val Leu Asn Ile Ser Val Asp Ser
        315                 320                 325 gaa tgc gtt gat atc aat gtt act cca gat aaa agg caa att ttg cta    1059
Glu Cys Val Asp Ile Asn Val Thr Pro Asp Lys Arg Gln Ile Leu Leu
330                 335                 340                 345 caa gag gaa aag ctt ttg ttg gca gtt tta aag acc tct ttg ata gga    1107
Gln Glu Glu Lys Leu Leu Leu Ala Val Leu Lys Thr Ser Leu Ile Gly
                350                 355                 360 atg ttt gat agt gat gtc aac aag cta aat gtc agt cag cag cca ctg    1155
Met Phe Asp Ser Asp Val Asn Lys Leu Asn Val Ser Gln Gln Pro Leu
                365                 370                 375 ctg gat gtt gaa ggt aac tta ata aaa atg cat gca gcg gat ttg gaa    1203
Leu Asp Val Glu Gly Asn Leu Ile Lys Met His Ala Ala Asp Leu Glu
            380                 385                 390 aag ccc atg gta gaa aag cag gat caa tcc cct tca tta agg act gga    1251
Lys Pro Met Val Glu Lys Gln Asp Gln Ser Pro Ser Leu Arg Thr Gly
            395                 400                 405 gaa gaa aaa aaa gac gtg tcc att tcc aga ctg cga gag gcc ttt tct    1299
Glu Glu Lys Lys Asp Val Ser Ile Ser Arg Leu Arg Glu Ala Phe Ser
410                 415                 420                 425 ctt cgt cac aca aca gag aac aag cct cac agc cca aag act cca gaa    1347
Leu Arg His Thr Thr Glu Asn Lys Pro His Ser Pro Lys Thr Pro Glu
                430                 435                 440 cca aga agg agc cct cta gga cag aaa agg ggt atg ctg tct tct agc    1395
Pro Arg Arg Ser Pro Leu Gly Gln Lys Arg Gly Met Leu Ser Ser Ser
                445                 450                 455 act tca ggt gcc atc tct gac aaa ggc gtc ctg aga cct cag aaa gag    1443
Thr Ser Gly Ala Ile Ser Asp Lys Gly Val Leu Arg Pro Gln Lys Glu
            460                 465                 470 gca gtg agt tcc agt cac gga ccc agt gac cct acg gac aga gcg gag    1491
Ala Val Ser Ser Ser His Gly Pro Ser Asp Pro Thr Asp Arg Ala Glu
    475                 480                 485 gtg gag aag gac tcg ggg cac ggc agc act tcc gtg gat tct gag ggg    1539
Val Glu Lys Asp Ser Gly His Gly Ser Thr Ser Val Asp Ser Glu Gly
490                 495                 500                 505 ttc agc atc cca gac acg ggc agt cac tgc agc agc gag tat gcg gcc    1587
Phe Ser Ile Pro Asp Thr Gly Ser His Cys Ser Ser Glu Tyr Ala Ala
            510                 515                 520 agc tcc cca ggg gac agg ggc tcg cag gaa cat gtg gac tct cag gag    1635
Ser Ser Pro Gly Asp Arg Gly Ser Gln Glu His Val Asp Ser Gln Glu
            525                 530                 535 aaa gcg cct gaa act gac gac tct ttt tca gat gtg gac tgc cat tca    1683
Lys Ala Pro Glu Thr Asp Asp Ser Phe Ser Asp Val Asp Cys His Ser
            540                 545                 550 aac cag gaa gat acc gga tgt aaa ttt cga gtt ttg cct cag cca act    1731

```
                                                                   -continued Asn Gln Glu Asp Thr Gly Cys Lys Phe Arg Val Leu Pro Gln Pro Thr
    555                 560                 565 aat ctc gca acc cca aac aca aag cgt ttt aaa aaa gaa gaa att ctt        1779
Asn Leu Ala Thr Pro Asn Thr Lys Arg Phe Lys Lys Glu Glu Ile Leu
570                 575                 580                 585 tcc agt tct gac att tgt caa aag tta gta aat act cag gac atg tca        1827
Ser Ser Ser Asp Ile Cys Gln Lys Leu Val Asn Thr Gln Asp Met Ser
                590                 595                 600 gcc tct cag gtt gat gta gct gtg aaa att aat aag aaa gtt gtg ccc        1875
Ala Ser Gln Val Asp Val Ala Val Lys Ile Asn Lys Lys Val Val Pro
            605                 610                 615 ctg gac ttt tct atg agt tct tta gct aaa cga ata aag cag tta cat        1923
Leu Asp Phe Ser Met Ser Ser Leu Ala Lys Arg Ile Lys Gln Leu His
        620                 625                 630 cat gaa gca cag caa agt gaa ggg gaa cag aat tac agg aag ttt agg        1971
His Glu Ala Gln Gln Ser Glu Gly Glu Gln Asn Tyr Arg Lys Phe Arg
    635                 640                 645 gca aag att tgt cct gga gaa aat caa gca gcc gaa gat gaa cta aga        2019
Ala Lys Ile Cys Pro Gly Glu Asn Gln Ala Ala Glu Asp Glu Leu Arg
650                 655                 660                 665 aaa gag ata agt aaa acg atg ttt gca gaa atg gaa atc att ggt cag        2067
Lys Glu Ile Ser Lys Thr Met Phe Ala Glu Met Glu Ile Ile Gly Gln
                670                 675                 680 ttt aac ctg gga ttt ata ata acc aaa ctg aat gag gat atc ttc ata        2115
Phe Asn Leu Gly Phe Ile Ile Thr Lys Leu Asn Glu Asp Ile Phe Ile
            685                 690                 695 gtg gac cag cat gcc acg gac gag aag tat aac ttc gag atg ctg cag        2163
Val Asp Gln His Ala Thr Asp Glu Lys Tyr Asn Phe Glu Met Leu Gln
        700                 705                 710 cag cac acc gtg ctc cag ggg cag agg ctc ata gca cct cag act ctc        2211
Gln His Thr Val Leu Gln Gly Gln Arg Leu Ile Ala Pro Gln Thr Leu
    715                 720                 725 aac tta act gct gtt aat gaa gct gtt ctg ata gaa aat ctg gaa ata        2259
Asn Leu Thr Ala Val Asn Glu Ala Val Leu Ile Glu Asn Leu Glu Ile
730                 735                 740                 745 ttt aga aag aat ggc ttt gat ttt gtt atc gat gaa aat gct cca gtc        2307
Phe Arg Lys Asn Gly Phe Asp Phe Val Ile Asp Glu Asn Ala Pro Val
                750                 755                 760 act gaa agg gct aaa ctg att tcc ttg cca act agt aaa aac tgg acc        2355
Thr Glu Arg Ala Lys Leu Ile Ser Leu Pro Thr Ser Lys Asn Trp Thr
            765                 770                 775 ttc gga ccc cag gac gtc gat gaa ctg atc ttc atg ctg agc gac agc        2403
Phe Gly Pro Gln Asp Val Asp Glu Leu Ile Phe Met Leu Ser Asp Ser
        780                 785                 790 cct ggg gtc atg tgc cgg cct tcc cga gtc aag cag atg ttt gcc tcc        2451
Pro Gly Val Met Cys Arg Pro Ser Arg Val Lys Gln Met Phe Ala Ser
    795                 800                 805 aga gcc tgc cgg aag tcg gtg atg att ggg act gct ctt aac aca agc        2499
Arg Ala Cys Arg Lys Ser Val Met Ile Gly Thr Ala Leu Asn Thr Ser
810                 815                 820                 825 gag atg aag aaa ctg atc acc cac atg ggg gag atg gac cac ccc tgg        2547
Glu Met Lys Lys Leu Ile Thr His Met Gly Glu Met Asp His Pro Trp
                830                 835                 840 aac tgt ccc cat gga agg cca acc atg aga cac atc gcc aac ctg ggt        2595
Asn Cys Pro His Gly Arg Pro Thr Met Arg His Ile Ala Asn Leu Gly
            845                 850                 855 gtc att tct cag aac tga ccgtagtcac tgtatggaat aattggtttt              2643
Val Ile Ser Gln Asn
        860
```

-continued

```
atcgcagatt tttatgtttt gaaagacaga gtcttcacta acctttttg ttttaaaatg    2703 aaacctgcta cttaaaaaaa atacacatca cacccattta aaagtgatct tgagaacctt    2763
ttcaaacc                                                              2771
```

<210> SEQ ID NO 6
<211> LENGTH: 862
<212> TYPE: PRT
<213> ORGANISM: homo sapiens

<400> SEQUENCE: 6

```
Met Glu Arg Ala Glu Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr Arg Leu Met Phe Asp His Asn Gly Lys Ile Ile
    130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Thr Gly Gly Ser Pro Ser Ile Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270

Ile Ser Gln Cys Thr His Gly Val Gly Arg Ser Ser Thr Asp Arg Gln
        275                 280                 285

Phe Phe Phe Ile Asn Arg Arg Pro Cys Asp Pro Ala Lys Val Cys Arg
    290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350
```

```
Ala Val Leu Lys Thr Ser Leu Ile Gly Met Phe Asp Ser Asp Val Asn
            355                 360                 365

Lys Leu Asn Val Ser Gln Gln Pro Leu Leu Asp Val Glu Gly Asn Leu
    370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
                405                 410                 415

Ile Ser Arg Leu Arg Glu Ala Phe Ser Leu Arg His Thr Thr Glu Asn
            420                 425                 430

Lys Pro His Ser Pro Lys Thr Pro Glu Pro Arg Arg Ser Pro Leu Gly
        435                 440                 445

Gln Lys Arg Gly Met Leu Ser Ser Ser Thr Ser Gly Ala Ile Ser Asp
    450                 455                 460

Lys Gly Val Leu Arg Pro Gln Lys Glu Ala Val Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
            500                 505                 510

Ser His Cys Ser Ser Glu Tyr Ala Ala Ser Ser Pro Gly Asp Arg Gly
        515                 520                 525

Ser Gln Glu His Val Asp Ser Gln Glu Lys Ala Pro Glu Thr Asp Asp
    530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
                565                 570                 575

Lys Arg Phe Lys Lys Glu Glu Ile Leu Ser Ser Ser Asp Ile Cys Gln
            580                 585                 590

Lys Leu Val Asn Thr Gln Asp Met Ser Ala Ser Gln Val Asp Val Ala
        595                 600                 605

Val Lys Ile Asn Lys Lys Val Val Pro Leu Asp Phe Ser Met Ser Ser
    610                 615                 620

Leu Ala Lys Arg Ile Lys Gln Leu His His Glu Ala Gln Gln Ser Glu
625                 630                 635                 640

Gly Glu Gln Asn Tyr Arg Lys Phe Arg Ala Lys Ile Cys Pro Gly Glu
                645                 650                 655

Asn Gln Ala Ala Glu Asp Glu Leu Arg Lys Glu Ile Ser Lys Thr Met
            660                 665                 670

Phe Ala Glu Met Glu Ile Ile Gly Gln Phe Asn Leu Gly Phe Ile Ile
        675                 680                 685

Thr Lys Leu Asn Glu Asp Ile Phe Ile Val Asp Gln His Ala Thr Asp
    690                 695                 700

Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
                725                 730                 735

Ala Val Leu Ile Glu Asn Leu Glu Ile Phe Arg Lys Asn Gly Phe Asp
            740                 745                 750

Phe Val Ile Asp Glu Asn Ala Pro Val Thr Glu Arg Ala Lys Leu Ile
        755                 760                 765
```

```
Ser Leu Pro Thr Ser Lys Asn Trp Thr Phe Gly Pro Gln Asp Val Asp
    770                 775                 780
Glu Leu Ile Phe Met Leu Ser Asp Ser Pro Gly Val Met Cys Arg Pro
785                 790                 795                 800
Ser Arg Val Lys Gln Met Phe Ala Ser Arg Ala Cys Arg Lys Ser Val
                805                 810                 815
Met Ile Gly Thr Ala Leu Asn Thr Ser Glu Met Lys Lys Leu Ile Thr
            820                 825                 830
His Met Gly Glu Met Asp His Pro Trp Asn Cys Pro His Gly Arg Pro
        835                 840                 845
Thr Met Arg His Ile Ala Asn Leu Gly Val Ile Ser Gln Asn
    850                 855                 860

<210> SEQ ID NO 7
<211> LENGTH: 20
<212> TYPE: DNA
<213> ORGANISM: Artificial Sequence
<220> FEATURE:
<223> OTHER INFORMATION: hMLH1 sense primer

<400> SEQUENCE: 7
gttgaacatc tagacgtctc                                             20

<210> SEQ ID NO 8
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 8
tcgtggcagg ggttattcg                                              19

<210> SEQ ID NO 9
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 9
ctacccaatg cctcaaccg                                              19

<210> SEQ ID NO 10
<211> LENGTH: 22
<212> TYPE: DNA
<213> ORGANISM: Artificial Sequence
<220> FEATURE:
<223> OTHER INFORMATION: hMLH1 sense primer

<400> SEQUENCE: 10
gagaactgat agaaattgga tg                                          22

<210> SEQ ID NO 11
<211> LENGTH: 18
<212> TYPE: DNA
<213> ORGANISM: Artificial Sequence
<220> FEATURE:
<223> OTHER INFORMATION: hMLH1 sense primer

<400> SEQUENCE: 11
gggacatgag gttctccg                                               18
```

```
<210> SEQ ID NO 12
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 12
gggctgtgtg aatcctcag                                                    19

<210> SEQ ID NO 13
<211> LENGTH: 20
<212> TYPE: DNA
<213> ORGANISM: Artificial Sequence
<220> FEATURE:
<223> OTHER INFORMATION: hMLH1 antisense primer

<400> SEQUENCE: 13
cggttcacca ctgtctcgtc                                                   20

<210> SEQ ID NO 14
<211> LENGTH: 18
<212> TYPE: DNA
<213> ORGANISM: Artificial Sequence
<220> FEATURE:
<223> OTHER INFORMATION: hMLH1 antisense primer

<400> SEQUENCE: 14
tccaggatgc tctcctcg                                                     18

<210> SEQ ID NO 15
<211> LENGTH: 20
<212> TYPE: DNA
<213> ORGANISM: Artificial Sequence
<220> FEATURE:
<223> OTHER INFORMATION: hMLH1 antisense primer

<400> SEQUENCE: 15
caagtcctgg tagcaaagtc                                                   20

<210> SEQ ID NO 16
<211> LENGTH: 19
<212> TYPE: DNA
<213> ORGANISM: Artificial Sequence
<220> FEATURE:
<223> OTHER INFORMATION: hMLH1 antisense primer

<400> SEQUENCE: 16
atggcaaggt caaagagcg                                                    19

<210> SEQ ID NO 17
<211> LENGTH: 22
<212> TYPE: DNA
<213> ORGANISM: Artificial Sequence
<220> FEATURE:
<223> OTHER INFORMATION: hMLH1 antisense primer
<221> NAME/KEY: misc_feature
<222> LOCATION: (22)..(22)
<223> OTHER INFORMATION: n equals a, t, g or c

<400> SEQUENCE: 17
caacaatgta ttcagnaagt cc                                                22

<210> SEQ ID NO 18
<211> LENGTH: 21
<212> TYPE: DNA
<213> ORGANISM: Artificial Sequence
```

```
<220> FEATURE:
<223> OTHER INFORMATION: hMLH1 antisense primer

<400> SEQUENCE: 18
ttgatacaac actttgtatc g                                              21

<210> SEQ ID NO 19
<211> LENGTH: 21
<212> TYPE: DNA
<213> ORGANISM: Artificial Sequence
<220> FEATURE:
<223> OTHER INFORMATION: hMLH1 antisense primer

<400> SEQUENCE: 19
ggaatactat cagaaggcaa g                                              21

<210> SEQ ID NO 20
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 20
acagagcaag ttactcagat g                                              21

<210> SEQ ID NO 21
<211> LENGTH: 20
<212> TYPE: DNA
<213> ORGANISM: Artificial Sequence
<220> FEATURE:
<223> OTHER INFORMATION: hMLH1 sense primer

<400> SEQUENCE: 21
gtacacaatg caggcattag                                                20

<210> SEQ ID NO 22
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 22
aatgtggatg ttaatgtgca c                                              21

<210> SEQ ID NO 23
<211> LENGTH: 18
<212> TYPE: DNA
<213> ORGANISM: Artificial Sequence
<220> FEATURE:
<223> OTHER INFORMATION: hMLH1 sense primer

<400> SEQUENCE: 23
ctgacctcgt cttcctac                                                  18

<210> SEQ ID NO 24
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 24
cagcaagatg aggagatgc                                                 19
```

```
<210> SEQ ID NO 25
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 25
ggaaatggtg gaagatgatt c                                              21

<210> SEQ ID NO 26
<211> LENGTH: 16
<212> TYPE: DNA
<213> ORGANISM: Artificial Sequence
<220> FEATURE:
<223> OTHER INFORMATION: hMLH1 sense primer

<400> SEQUENCE: 26
cttctcaaca ccaagc                                                    16

<210> SEQ ID NO 27
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 27
gaaattgatg aggaagggaa c                                              21

<210> SEQ ID NO 28
<211> LENGTH: 22
<212> TYPE: DNA
<213> ORGANISM: Artificial Sequence
<220> FEATURE:
<223> OTHER INFORMATION: hMLH1 sense primer

<400> SEQUENCE: 28
cttctgattg acaactatgt gc                                             22

<210> SEQ ID NO 29
<211> LENGTH: 22
<212> TYPE: DNA
<213> ORGANISM: Artificial Sequence
<220> FEATURE:
<223> OTHER INFORMATION: hMLH1 sense primer

<400> SEQUENCE: 29
cacagaagat ggaaatatcc tg                                             22

<210> SEQ ID NO 30
<211> LENGTH: 20
<212> TYPE: DNA
<213> ORGANISM: Artificial Sequence
<220> FEATURE:
<223> OTHER INFORMATION: hMLH1 sense primer

<400> SEQUENCE: 30
gtgttggtag cacttaagac                                                20

<210> SEQ ID NO 31
<211> LENGTH: 20
<212> TYPE: DNA
<213> ORGANISM: Artificial Sequence
<220> FEATURE:
<223> OTHER INFORMATION: hMLH1 antisense primer
```

```
<400> SEQUENCE: 31
tttcccatat tcttcacttg                                                    20

<210> SEQ ID NO 32
<211> LENGTH: 19
<212> TYPE: DNA
<213> ORGANISM: Artificial Sequence
<220> FEATURE:
<223> OTHER INFORMATION: hMLH1 antisense primer

<400> SEQUENCE: 32
gtaacatgag ccacatggc                                                     19

<210> SEQ ID NO 33
<211> LENGTH: 19
<212> TYPE: DNA
<213> ORGANISM: Artificial Sequence
<220> FEATURE:
<223> OTHER INFORMATION: hMLH1 antisense primer

<400> SEQUENCE: 33
ccactgtctc gtccagccg                                                     19

<210> SEQ ID NO 34
<211> LENGTH: 26
<212> TYPE: DNA
<213> ORGANISM: Artificial Sequence
<220> FEATURE:
<223> OTHER INFORMATION: hMLH1 5' primer with BamHI restriction site

<400> SEQUENCE: 34
cgggatccat gtcgttcgtg gcaggg                                             26

<210> SEQ ID NO 35
<211> LENGTH: 26
<212> TYPE: DNA
<213> ORGANISM: Artificial Sequence
<220> FEATURE:
<223> OTHER INFORMATION: hMLH1 3' primer with XbaI restriction site

<400> SEQUENCE: 35
gctctagatt aacacctctc aaagac                                             26

<210> SEQ ID NO 36
<211> LENGTH: 21
<212> TYPE: DNA
<213> ORGANISM: Artificial Sequence
<220> FEATURE:
<223> OTHER INFORMATION: hMLH1 primer useful for amplifying codons 1 to
      394

<400> SEQUENCE: 36
gcatctagac gtttccttgg c                                                  21

<210> SEQ ID NO 37
<211> LENGTH: 20
<212> TYPE: DNA
<213> ORGANISM: Artificial Sequence
<220> FEATURE:
<223> OTHER INFORMATION: primer useful for amplifying codons 1 to 394 of
      hMLH1

<400> SEQUENCE: 37
catccaagct tctgttcccg                                                    20
```

<210> SEQ ID NO 38
<211> LENGTH: 19
<212> TYPE: DNA
<213> ORGANISM: Artificial Sequence
<220> FEATURE:
<223> OTHER INFORMATION: primer useful for amplifying codons 326 to 729
of hMLH1

<400> SEQUENCE: 38
ggggtgcagc agcacatcg                                                 19

<210> SEQ ID NO 39
<211> LENGTH: 20
<212> TYPE: DNA
<213> ORGANISM: Artificial Sequence
<220> FEATURE:
<223> OTHER INFORMATION: primer useful for amplifying codons 326 to 729
of hMLH1

<400> SEQUENCE: 39
ggaggcagaa tgtgtgagcg                                                20

<210> SEQ ID NO 40
<211> LENGTH: 19
<212> TYPE: DNA
<213> ORGANISM: Artificial Sequence
<220> FEATURE:
<223> OTHER INFORMATION: primer useful for amplifying codons 602 to 756
plus 128 nucleotides of 3' untranslated sequence of hMLH1

<400> SEQUENCE: 40
tcccaaagaa ggacttgct                                                 19

<210> SEQ ID NO 41
<211> LENGTH: 22
<212> TYPE: DNA
<213> ORGANISM: Artificial Sequence
<220> FEATURE:
<223> OTHER INFORMATION: primer useful for amplifying codons 602 to 756
plus 128 nucleotides of 3' untranslated sequence of hMLH1

<400> SEQUENCE: 41
agtataagtc ttaagtgcta cc                                             22

<210> SEQ ID NO 42
<211> LENGTH: 20
<212> TYPE: DNA
<213> ORGANISM: Artificial Sequence
<220> FEATURE:
<223> OTHER INFORMATION: primer useful for amplifying codons 578 to 632
of hMLH1

<400> SEQUENCE: 42
tttatggttt ctcacctgcc                                                20

<210> SEQ ID NO 43
<211> LENGTH: 19
<212> TYPE: DNA
<213> ORGANISM: Artificial Sequence
<220> FEATURE:
<223> OTHER INFORMATION: primer useful for amplifying codons 578 to 632
of hMLH1

<400> SEQUENCE: 43
gttatctgcc cacctcagc                                                 19

```
<210> SEQ ID NO 44
<211> LENGTH: 59
<212> TYPE: DNA
<213> ORGANISM: Artificial Sequence
<220> FEATURE:
<223> OTHER INFORMATION: primer useful for amplifying codons 1 to 394 of
      hMLH1 wherein PCR product may be used for coupled
      transcription-translation

<400> SEQUENCE: 44
ggatcctaat acgactcact atagggagac caccatggca tctagacgtt tcccttggc      59

<210> SEQ ID NO 45
<211> LENGTH: 20
<212> TYPE: DNA
<213> ORGANISM: Artificial Sequence
<220> FEATURE:
<223> OTHER INFORMATION: primer useful for amplifying codons 1 to 394 of
      hMLH1 wherein PCR product may be used for coupled
      transcription-translation

<400> SEQUENCE: 45
catccaagct tctgttcccg                                                 20

<210> SEQ ID NO 46
<211> LENGTH: 56
<212> TYPE: DNA
<213> ORGANISM: Artificial Sequence
<220> FEATURE:
<223> OTHER INFORMATION: primer useful for amplifying codons 326 to 729
      of hMLH1 wherein PCR product may be used for coupled
      transcription-translation

<400> SEQUENCE: 46
ggatcctaat acgactcact atagggagac caccatgggg gtgcagcagc acatcg         56

<210> SEQ ID NO 47
<211> LENGTH: 20
<212> TYPE: DNA
<213> ORGANISM: Artificial Sequence
<220> FEATURE:
<223> OTHER INFORMATION: primer useful for amplifying codons 326 to 729
      of hMLH1 wherein PCR product may be used for coupled
      transcription-translation

<400> SEQUENCE: 47
ggaggcagaa tgtgtgagcg                                                 20

<210> SEQ ID NO 48
<211> LENGTH: 28
<212> TYPE: DNA
<213> ORGANISM: Artificial Sequence
<220> FEATURE:
<223> OTHER INFORMATION: hMLH2 5' primer with a BamHI restriction site

<400> SEQUENCE: 48
cgggatccat gaaacaattg cctgcggc                                        28

<210> SEQ ID NO 49
<211> LENGTH: 26
<212> TYPE: DNA
<213> ORGANISM: Artificial Sequence
<220> FEATURE:
<223> OTHER INFORMATION: hMLH2 3' primer with XbaI restriction site

<400> SEQUENCE: 49
gctctagacc agactcatgc tgtttt                                          26
```

<210> SEQ ID NO 50
<211> LENGTH: 26
<212> TYPE: DNA
<213> ORGANISM: Artificial Sequence
<220> FEATURE:
<223> OTHER INFORMATION: hMLH3 5' primer with a BamHI restriction site

<400> SEQUENCE: 50
cgggatccat ggagcgagct gagagc                                26

<210> SEQ ID NO 51
<211> LENGTH: 23
<212> TYPE: DNA
<213> ORGANISM: Artificial Sequence
<220> FEATURE:
<223> OTHER INFORMATION: hMLH3 3' primer with XbaI restriction site

<400> SEQUENCE: 51
gctctagagt gaagactctg tct                                   23

<210> SEQ ID NO 52
<211> LENGTH: 20
<212> TYPE: DNA
<213> ORGANISM: Artificial Sequence
<220> FEATURE:
<223> OTHER INFORMATION: hMLH2 primer

<400> SEQUENCE: 52
aagctgctct gttaaaagcg                                       20

<210> SEQ ID NO 53
<211> LENGTH: 18
<212> TYPE: DNA
<213> ORGANISM: Artificial Sequence
<220> FEATURE:
<223> OTHER INFORMATION: hMLH2 primer

<400> SEQUENCE: 53
gcaccagcat ccaaggag                                         18

<210> SEQ ID NO 54
<211> LENGTH: 19
<212> TYPE: DNA
<213> ORGANISM: Artificial Sequence
<220> FEATURE:
<223> OTHER INFORMATION: hMLH3 primer

<400> SEQUENCE: 54
caaccatgag acacatcgc                                        19

<210> SEQ ID NO 55
<211> LENGTH: 20
<212> TYPE: DNA
<213> ORGANISM: Artificial Sequence
<220> FEATURE:
<223> OTHER INFORMATION: hMLH3 primer

<400> SEQUENCE: 55
aggttagtga agactctgtc                                       20

<210> SEQ ID NO 56
<211> LENGTH: 53
<212> TYPE: DNA
<213> ORGANISM: Artificial Sequence
<220> FEATURE:
<223> OTHER INFORMATION: primer useful for amplifying codons 1 to 500 of hMLH2

<400> SEQUENCE: 56
ggatcctaat acgactcact atagggagac caccatggaa caattgcctg cgg        53

<210> SEQ ID NO 57
<211> LENGTH: 18
<212> TYPE: DNA
<213> ORGANISM: Artificial Sequence
<220> FEATURE:
<223> OTHER INFORMATION: primer useful for amplifying codons 1 to 500 of
      hMLH2

<400> SEQUENCE: 57
cctgctccac tcatctgc                                                18

<210> SEQ ID NO 58
<211> LENGTH: 60
<212> TYPE: DNA
<213> ORGANISM: Artificial Sequence
<220> FEATURE:
<223> OTHER INFORMATION: primer useful for amplifying codons 270 to 755
      of hMLH2

<400> SEQUENCE: 58
ggatcctaat acgactcact atagggagac caccatggaa gatatcttaa agttaatccg   60

<210> SEQ ID NO 59
<211> LENGTH: 21
<212> TYPE: DNA
<213> ORGANISM: Artificial Sequence
<220> FEATURE:
<223> OTHER INFORMATION: primer useful for amplifying codons 270 to 755
      of hMLH2

<400> SEQUENCE: 59
ggcttcttct actctatatg g                                            21

<210> SEQ ID NO 60
<211> LENGTH: 58
<212> TYPE: DNA
<213> ORGANISM: Artificial Sequence
<220> FEATURE:
<223> OTHER INFORMATION: primer useful for amplifying from codon 485 to
      the translation termination site at codon 933 of hMLH2

<400> SEQUENCE: 60
ggatcctaat acgactcact atagggagac caccatggca ggtcttgaaa actcttcg    58

<210> SEQ ID NO 61
<211> LENGTH: 21
<212> TYPE: DNA
<213> ORGANISM: Artificial Sequence
<220> FEATURE:
<223> OTHER INFORMATION: primer useful for amplifying from codon 485 to
      the translation termination site at codon 933 of hMLH2

<400> SEQUENCE: 61
aaaacaagtc agtgaatcct c                                            21

<210> SEQ ID NO 62
<211> LENGTH: 20
<212> TYPE: DNA
<213> ORGANISM: Artificial Sequence
<220> FEATURE:
<223> OTHER INFORMATION: 3' primer useful for amplifying up to codon 369
      of hMLH2

<400> SEQUENCE: 62
aagcacatct gtttctgctg                                                    20

<210> SEQ ID NO 63
<211> LENGTH: 20
<212> TYPE: DNA
<213> ORGANISM: Artificial Sequence
<220> FEATURE:
<223> OTHER INFORMATION: 3' primer useful for amplifying up to codon 290
      of hMLH2

<400> SEQUENCE: 63
acgagtagat tcctttaggc                                                    20

<210> SEQ ID NO 64
<211> LENGTH: 19
<212> TYPE: DNA
<213> ORGANISM: Artificial Sequence
<220> FEATURE:
<223> OTHER INFORMATION: 3' primer useful for amplifying up to codon 214
      of hMLH2

<400> SEQUENCE: 64
cagaactgac atgagagcc                                                     19

<210> SEQ ID NO 65
<211> LENGTH: 52
<212> TYPE: DNA
<213> ORGANISM: Artificial Sequence
<220> FEATURE:
<223> OTHER INFORMATION: primer useful for amplifying codons 1 to 863
      hMLH3

<400> SEQUENCE: 65
ggatcctaat acgactcact atagggagac caccatggag cgagctgaga gc                52

<210> SEQ ID NO 66
<211> LENGTH: 20
<212> TYPE: DNA
<213> ORGANISM: Artificial Sequence
<220> FEATURE:
<223> OTHER INFORMATION: primer useful for amplifying codons 1 to 863
      hMLH3

<400> SEQUENCE: 66
aggttagtga agactctgtc                                                    20

<210> SEQ ID NO 67
<211> LENGTH: 17
<212> TYPE: DNA
<213> ORGANISM: Artificial Sequence
<220> FEATURE:
<223> OTHER INFORMATION: primer useful for amplifying up to codon 472 of
      hMLH3

<400> SEQUENCE: 67
ctgaggtctc agcaggc                                                       17

<210> SEQ ID NO 68
<211> LENGTH: 57
<212> TYPE: DNA
<213> ORGANISM: Artificial Sequence
<220> FEATURE:
<223> OTHER INFORMATION: primer useful for amplifying codons 415 to 863
      of hMLH3

```
<400> SEQUENCE: 68
ggatcctaat acgactcact atagggagac caccatggtg tccatttcca gactgcg         57

<210> SEQ ID NO 69
<211> LENGTH: 20
<212> TYPE: DNA
<213> ORGANISM: Artificial Sequence
<220> FEATURE:
<223> OTHER INFORMATION: primer useful for amplifying codons 415 to 863
      of hMLH3

<400> SEQUENCE: 69
aggttagtga agactctgtc                                                   20

<210> SEQ ID NO 70
<211> LENGTH: 21
<212> TYPE: DNA
<213> ORGANISM: Artificial Sequence
<220> FEATURE:
<223> OTHER INFORMATION: primer useful for amplifying codons 195 to 233
      of hMLH2

<400> SEQUENCE: 70
ttatttggca gaaaagcaga g                                                 21

<210> SEQ ID NO 71
<211> LENGTH: 21
<212> TYPE: DNA
<213> ORGANISM: Artificial Sequence
<220> FEATURE:
<223> OTHER INFORMATION: primer useful for amplifying codons 195 to 233
      of hMLH2

<400> SEQUENCE: 71
ttaaaagact aacctcttgc c                                                 21

<210> SEQ ID NO 72
<211> LENGTH: 21
<212> TYPE: DNA
<213> ORGANISM: Artificial Sequence
<220> FEATURE:
<223> OTHER INFORMATION: sequencing primer useful for sequencing codons
      195 to 233 of hMLH2

<400> SEQUENCE: 72
ctgctgttat gaacaatatg g                                                 21

<210> SEQ ID NO 73
<211> LENGTH: 19
<212> TYPE: DNA
<213> ORGANISM: Artificial Sequence
<220> FEATURE:
<223> OTHER INFORMATION: primer useful for amplifying codons 233 to 257
      of hMLH3

<400> SEQUENCE: 73
cagaagcagt tgcaaagcc                                                    19

<210> SEQ ID NO 74
<211> LENGTH: 20
<212> TYPE: DNA
<213> ORGANISM: Artificial Sequence
<220> FEATURE:
<223> OTHER INFORMATION: primer useful for amplifying codons 233 to 257
      of hMLH3

<400> SEQUENCE: 74
```

```
aaaccgtact cttcacacac                                               20

<210> SEQ ID NO 75
<211> LENGTH: 20
<212> TYPE: DNA
<213> ORGANISM: Artificial Sequence
<220> FEATURE:
<223> OTHER INFORMATION: primer useful for amplifying codons 347 of 377
      of hMLH3

<400> SEQUENCE: 75
gaggaaaagc ttttgttggc                                               20

<210> SEQ ID NO 76
<211> LENGTH: 18
<212> TYPE: DNA
<213> ORGANISM: Artificial Sequence
<220> FEATURE:
<223> OTHER INFORMATION: primer useful for amplifying codons 347 of 377
      of hMLH3

<400> SEQUENCE: 76
cagtggctgc tgactgac                                                 18

<210> SEQ ID NO 77
<211> LENGTH: 19
<212> TYPE: DNA
<213> ORGANISM: Artificial Sequence
<220> FEATURE:
<223> OTHER INFORMATION: primer useful for amplifying codons 439 to 472
      of hMLH3

<400> SEQUENCE: 77
tccagaacca agaaggagc                                                19

<210> SEQ ID NO 78
<211> LENGTH: 16
<212> TYPE: DNA
<213> ORGANISM: Artificial Sequence
<220> FEATURE:
<223> OTHER INFORMATION: primer useful for amplifying codons 439 to 472
      of hMLH3

<400> SEQUENCE: 78
tgaggtctca gcaggc                                                   16
```